US012740807B2

(12) United States Patent
O'Dea et al.

(10) Patent No.: US 12,740,807 B2
(45) Date of Patent: Sep. 22, 2026

(54) VALVE MECHANISM

(71) Applicant: Palliare Limited, Dangan (IE)

(72) Inventors: John O'Dea, Bearna (IE); Hilary Elizabeth Barrett, Castletroy (IE); Robert Gorby Mccarthy, Dun Laoghaire (IE); Kelley Josephine Mary Horgan, Kinsale (IE); Martin James Hamilton Bruggemann, Mountrath (IE); Daragh Michael Manning, Clontarf (IE)

(73) Assignee: Palliare Limited, Galway (IE)

( * ) Notice: Subject to any disclaimer, the term of this patent is extended or adjusted under 35 U.S.C. 154(b) by 666 days.

(21) Appl. No.: 17/927,629

(22) PCT Filed: May 27, 2021

(86) PCT No.: PCT/IE2021/000011

§ 371 (c)(1),
(2) Date: Nov. 23, 2022

(87) PCT Pub. No.: WO2021/240493

PCT Pub. Date: Dec. 2, 2021

(65) Prior Publication Data

US 2023/0172634 A1 Jun. 8, 2023

(30) Foreign Application Priority Data

May 27, 2020 (IE) .................................... 2020/0116
May 27, 2020 (IE) .................................... 2020/0117

(51) Int. Cl.
*A61B 17/34* (2006.01)
*A61B 17/00* (2006.01)

(52) U.S. Cl.
CPC ...... *A61B 17/3462* (2013.01); *A61B 17/3423* (2013.01); *A61B 17/3498* (2013.01);
(Continued)

(58) Field of Classification Search
CPC ............ A61B 17/3462; A61B 17/3498; A61B 17/3423; A61B 17/3439
See application file for complete search history.

(56) References Cited

U.S. PATENT DOCUMENTS 5,129,885 A 7/1992 Green et al.
5,201,714 A * 4/1993 Gentelia ............ A61B 17/3462 604/250

(Continued)

FOREIGN PATENT DOCUMENTS

DE 70 04 051 U 7/1970
DE 10 2007 023 427 A1 11/2008

(Continued)

OTHER PUBLICATIONS

International Search Report for PCT/IE2021/000011 dated Nov. 5, 2021 [PCT/ISA/210].

(Continued)

*Primary Examiner* — Brigid K Byrd
(74) *Attorney, Agent, or Firm* — Sughrue Mion, PLLC

(57) ABSTRACT

A valve mechanism (3) for attaching to a proximal end (4) of a trocar cannula (2) for minimising leakage of insufflating and other gases proximally from the trocar cannula (2), comprises a housing (7) adapted for securing to the trocar cannula (2) adjacent the proximal end (4) thereof. The housing (7) defines an instrument bore (22) extending from a proximal end (23) to a distal end (21). A distal valve (28) is located adjacent the distal end (21) of the instrument bore (22) and is pivotal from an open state to a closed state. A proximal valve (40) is located towards the proximal end (23) of the instrument bore (22), and comprises first and second valve members (41) and (42) which are urgeable from a withdrawn state clear of the instrument bore (22) to an engagement state sealably engaging an instrument in the instrument bore (22) for sealing the instrument bore (22). A (Continued)

Figure 1:
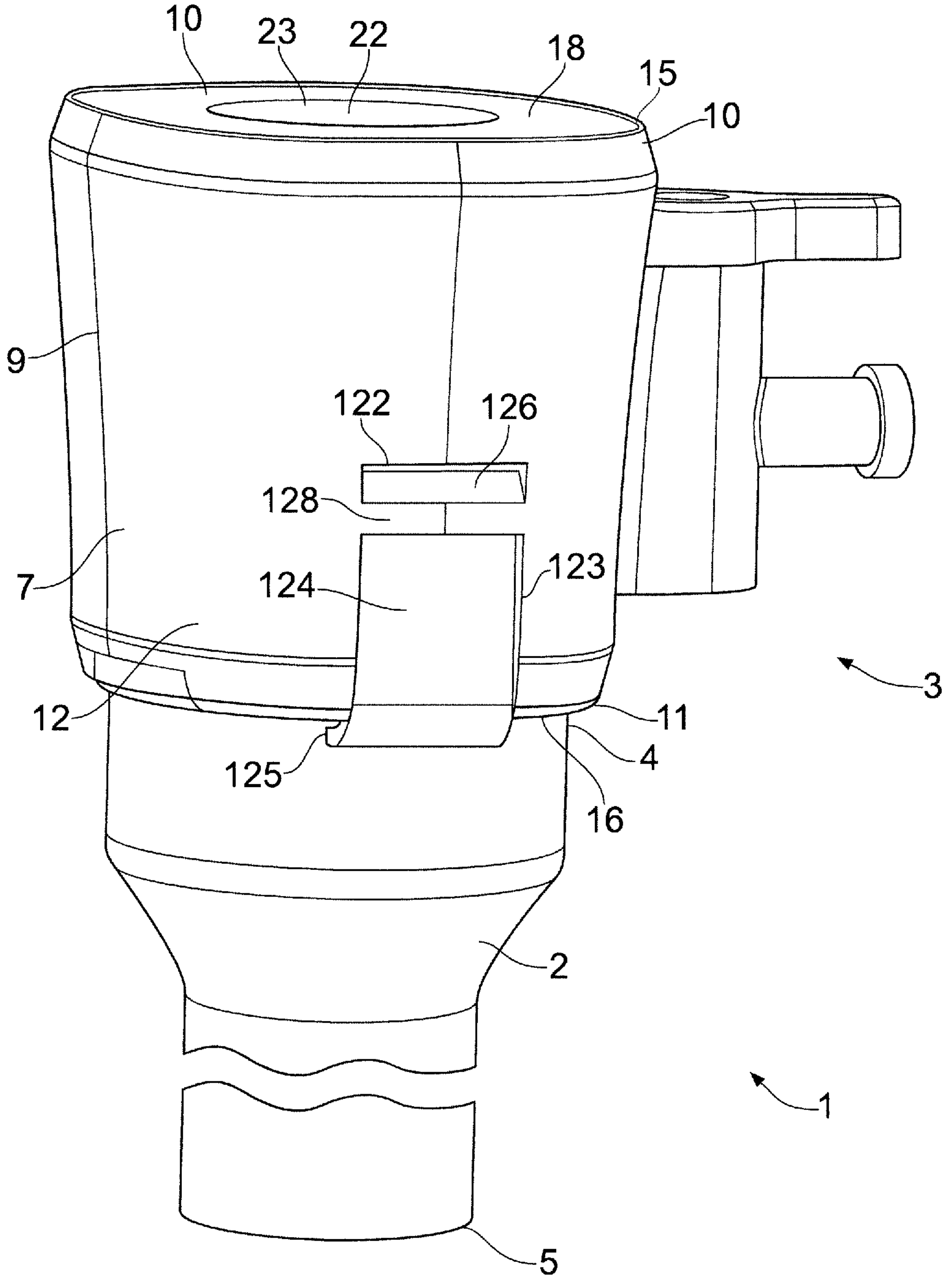

detecting probe (34) pivotal about a primary pivot axis (35) is urgeable distally from a first state to a second state by the distal end of an instrument passing distally through the instrument bore (22). A drive transmission (74,108) transmits drive from the detecting probe (34) to the proximal and distal valves (40,28), so that as the detecting probe (34) is urged from a first state to a second state the distal valve (28) is urged into the open state and the proximal valve (40) is simultaneously urged from the withdrawn state to the engagement state to minimise leakage of gas proximally through the instrument bore (22) and to minimise contact of an instrument with the proximal and distal valves (40,28).

20 Claims, 30 Drawing Sheets

(52) U.S. Cl.
CPC ............... *A61B 2017/00022* (2013.01); *A61B 2017/00477* (2013.01); *A61B 2017/00862* (2013.01); *A61B 2017/3441* (2013.01); *A61B 2017/3464* (2013.01); *A61B 2217/005* (2013.01)

(56) References Cited

U.S. PATENT DOCUMENTS 5,458,640 A 10/1995 Gerrone
5,492,304 A * 2/1996 Smith ................ A61B 17/3462 251/342
5,657,963 A * 8/1997 Hinchliffe ............. A61M 39/06 604/167.01
5,788,676 A 8/1998 Yoon
2008/0294114 A1* 11/2008 Smith ................ A61B 17/3462 604/167.06
2009/0177162 A1 7/2009 Heinrich
2017/0055942 A1 3/2017 Tsuruta
2017/0215920 A1 8/2017 Farin et al.
2022/0047302 A1 2/2022 O'Dea et al.

FOREIGN PATENT DOCUMENTS

JP 05-344949 A 12/1993
WO 2020/105022 A2 5/2020
WO 2021/240492 A1 12/2021

OTHER PUBLICATIONS

International Search Report for PCT/IE2021/000010 dated Nov. 19, 2021 [PCT/ISA/210].
International Search Report for PCT/IE2019/000010 dated May 26, 2020 [PCT/ISA/210].
U.S. Appl. No. 17/927,588, filed Nov. 23, 2022, John O'Dea, et al.

* cited by examiner 3
10
128
123
122
11
9
7

9
11
16
28
29

10
7
9
11

40
22
18
23
122
128
123
11

45
42
56
58
40
62
41
95
C
C
44
93
55
84
83
87
62
110
H
78
81
85
80
82
63
64
102
28

E
D
F
29

42
48
60
23
60
20
41
47
53
49
48
50
64
54
98
34
67
35
97
87
37
H
78
95
B
19
20
30
102
22
28
21
A
69
24
29

42
23
60
60
22
41
64
68
78
95
14
98
34
12
97
37
67
113
63
81
112
B
69
102
19
110
114
115
73
A
21
28
29
100

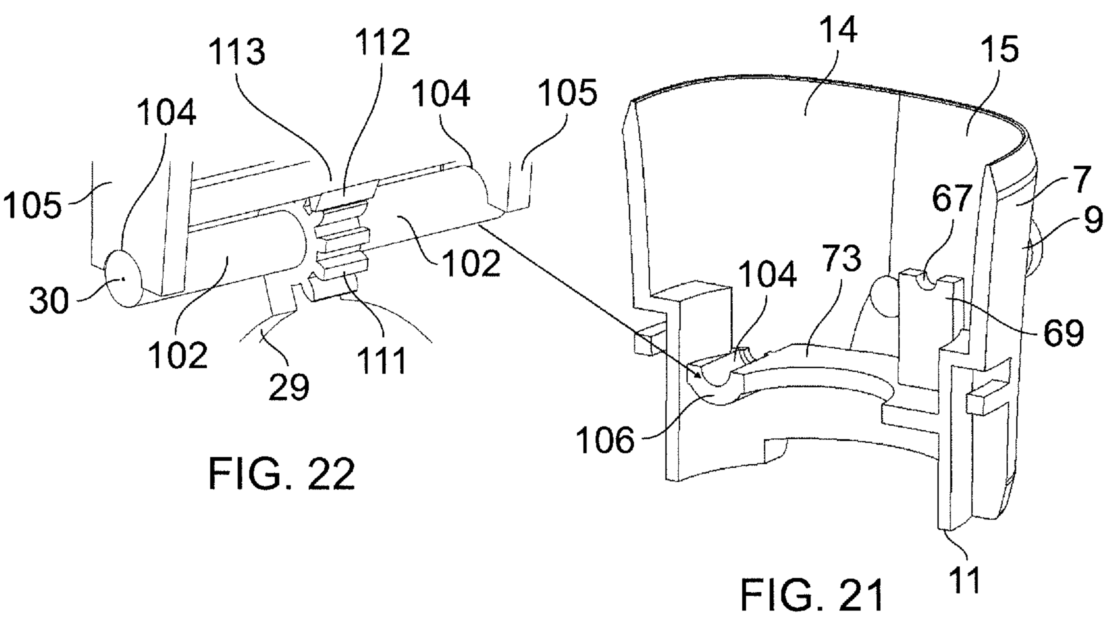
FIG. 22
FIG. 21
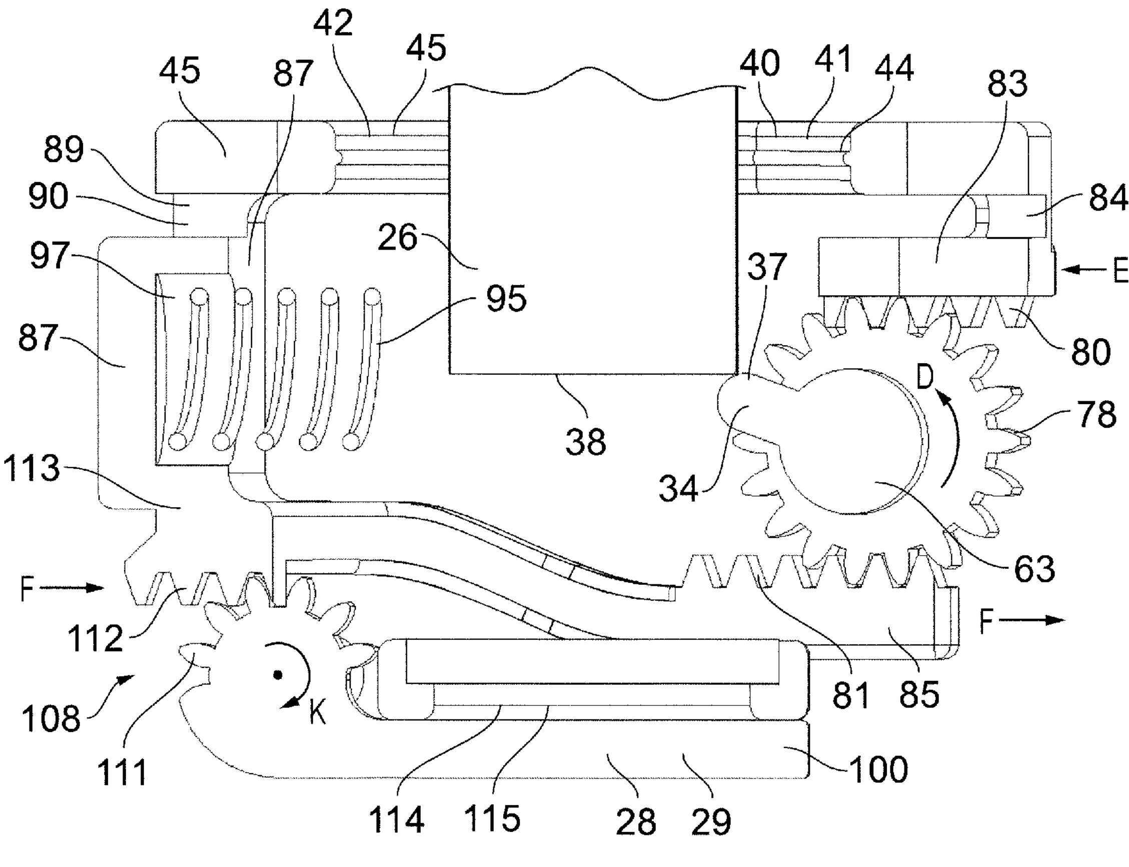
FIG. 24

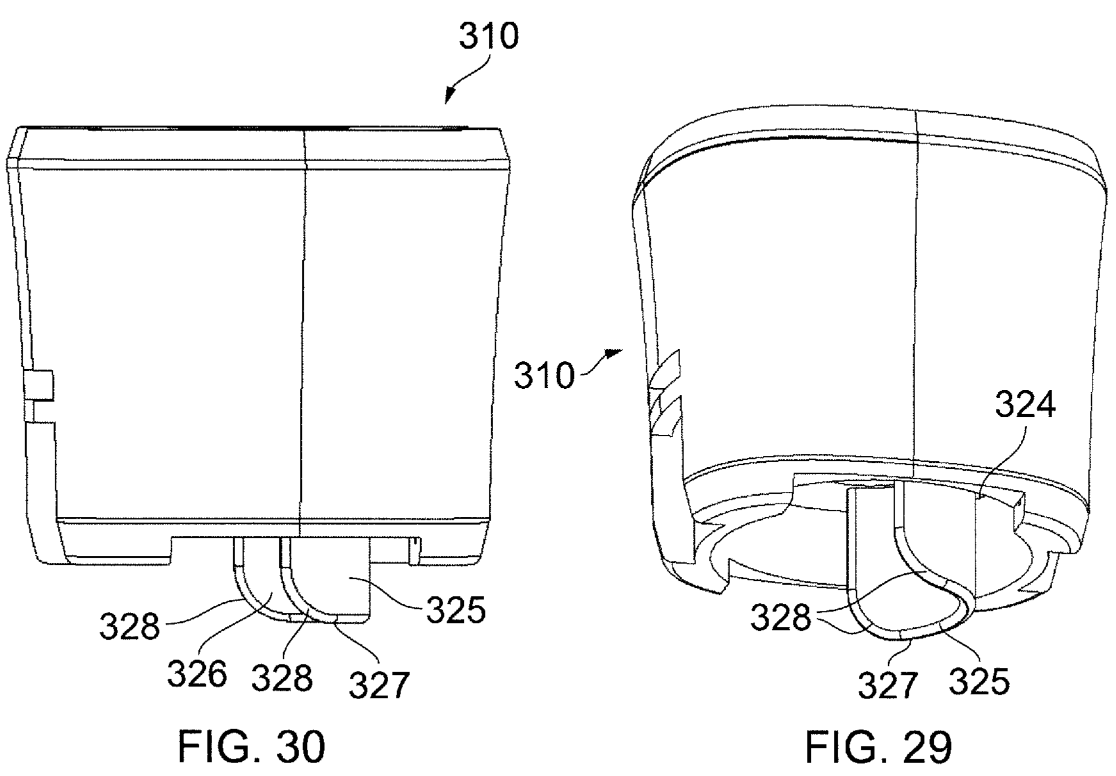
FIG. 30
FIG. 29
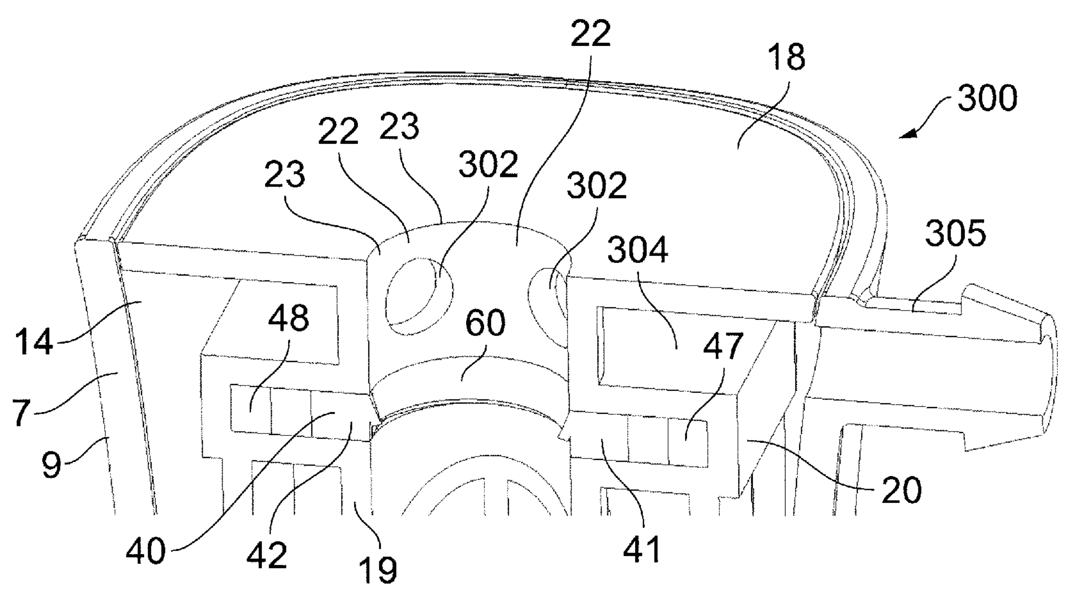
FIG. 28

VALVE MECHANISM

CROSS REFERENCE TO RELATED APPLICATIONS

This application is a National Stage of International Application No. PCT/IE2021/000011 filed May 27, 2021, claiming priority based on Irish Patent Application Nos. S2020/0116 filed May 27, 2020 and S2020/0117 filed May 27, 2020.

The present invention relates to a valve mechanism, and in particular, but not limited to a valve mechanism for securing to the proximal end of a trocar or a trocar cannula to minimise leakage of insufflating and other gases from a cavity in a subject being insufflated, and into which the trocar or the trocar cannula extends. The invention also relates to an assembly comprising a trocar or a trocar cannula and the valve mechanism.

Throughout this specification, the term "trocar cannula" is used to mean a cannula portion of the trocar having an instrument bore extending therethrough for accommodating instruments into a cavity or vessel of a subject into which the trocar cannula has been inserted prior to a laparoscopic investigative or surgical procedure, or other minimal invasive investigative and surgical procedures. Such a trocar cannula may or may not comprise an access valve adjacent the proximal end thereof, which is urgeable from a closed state to an open state by an instrument being inserted therethrough. The term "trocar" is used to mean an assembly of a trocar cannula and a proximal trocar housing secured releasably or otherwise to the proximal end of the trocar cannula. The term "proximal trocar housing" is used to mean a housing which is secured to the proximal end of a trocar cannula, and comprises an instrument bore for accommodating instruments therethrough to the instrument bore of the trocar cannula, and may also include a valving system in the instrument bore for minimising loss of insufflating gases. One or more ports may also be provided in the proximal trocar housing for supplying insufflating gas, as well as liquids and the like through the trocar to the cavity or vessel of a subject.

Trocars are used in laparoscopic surgery and other minimal invasive investigative and surgical procedures both on humans and animals. In the carrying out of such procedures in, for example, the abdominal cavity, one or more trocars are extended through the abdominal wall into the abdominal cavity in order to accommodate surgical instruments and other instruments into the abdominal cavity. In order to provide an operating field for a surgeon in the abdominal cavity, the abdominal cavity is insufflated by a suitable insufflator, which pumps air or an inert gas, for example, carbon dioxide into the abdominal cavity through the trocar or other suitable instrument.

Such trocars comprise a trocar cannula and a proximal trocar housing for accommodating surgical instruments into the trocar cannula and for attaching conduits thereto for supplying insufflating gas and other gases or liquids, which are delivered into the cavity, in which the procedure is being carried out, through the trocar. The trocar cannula is of tubular construction having an elongated instrument bore extending therethrough in order to accommodate instruments as well as a laparoscope and/or an endoscope into the abdominal cavity.

It is important that the instrument bore extending through a trocar incorporates a sealing system for minimising the escape of insufflating gas from the abdominal cavity. Such sealing systems for sealing an instrument bore extending through a trocar, in general comprise a valve or an annular seal located in the instrument bore and extending around and into the instrument bore to bear on the instrument in the instrument bore in order to minimise the passage of insufflating gas between the seal and the instrument. Such seals or valves may be located in the instrument bore of the proximal trocar housing or in the trocar cannula or in both, and when located in the instrument bore of the trocar cannula, are in general, located adjacent the proximal end thereof. However, various problems arise with such valves and seals.

Firstly, the ability of such valves and seals to form a seal with the instrument, laparoscope or endoscope being inserted through the instrument bore of the trocar is sometimes inadequate, thus allowing uncontrolled escape of insufflating gas from the abdominal cavity while the instrument is located in the trocar.

Secondly, such seals bear on the instrument, and as the instrument is being withdrawn from the abdominal cavity, body fluids, tissue and other matter on the instruments may be deposited on the seal. This results in a serious problem. Where a laparoscope or endoscope is to be entered into the abdominal cavity through the instrument bore of a trocar after an instrument has been withdrawn from the abdominal cavity through the instrument bore, and on being withdrawn deposited body fluids, tissue or other matter on the seal in the instrument bore, as the laparoscope or endoscope is being inserted through the instrument bore of the trocar, the deposited matter on the seal transfers to the lens of the laparoscope or endoscope, which is located adjacent the leading end of the laparoscope or endoscope, thus occluding the lens thereof.

Additionally, the leakage and escape of insufflating gas from the abdominal cavity or any other cavity of a subject being insufflated through a trocar causes two problems. Firstly, the loss of the insufflating gas, which in the case of an inert gas such as carbon dioxide, is wasteful. Secondly, and of considerably more importance, such escaping insufflating gas has been found to carry organisms, such as pathogens, viruses and infections from the cavity of a subject being insufflated. These organisms are dispersed directly into an operating theatre from the trocar, and can thus result in healthcare professionals carrying out and participating in a procedure being infected themselves. This is a particularly serious problem in cases where a subject is infected with a virus for which there is no known cure.

There is therefore a need to address at least one of these problems.

The present invention is directed towards providing a valve mechanism for addressing at least one of such problems, and the invention is also directed towards an assembly comprising a trocar or a trocar cannula and the valve mechanism.

According to the invention there is provided a valve mechanism for a trocar or a trocar cannula, the valve mechanism comprising a housing having an instrument bore extending therethrough from a proximal end to a distal end and defining a longitudinally extending main central axis, a detecting means located in the housing configured to detect an instrument in or passing through the instrument bore, and a proximal valve located in the housing operable from a withdrawn state to an engagement state engaging the instrument in the instrument bore to form a seal with the instrument for minimising leakage of gas past the proximal valve in response to the detecting means detecting an instrument passing distally in the instrument bore.

In one embodiment of the invention the detecting means is configured to extend into the instrument bore, and preferably, is configured for engagement with an instrument in the instrument bore.

In one embodiment of the invention the detecting means is moveably mounted in the housing, and preferably, is moveable in the instrument bore from a first state to a second state in response to movement of the instrument distally in the instrument bore.

Preferably, the detecting means is moveable distally from the first state to the second state, and advantageously, the detecting means is moveable distally in the instrument bore from the first state to the second state.

In another embodiment of the invention the detecting means is configured to be urgeable from the first state to the second state by movement of an instrument distally in the instrument bore, and preferably, by movement of a distal end of an instrument distally in the instrument bore. Preferably, the detecting means is urgeable by an instrument moving distally in the instrument bore, and advantageously the detecting means is configured to engage a distal end of an instrument in the instrument bore.

In one embodiment of the invention the detecting means is pivotally mounted in the housing, and preferably, the detecting means is pivotally mounted about a primary pivot axis.

In one embodiment of the invention the primary pivot axis extends transversely relative to the main central axis defined by the instrument bore.

In another embodiment of the invention the detecting means extends radially relative to the primary pivot axis.

In one embodiment of the invention the detecting means is carried on a pivotally mounted primary pivot shaft. Preferably, the primary pivot shaft defines the primary pivot axis, and the primary pivot shaft is pivotal about the primary pivot axis. Advantageously, the detecting means extends radially from the primary pivot shaft, and the primary pivot shaft is driven by movement of the detecting means from the first state to the second state.

In another embodiment of the invention the detecting means terminates in a distal, instrument engaging element.

In a further embodiment of the invention the detecting means comprises a detecting probe, and preferably, an elongated detecting probe extending from the housing into the instrument bore and terminating adjacent a distal end thereof in the distal, instrument engaging element. Advantageously, the detecting means comprises an elongated detecting member.

In one embodiment of the invention the proximal valve is urgeable from the withdrawn state to the engagement state in response to movement of the detecting means from the first state to the second state.

In another embodiment of the invention a first transmission means is provided for transmitting movement of the detecting means from the first state to the second state to movement of the proximal valve from the withdrawn state to the engagement state.

In one embodiment of the invention the first transmission means comprises a linkage mechanism, and advantageously, the linkage mechanism is coupled between the detecting means and the proximal valve.

In an alternative embodiment of the invention the first transmission means comprises a first drive transmission means, and advantageously, the first drive transmission means comprises a first transmission element configured to derive drive from motion from the detecting means as the detecting means moves from the first state to the second state.

In another embodiment of the invention the first drive transmission means comprises at least one second transmission element configured to urge the proximal valve from the withdrawn state to the engagement state.

In another embodiment of the invention the at least one second transmission element is configured to urge the proximal valve from the withdrawn state to the engagement state as the detecting means moves from the first state to the second state.

In another embodiment of the invention the first drive transmission means is configured to derive the drive from the motion of the detecting means as the detecting means moves from the first state to the second state.

In another embodiment of the invention the at least one second transmission element is co-operable with the first transmission element for transmitting the derived drive from the detecting means to the proximal valve.

Preferably, the at least one second transmission element is operably engageable with the first transmission element.

Advantageously, the first transmission element is driven by the movement of the detecting means from the first state to the second state.

In another embodiment of the invention the first transmission element is rotatable about a first drive transmission axis, and preferably, the first drive transmission axis coincides with the primary pivot axis.

In another embodiment of the invention the first transmission element is mounted on the primary pivot shaft, and preferably, the first transmission element is mounted fast on the primary pivot shaft.

Preferably, the primary pivot shaft is pivotally mounted in the housing.

Preferably, the primary pivot shaft is driven by movement of the detecting means from the first state to the second state, and advantageously, between the first state and the second state.

In another embodiment of the invention the first transmission element comprises a first gear element, and preferably, a first gear wheel.

In one embodiment of the invention the second transmission element comprises at least one gear rack operably coupled to the proximal valve.

In another embodiment of the invention the at least one gear rack of the second transmission element is operably engageable with the first gear wheel.

In another embodiment of the invention the proximal valve is configured to sealably engage the housing, and advantageously, the proximal valve is configured to sealably engage the housing in the engagement state.

In another embodiment of the invention the proximal valve comprises a pair of proximal valve elements, and preferably, the proximal valve elements are urgeable from the withdrawn state to the engagement state for engaging an instrument in the instrument bore.

In another embodiment of the invention the proximal valve elements cooperate with each other in the engagement state for forming a seal with an instrument in the instrument bore.

In another embodiment of the invention the proximal valve elements are moveable between the withdrawn state and the engagement state with rectilinear motion.

In one embodiment of the invention the proximal valve elements are moveable between the withdrawn state and the engagement state transversely relative to the main central axis, and advantageously, the proximal valve elements are moveable towards each other from the withdrawn state to the engagement state.

In another embodiment of the invention the proximal valve elements are located on respective opposite sides of the main central axis.

In another embodiment of the invention the at least one second transmission element is configured to impart rectilinear motion to the proximal valve elements, and advantageously, the at least one second transmission element comprises a first one of the gear racks for urging one of the proximal valve elements from the withdrawn state to the engagement state, and a second one of the gear racks for urging the other one of the proximal valve elements from the withdrawn state to the engagement state, and preferably, the first and second gear racks are moveable with rectilinear motion.

Preferably, the first and second gear racks are moveable with the rectilinear motion in a direction transversely of the main central axis, and preferably, the first and second gear racks are moveable with the rectilinear motion transversely of the primary pivot axis.

Advantageously, the first and second gear racks are moveable with the rectilinear motion in respective opposite directions to each other.

In one embodiment of the invention the first and second gear racks are driven by the first gear wheel, and preferably, the first and second gear racks are driven by the first gear wheel on respective opposite sides of the first drive transmission axis.

In one embodiment of the invention each proximal valve element terminates in a first sealing means configured to sealably engage an instrument in the instrument bore.

In another embodiment of the invention the first sealing means of each proximal valve element comprises a central sealing portion configured to engage an instrument in the instrument bore.

In another embodiment of the invention the central sealing portion of the first sealing means of each proximal valve element defines a portion of the transverse cross-section of an instrument in the instrument bore.

Preferably, the central sealing portions of the first sealing means of the respective proximal valve elements cooperate to define the transverse cross-section of an instrument in the instrument bore.

In another embodiment of the invention the central sealing portion of the first sealing means of each proximal valve element is of arcuate shape, and preferably, the central sealing portion of the first sealing means of each proximal valve element extends approximately 180° around the main central axis.

Preferably, the first sealing means of each proximal valve element comprises a pair of side sealing portions extending sidewardly from the central sealing portion of the first sealing means, and advantageously, the side sealing portions of the first sealing means of each proximal valve element cooperate with the corresponding side sealing portions of the other one of the proximal valve elements to form a seal therebetween.

In one embodiment of the invention the respective proximal valve elements sealably engage the housing, and preferably, the first sealing means of the respective proximal valve element sealably engage the housing in the engagement state of the proximal valve.

In another embodiment of the invention a guide means is provided for guiding the proximal valve between the withdrawn state and the engagement state.

Preferably, an urging means is provided for urging the proximal valve into the withdrawn state. Advantageously, the urging means comprises a resilient urging means, and preferably, the urging means comprises a spring acting between the proximal valve and the housing. Ideally, the spring comprises a compression spring.

In one embodiment of the invention the urging means is responsive to a distal end of an instrument in the instrument bore passing distally past the detecting means for urging the proximal valve from the engagement state to the withdrawn state.

In another embodiment of the invention the proximal valve is located proximally from the detecting means, and advantageously, the proximal valve is spaced apart proximally from the detecting means.

In one embodiment of the invention a distal valve is located distally of the detecting means, and preferably, the distal valve is spaced apart distally from the detecting means. Advantageously, the distal valve is operable between a closed state closing the instrument bore, and an open state permitting passage of an instrument through the instrument bore.

In another embodiment of the invention the distal valve is operable from the closed state to the open state in response to the detecting means detecting an instrument passing distally in the instrument bore.

In one embodiment of the invention the distal valve is operable from the closed state to the open state in response to movement of the detecting means from the first state to the second state.

Preferably, the distal valve is pivotal about a distal valve pivot axis, and preferably, the distal valve pivot axis extends transversely of the main central axis defined by the instrument bore.

Advantageously, the distal valve pivot axis extends parallel to the primary pivot axis, and in one embodiment of the invention the distal valve pivot axis is located on the opposite side of the main central axis to that on which the primary pivot axis is located.

In another embodiment of the invention the distal valve is carried on a distal valve pivot shaft, and preferably, the distal valve pivot shaft defines the distal valve pivot axis.

Advantageously, the distal valve pivot shaft is pivotally mounted in the housing.

In another embodiment of the invention a second drive transmission means is provided for transmitting movement of the detecting means from the first state to the second state to movement of the distal valve from the closed state to the open state.

Preferably, the second drive transmission means comprises a third transmission element configured to derive drive from the first drive transmission means and configured for urging the distal valve from the closed state to the open state.

Advantageously, the third transmission element is cooperable with the first drive transmission means for deriving drive from the first drive transmission means. Preferably, the third transmission element comprises a third gear element, and preferably, a third gear rack, and advantageously, the third gear rack is urgeable by the first drive transmission means for urging the distal valve from the closed state to the open state in response to the detecting means being urged from the first state to the second state, and preferably, the third gear rack is urgeable by the second gear rack of the first drive transmission means for urging the distal valve from the closed state to the open state in response to the detecting means being urged from the first state to the second state.

In one embodiment of the invention the second drive transmission means comprises a fourth transmission element co-operable with the distal valve for urging the distal valve from the closed state to the open state. Preferably, the fourth transmission element is co-operable with the third transmission element for transferring drive from the third transmission element to the distal valve. Advantageously, the fourth transmission element comprises a fourth gear element.

In one embodiment of the invention the fourth gear element is rotatable about a second drive transmission axis. Preferably, the second drive transmission axis of the fourth gear element coincides with the distal valve pivot axis.

Preferably, the fourth gear element is mounted on the distal valve pivot shaft of the distal valve, and advantageously, is mounted fast on the distal valve pivot shaft of the distal valve.

In one embodiment of the invention the third gear rack is moveable with rectilinear motion, and preferably, is moveable with the rectilinear motion parallel to the rectilinear motion of the second gear rack.

In another embodiment of the invention the distal valve is located adjacent the distal end of the instrument bore, and preferably, is moveable from the closed state to the open state in a generally distal direction.

In one embodiment of the invention the housing terminates in a valve seat adjacent the distal end of the instrument bore, and advantageously, the distal valve is sealably engageable with the valve seat in the closed state.

In one embodiment of the invention a second sealing means is provided for forming a seal between the valve seat and the distal valve.

In one embodiment of the invention the second sealing means is provided on the distal valve, and in an alternative embodiment of the invention the second sealing means is provided on the valve seat.

Preferably, the second sealing means is located on and extends around the valve seat.

In another embodiment of the invention the distal valve comprises a valve plate member, which preferably extends substantially radially from and parallel with the distal valve pivot axis.

In one embodiment of the invention the distal valve comprises a pair of the valve plate members cooperable with each other for closing the instrument bore, each valve plate member extending substantially radially from a corresponding one of a pair of the distal valve pivot axes, and each valve plate member being operable from the closed state to the open state in response to the detecting means detecting an instrument passing distally in the instrument bore.

In another embodiment of the invention the valve plate members of the distal valve are operable from the closed state to the open state by respective ones of the second drive means.

In one embodiment of the invention the valve plate members of the distal valve are pivotal about respective ones of the distal valve pivot axes, and the distal pivot axes of the respective valve plate members of the distal valve are located on respective opposite sides of the main central axis.

In one embodiment of the invention the urging means is adapted to urge the distal valve from the open state to the closed state in response to a distal end of an instrument in the instrument bore passing distally past the detecting means.

In one embodiment of the invention at least one collecting port is located adjacent the instrument bore, the at least one collecting port being configured for communicating with a vacuum system for applying a vacuum to the collecting port for collecting insufflating gas and other gases passing in a proximal direction in or from the instrument bore.

Preferably, the at least one collecting port is located adjacent the proximal end of the instrument bore, and advantageously, the at least one collecting port is formed in the housing defining the instrument bore, and preferably, the at least one collecting port is located proximally of the proximal valve.

In another embodiment of the invention a plurality of collecting ports are provided, and advantageously, the collecting ports are spaced apart circumferentially around the instrument bore.

In one embodiment of the invention an operating means adapted to operate an access valve in the trocar or the trocar cannula from a closed state to an open state is provided.

In another embodiment of the invention the operating means comprises an operating member.

In another embodiment of the invention the operating means comprises a tubular member. Preferably, the tubular member is coaxial with the instrument bore.

In another embodiment of the invention the operating means comprises a passive operating means. Preferably, the passive operating means comprises a static operating means. Advantageously, the passive operating means comprises a static operating member extending distally from the valve mechanism, and being engageable with the access valve in the trocar or the trocar cannula as the valve mechanism is being engaged with the trocar or the trocar cannula.

In another embodiment of the invention the operating means comprises an active operating means.

Preferably, the operating means is urgeable distally from a disengaged state disengaged from the access valve of the trocar or the trocar cannula to an engagement state for engaging the access valve to operate the access valve from the closed state to the open state thereof.

Advantageously, the operating means is urgeable distally from the disengaged state to the engagement state in response to the detecting means detecting an instrument in or passing through the instrument bore.

In one embodiment of the invention the operating means is urgeable from the disengaged state to the engagement state in response to the detecting means being urged from the first state to the second state.

Preferably, a third transmission means is provided for transmitting movement of the detecting means from the first state to the second state into movement of the operating means from the disengaged state to the engagement state.

In another embodiment of the invention the urging means is adapted to urge the operating means from the engagement state to the disengaged state.

In one embodiment of the invention the operating means is located in the instrument bore, and is urgeable distally in the instrument bore between the disengaged state and the engagement state. Alternatively, the operating means is located externally of the instrument bore.

In one embodiment of the invention the distal valve is configured as the active operating means.

In another embodiment of the invention the distal valve is adapted to operate the access valve of the trocar or the trocar cannula from the closed state to the open state as the distal valve is being urged from the closed state to the open state.

In another embodiment of the invention the valve mechanism is configured for mounting on a trocar or a trocar cannula, and preferably, for mounting on the proximal end of the trocar or the trocar cannula, and advantageously, the valve mechanism is configured for mounting on the trocar or the trocar cannula with the instrument bore defined by the housing of the valve mechanism aligned with an instrument bore of the trocar or the trocar cannula.

In another embodiment of the invention the housing of the valve mechanism is configured for sealable engaging the trocar or the trocar cannula, and advantageously, the housing of the valve mechanism defines a trocar engagement opening for engaging the trocar or the trocar cannula.

Preferably, a third sealing means is provided for sealing the housing of the valve mechanism with the trocar or the trocar cannula, and advantageously, the first sealing means extends around the trocar engaging opening.

Preferably, a securing means is provided for securing the valve mechanism to the trocar or the trocar cannula, and advantageously, the securing means comprises a releasable securing means.

The invention also provides an assembly comprising a trocar or a trocar cannula and the valve mechanism according to the invention mounted on the trocar or the trocar cannula, and preferably, the valve mechanism is mounted on the trocar or the trocar cannula adjacent the proximal end thereof.

The advantages of the invention are many. A particularly important advantage of the invention is that the leakage of insufflating gas and other gases from a cavity of a subject being insufflated which would otherwise leak proximally through a trocar is eliminated, and if not fully eliminated, is eliminated to the extend that such leakage is negligible. Furthermore, leakage of insufflating gases which would otherwise leak proximally through the instrument bore of a trocar during insertion of an instrument, for example, a laparoscope or an endoscope or surgical instruments, is substantially eliminated if not totally eliminated during insertion and withdrawal of the instrument into and from the trocar. These advantages are achieved largely by virtue of the fact that the valve mechanism is provided with a distal valve adjacent the end of the instrument bore thereof and a proximal valve adjacent the proximal end of the instrument bore.

By virtue of the fact that the first and second proximal valve members are configured to operate from the withdrawn state to the engagement state simultaneously as the distal valve is being operated from the closed state to the open state, as an instrument is being entered into the instrument bore, the first and second proximal valve members of the proximal valve are urged to sealably engage the instrument in the bore, as the distal valve is being operated from the closed state to the open state, thereby minimising and virtually totally eliminating any leakage of gases proximally through the instrument bore of the valve mechanism, and in turn proximally from the instrument bore.

A further advantage of the invention is that there is little or no danger of the distal end of an instrument being contaminated by any biological material or other matter which may have been deposited on either the distal valve or the proximal valve by a previous instrument as that previous instrument was being withdrawn from the cavity being insufflated through the trocar and through the valve mechanism. This is a significant advantage, particularly, when the instrument being introduced distally through the valve mechanism comprises a laparoscope or an endoscope. Any contamination of the distal end of a laparoscope or an endoscope resulting from contact of the distal end of such a laparoscope or an endoscope with such matter deposited on either of the proximal or distal valves could result in the lens thereof which is located adjacent the distal end of a laparoscope or an endoscope being occluded by such matter, thereby preventing image capturing by an imaging device through the lens. This advantage is achieved by virtue of the fact that the distal valve is located distally of the detecting means, and the proximal valve is located proximally of the detecting means, and when there is no instrument in the instrument bore of the valve mechanism, the proximal valve is in the withdrawn state or open state and the distal valve is in the closed state. Therefore, the instrument can be entered into the instrument bore of the valve mechanism at the proximal end thereof without any danger of contact of the distal end of the instrument with the proximal valve. It is only when the distal end of the instrument has passed the proximal valve, and is detected by the detecting means, that the proximal valve is urged from the withdrawn state to the engagement state. Additionally, since the detecting means is located proximally of the distal valve, the distal valve is operated into the open state prior to the distal end of the instrument reaching the distal valve. Thereby, the distal end of the instrument passes from the instrument bore of the valve mechanism unimpeded by the distal valve into the instrument bore of the trocar cannula thereby avoiding any contamination of the distal end of the instrument.

Conversely, on withdrawal of the instrument from a cavity being insufflated through the trocar cannula, and in turn through the valve mechanism, the distal valve is retained in the open state until the distal end of the instrument is detected by the detecting means so that the distal end of the instrument is clear of the distal valve prior to the distal valve being urged from the closed state to the open state. Additionally, as the distal end of the instrument is detected passing distally past the detecting means, the first and second proximal valve members of the proximal valve are urged from the engagement state to the withdrawn state prior to the distal end of the instrument reaching the proximal valve. Thereby, there is little or no danger of any biological or other matter which may have adhered to the instrument, while in the cavity of the subject, being deposited on the distal valve during withdrawal of the instrument. Furthermore, since in general, any contamination of an instrument with biological or other matter while in a cavity of a subject occurs adjacent the distal end of the instrument, there is also littler or no danger of any such matter being transferred from the instrument to the proximal valve during withdrawal of the instrument, since the proximal valve will have been urged from the engagement state to the withdrawn state, prior to the distal end of the instrument reaching the proximal valve.

All the above advantages are also achieved by the valve mechanism according to the invention, even when the distal valve is omitted from the valve mechanism, but when the valve mechanism includes an operating means, and in particular an active operating means for operating an access valve in a trocar or a trocar cannula adjacent the distal end thereof from a closed state to an open state. By virtue of the fact that the active operating means is configured to operate the access valve of the trocar or trocar cannula from the closed state to the open state as the detecting means is urged distally from the first state to the second state, and simultaneously the proximal valve is urged from the withdrawn state to the engagement state, the combination of the access valve in the trocar or trocar cannula with the active operating means effectively results in the access valve of the trocar or trocar cannula taking the place of the distal valve of the valve mechanism.

Figures 2, 3, 4, 5:
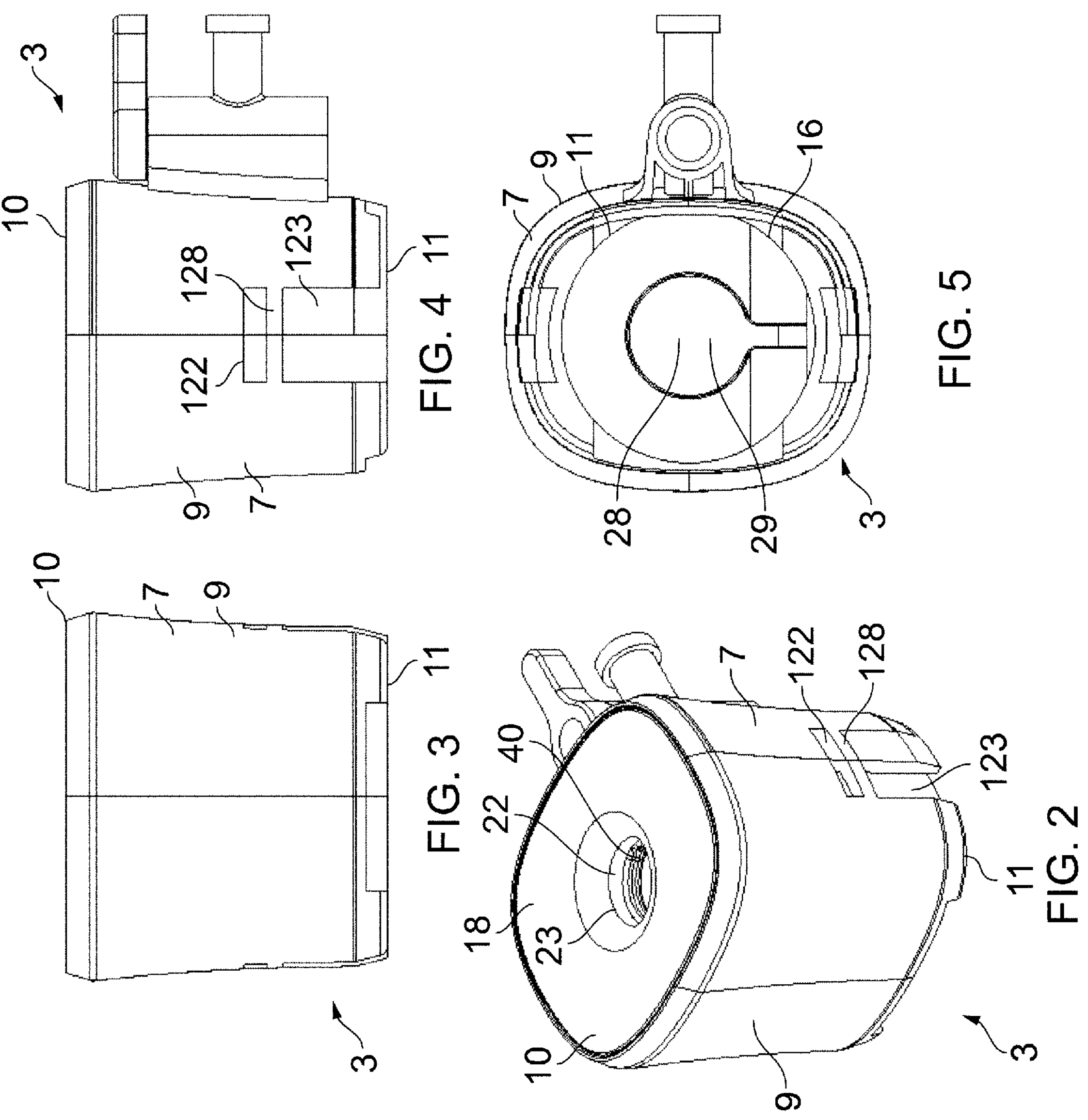
Figure 6:
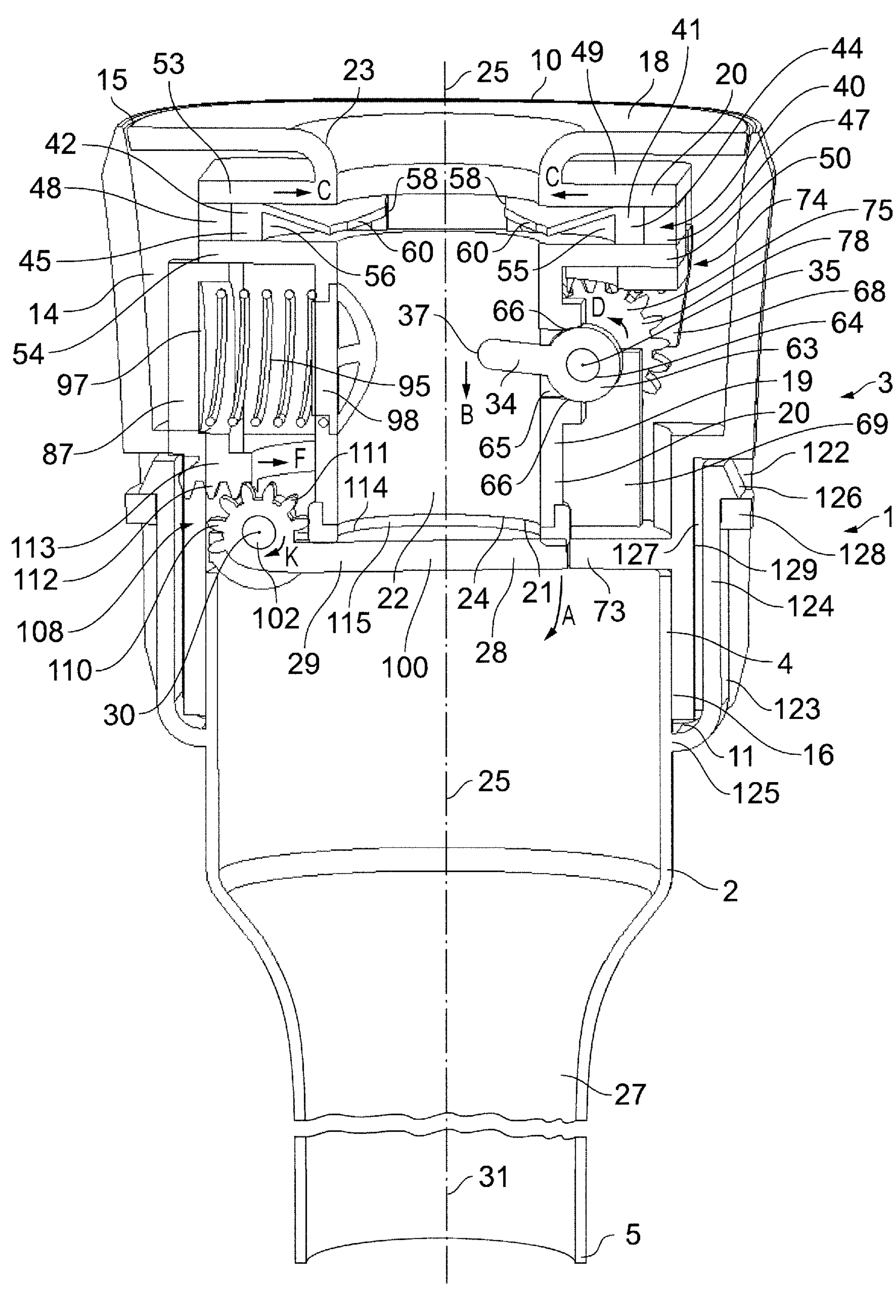
Figures 7, 8:
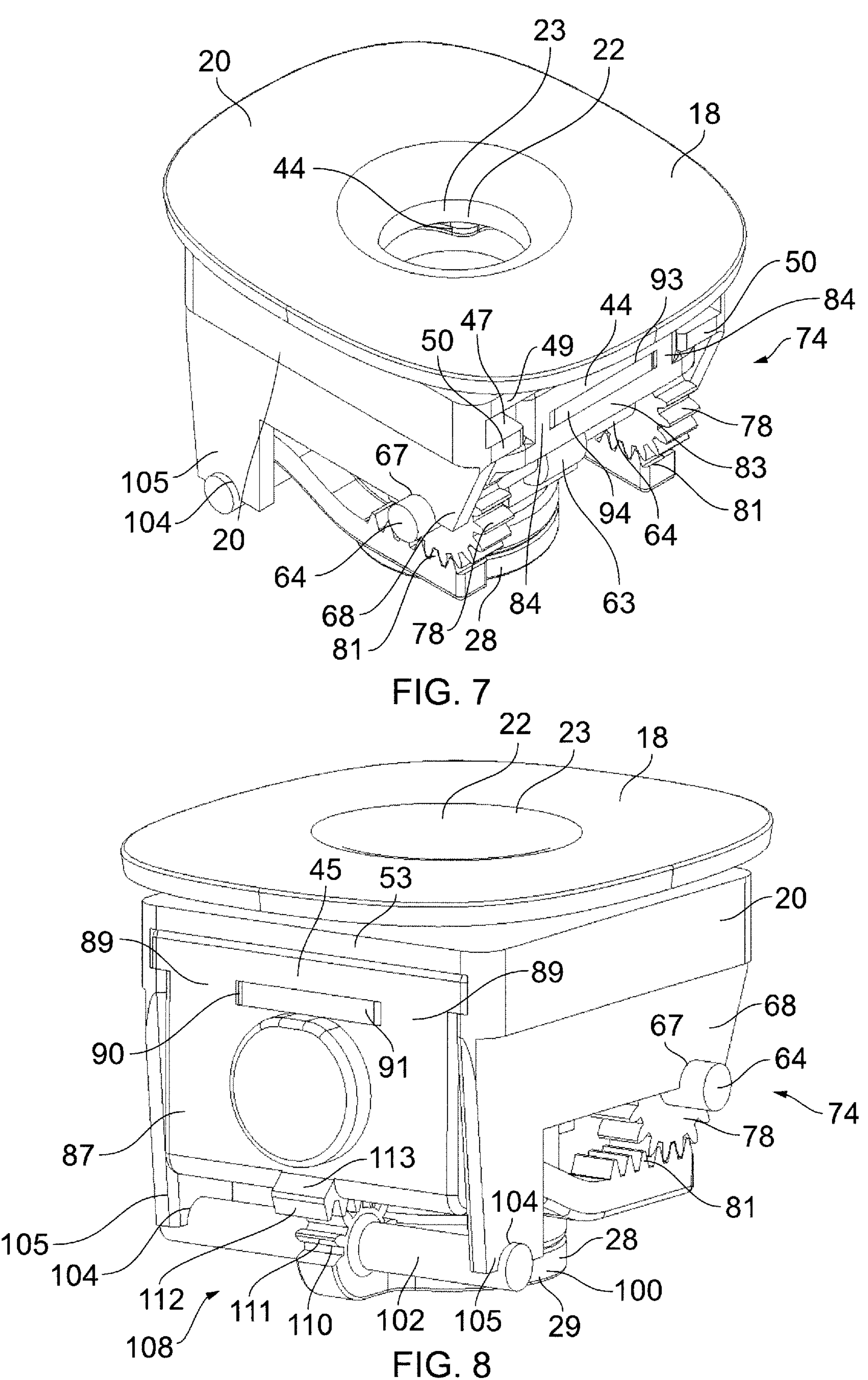
Figures 9, 12:
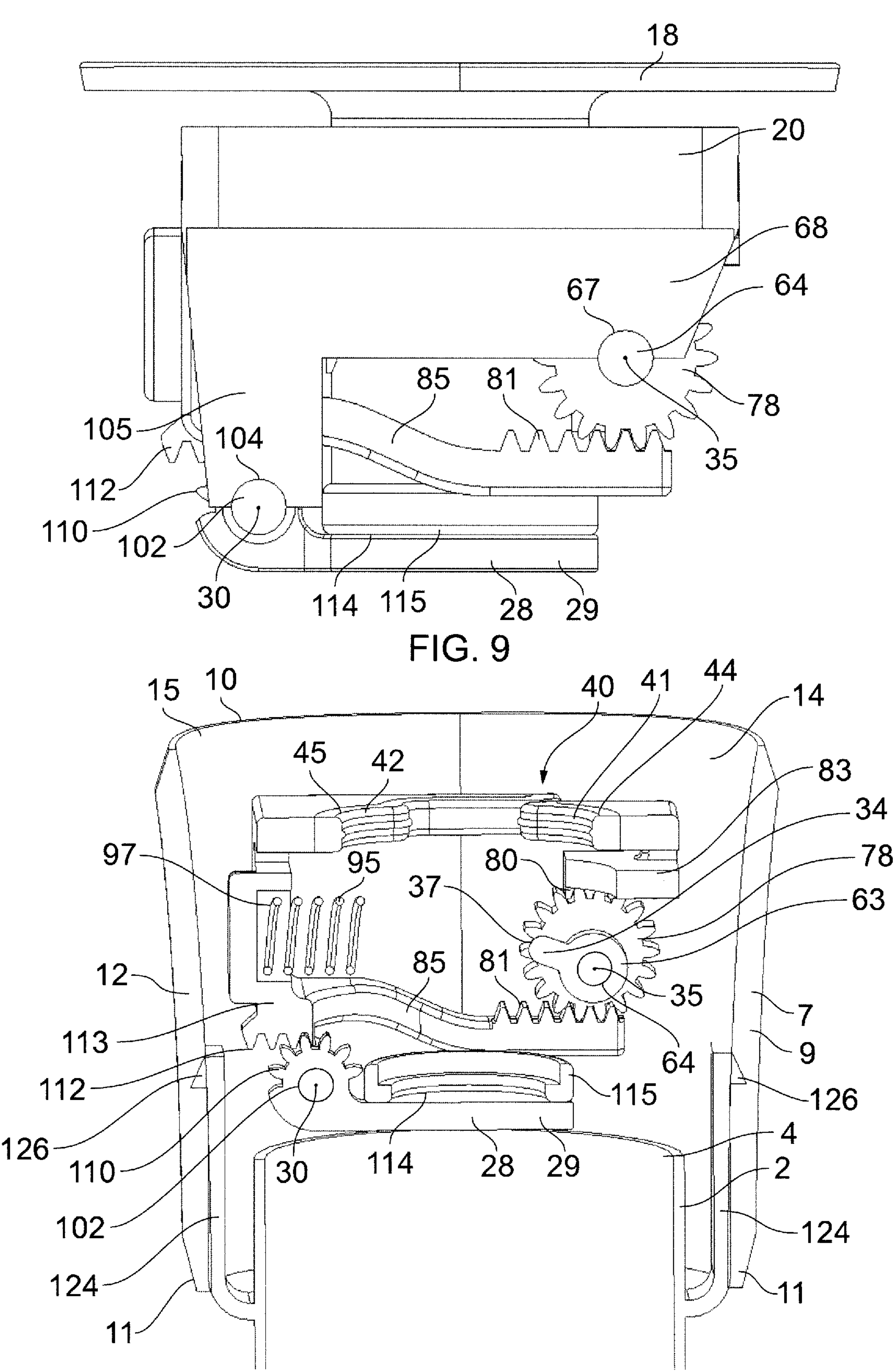
Figures 10, 11:
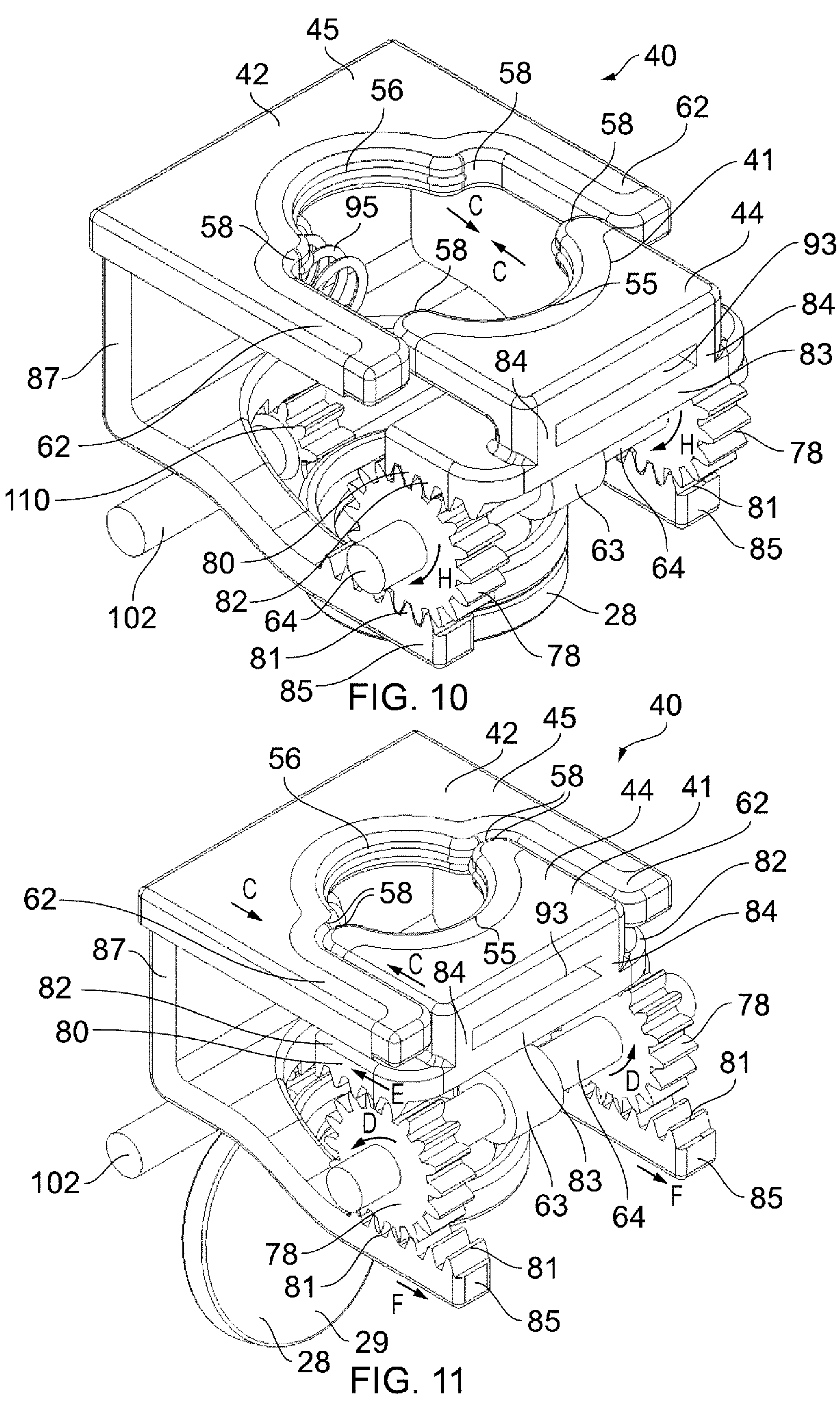
Figures 13, 14:
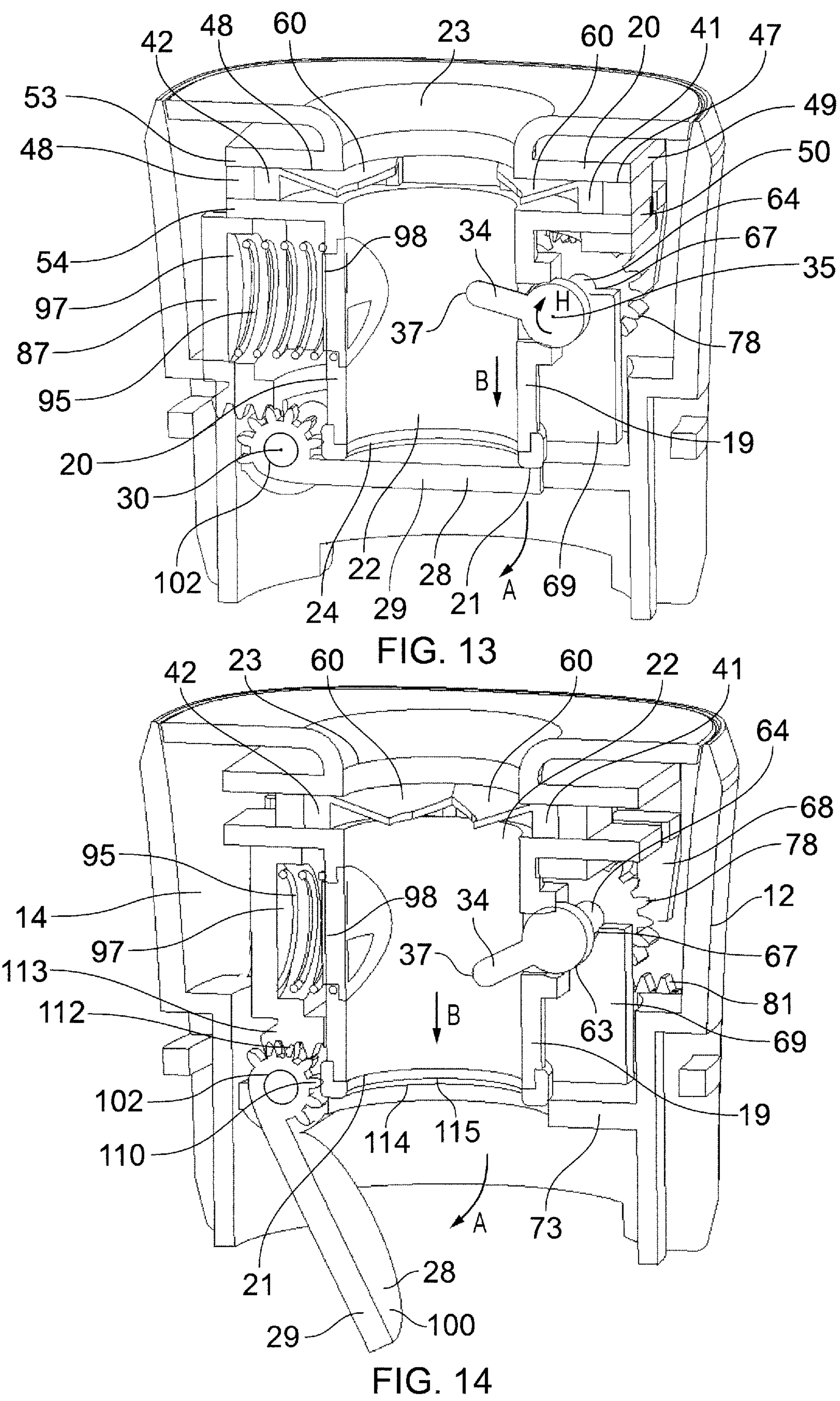
Figures 15, 16:
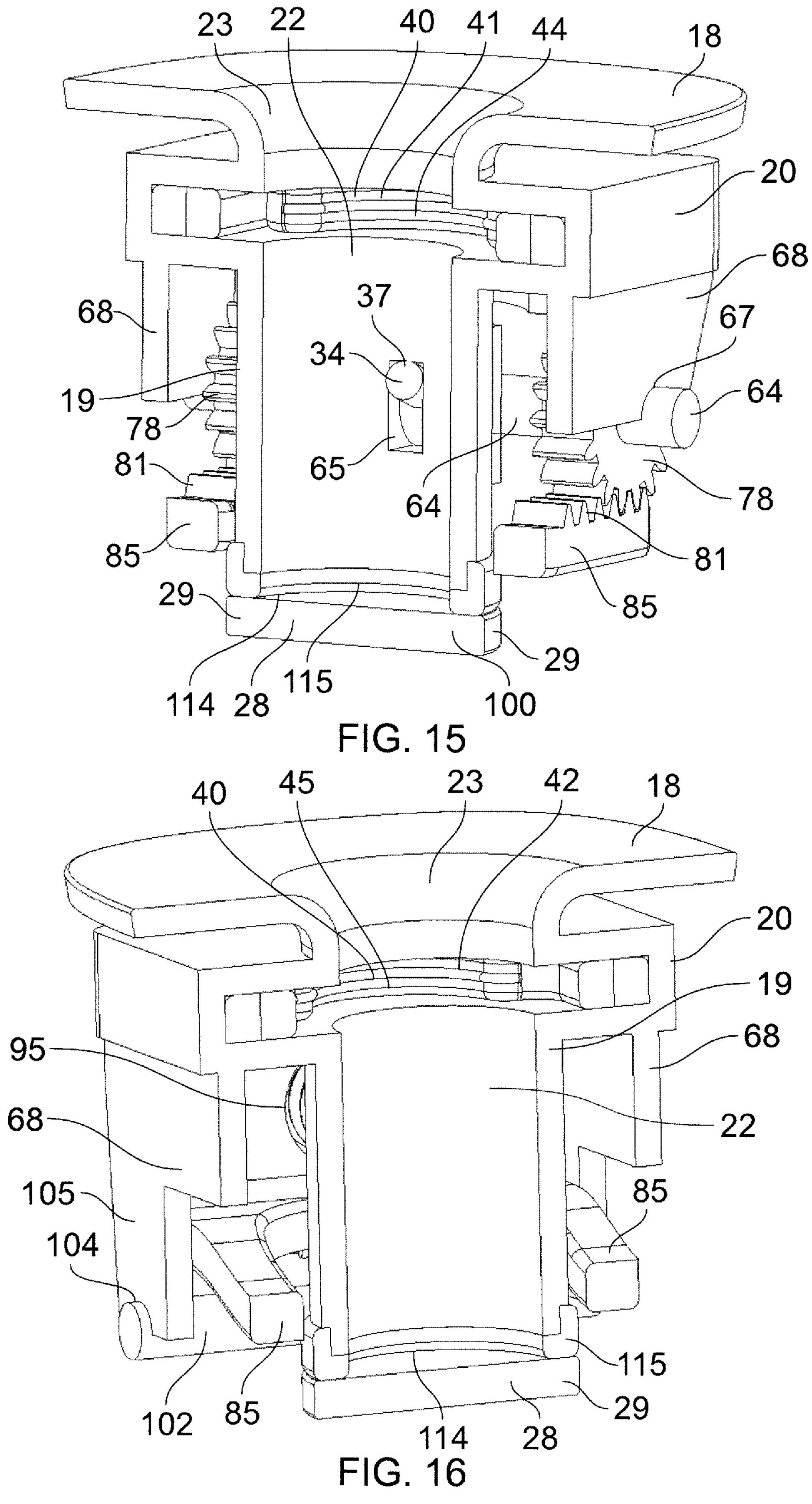
Figure 17:
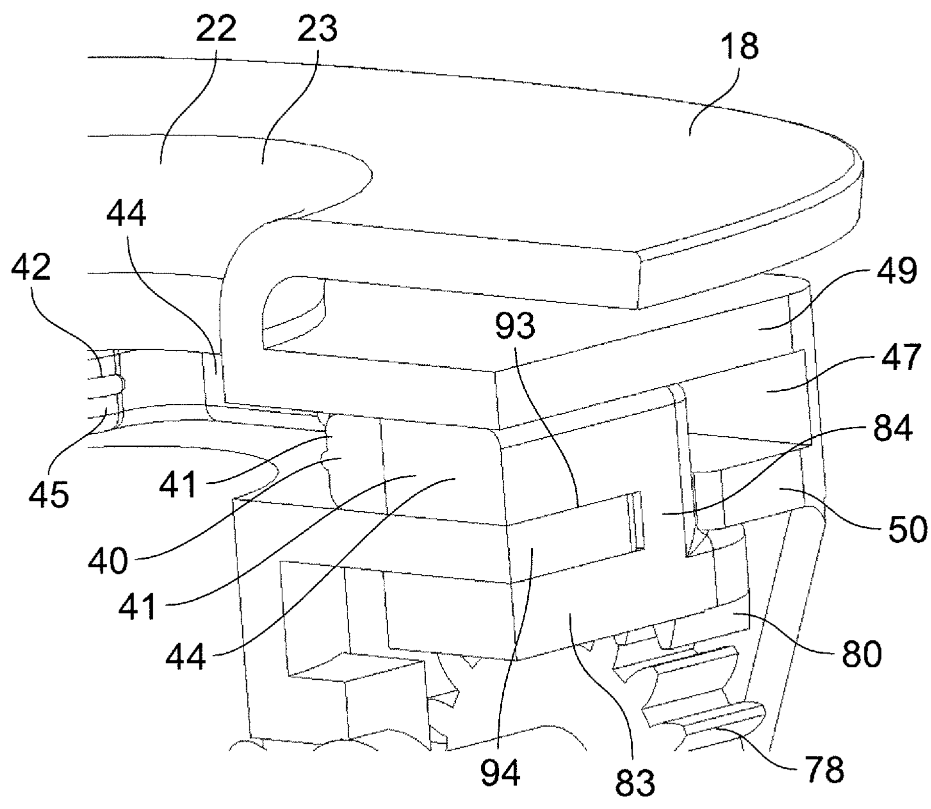
Figure 18:
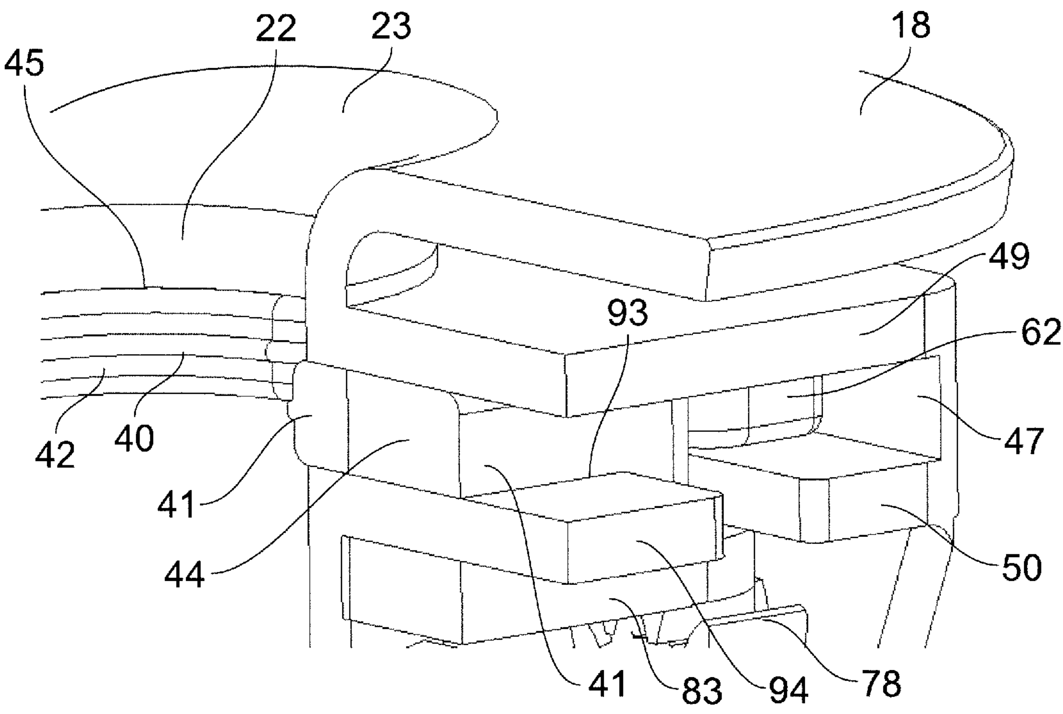
Figures 19, 20:
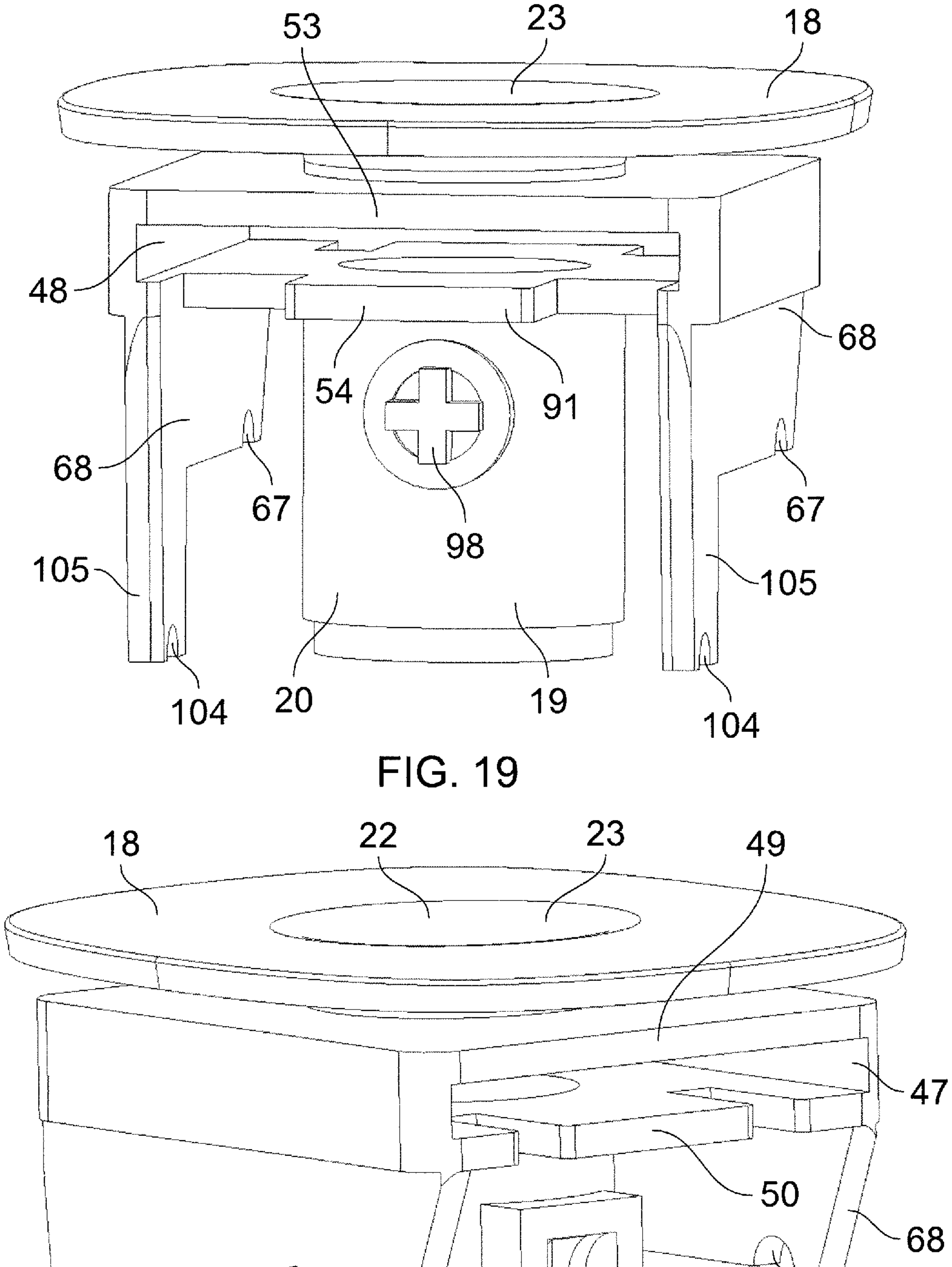
Figure 23:
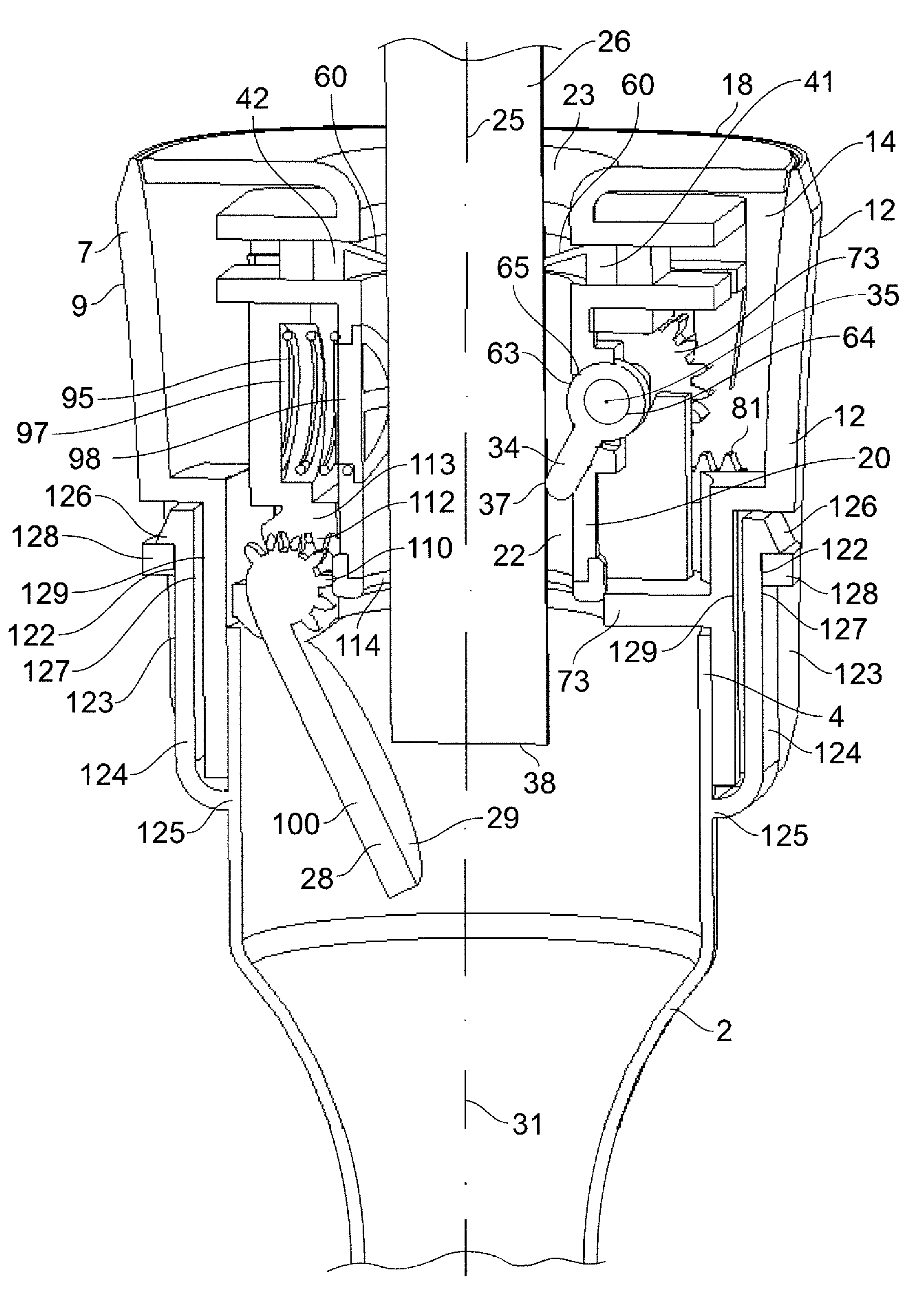
Figure 25:
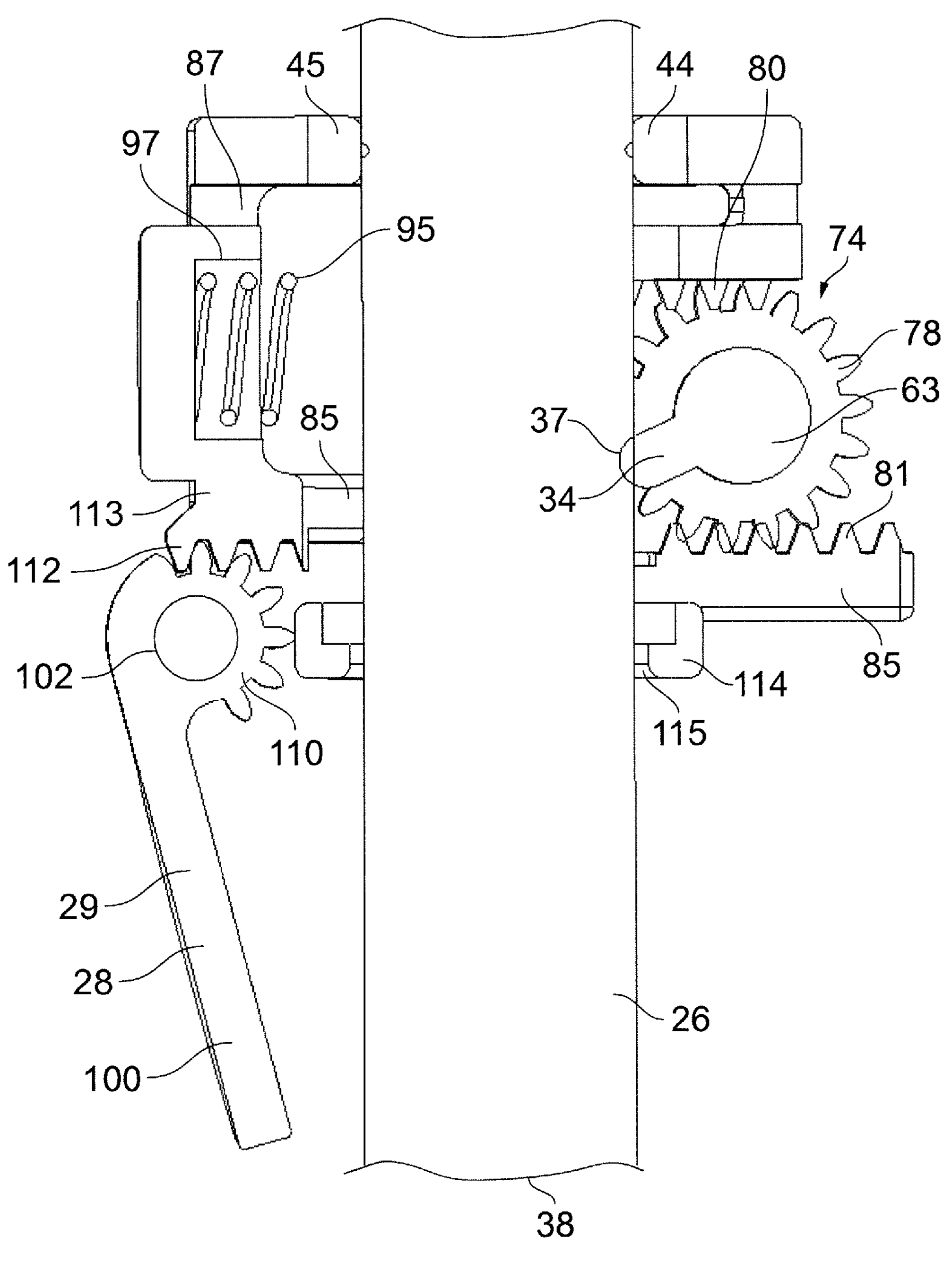
Figure 26:
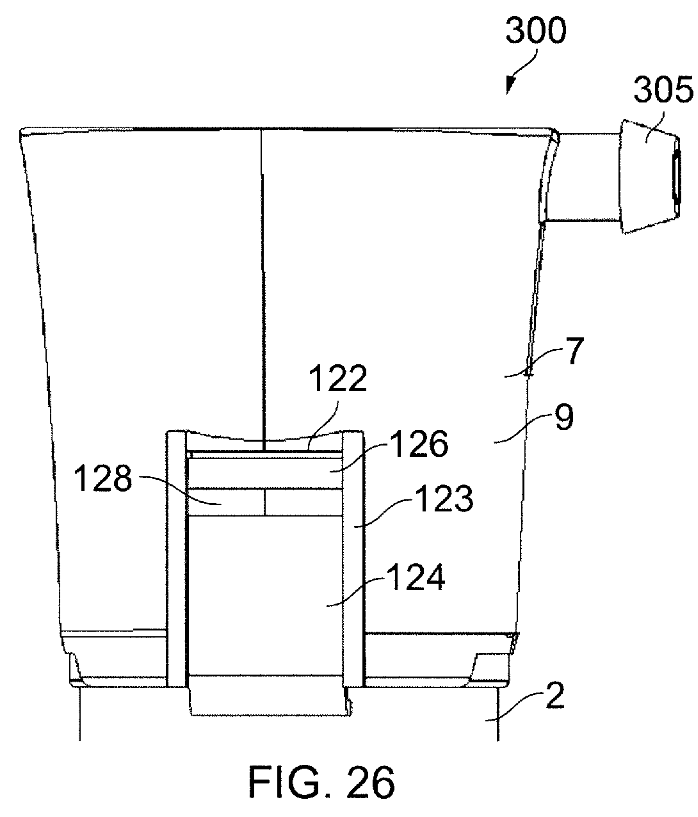
Figure 27:
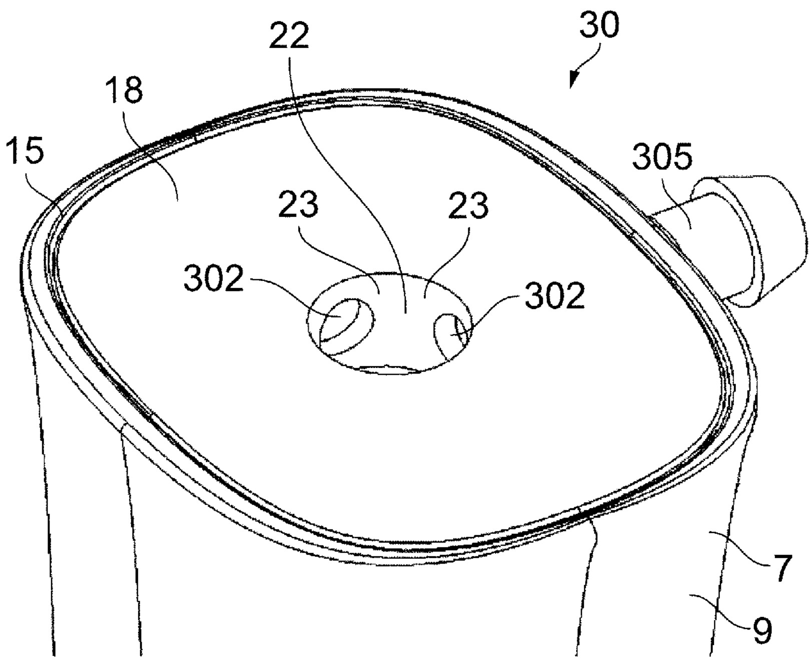
Figure 31:
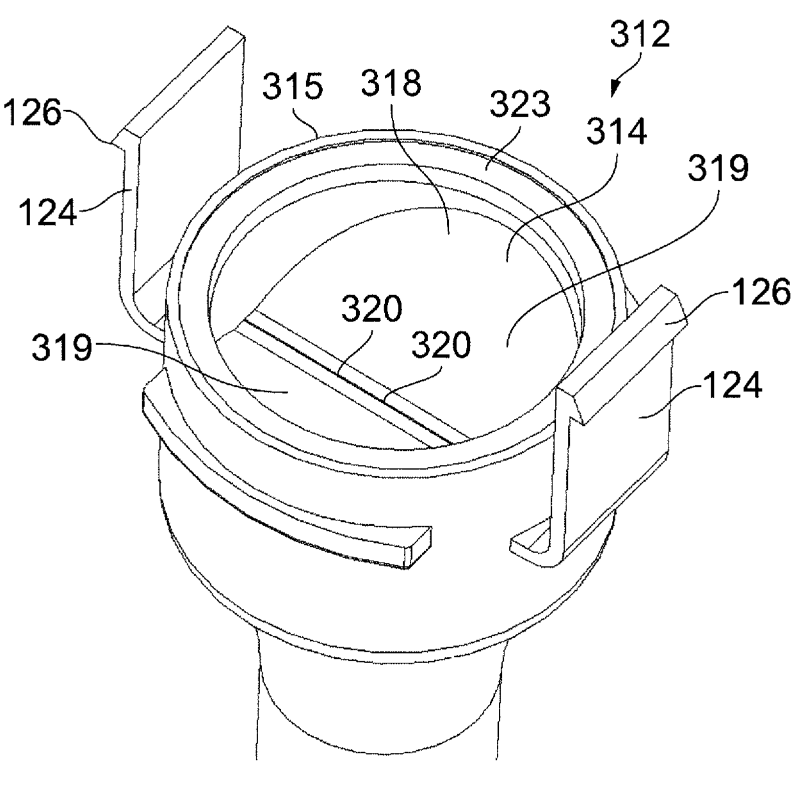
Figure 32:
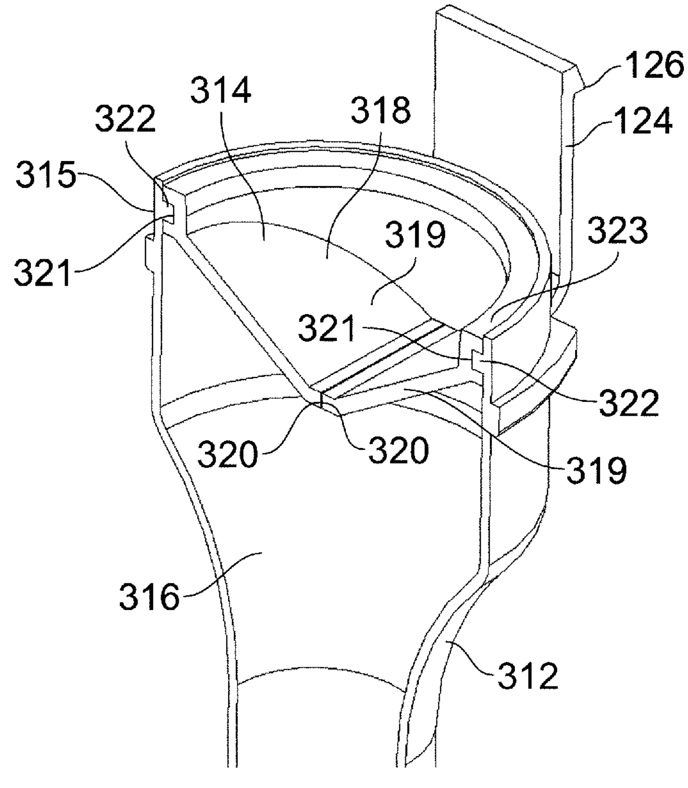
Figures 33, 35:
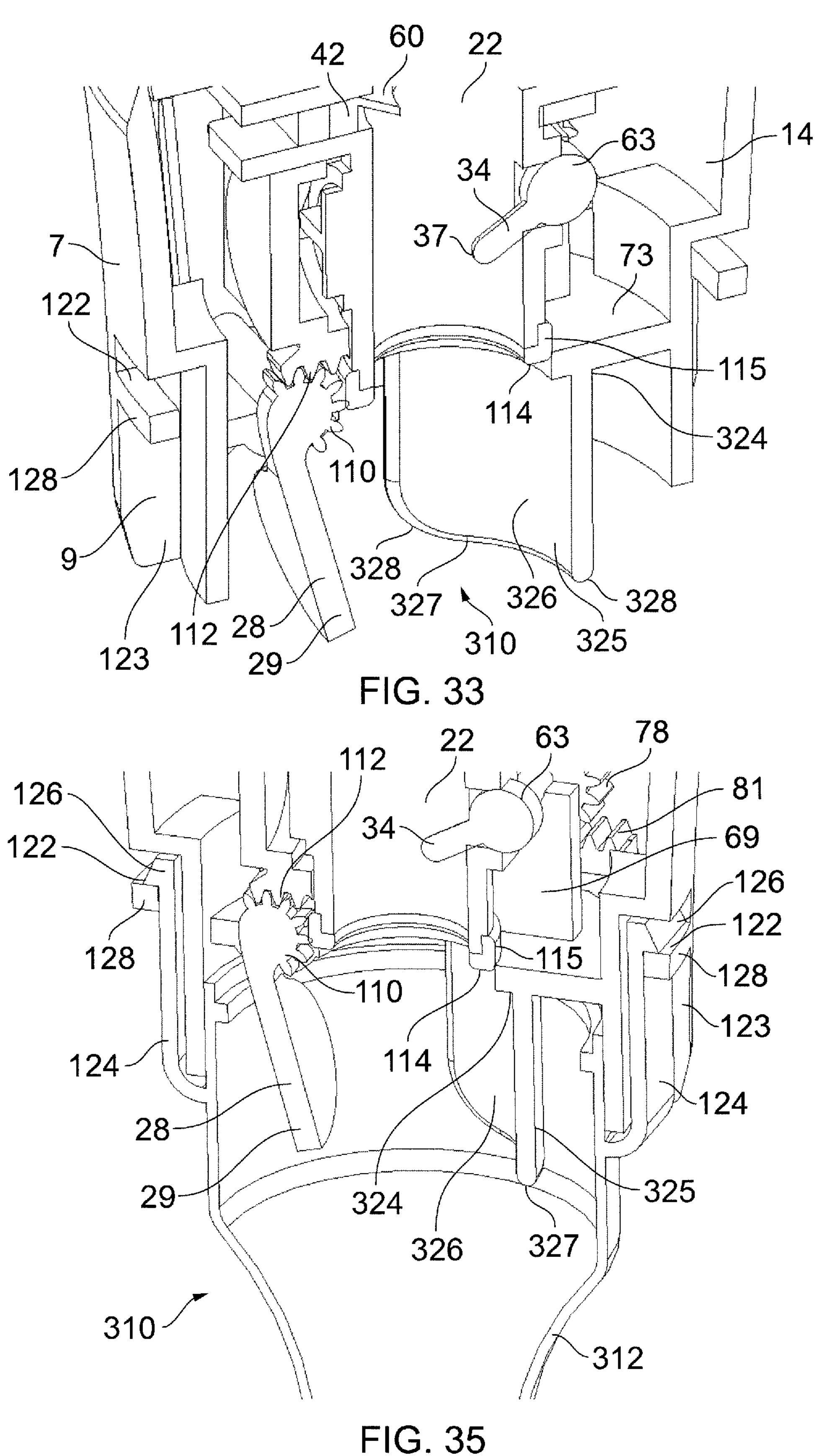
Figure 34:
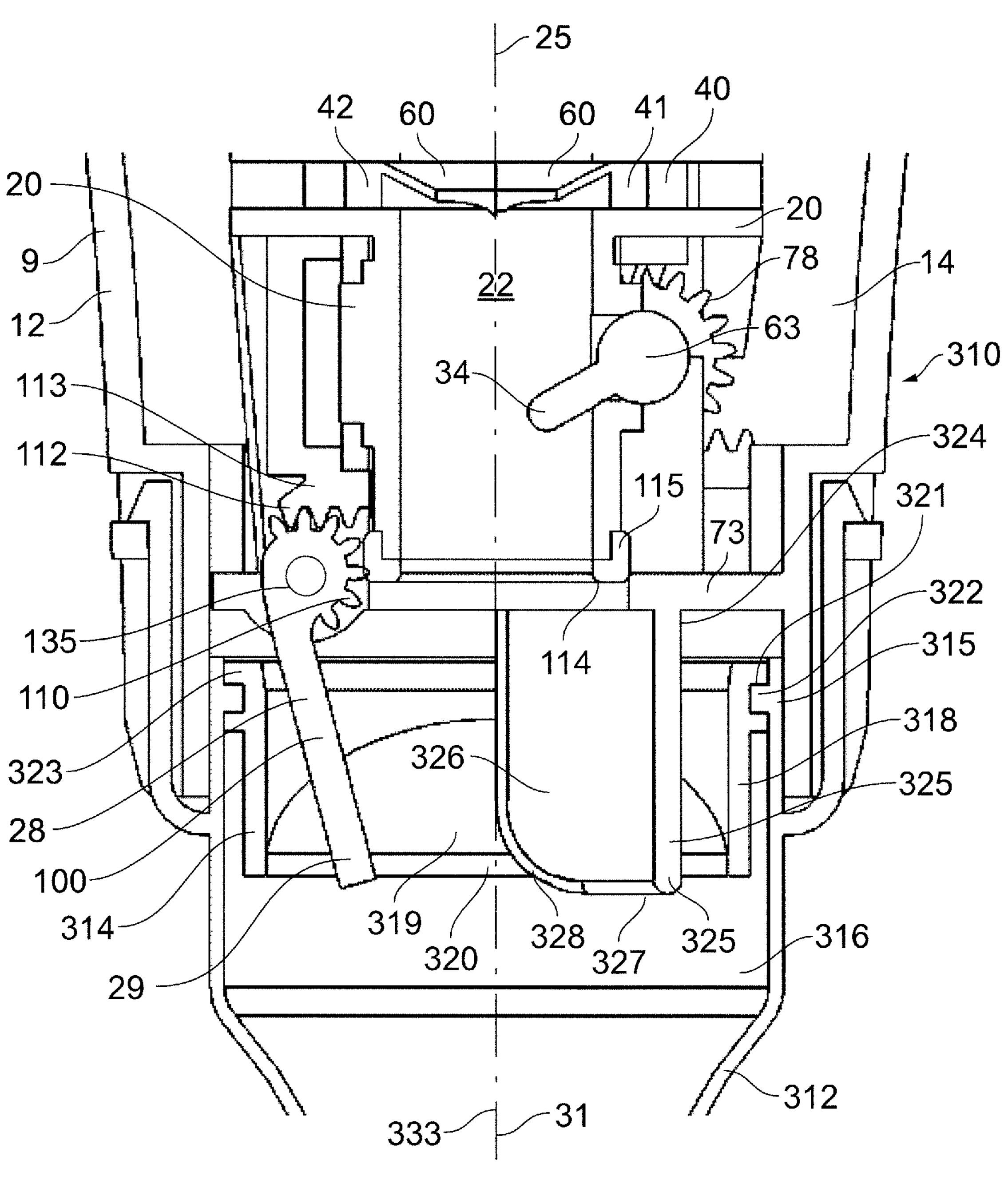
Figure 36:
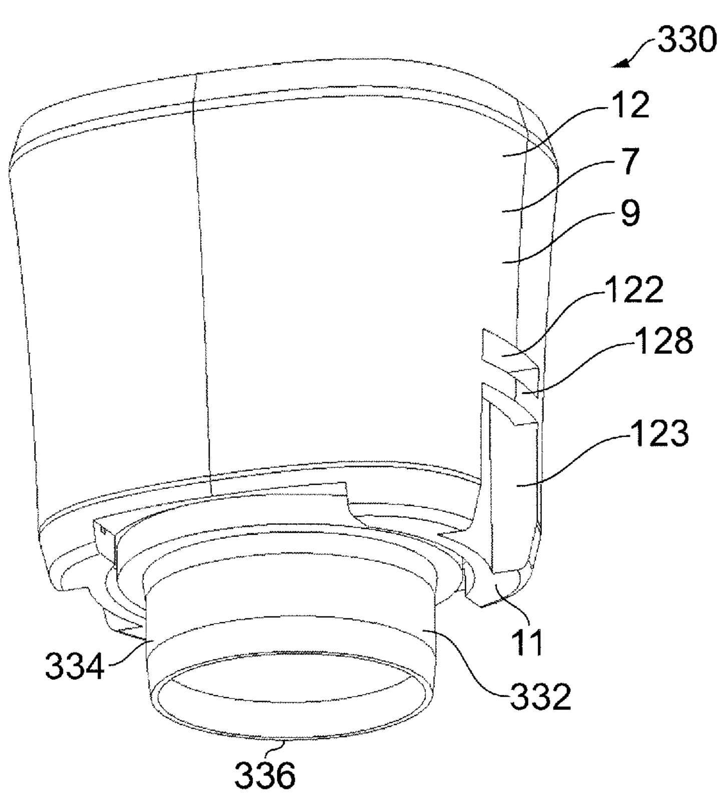
Figure 37:
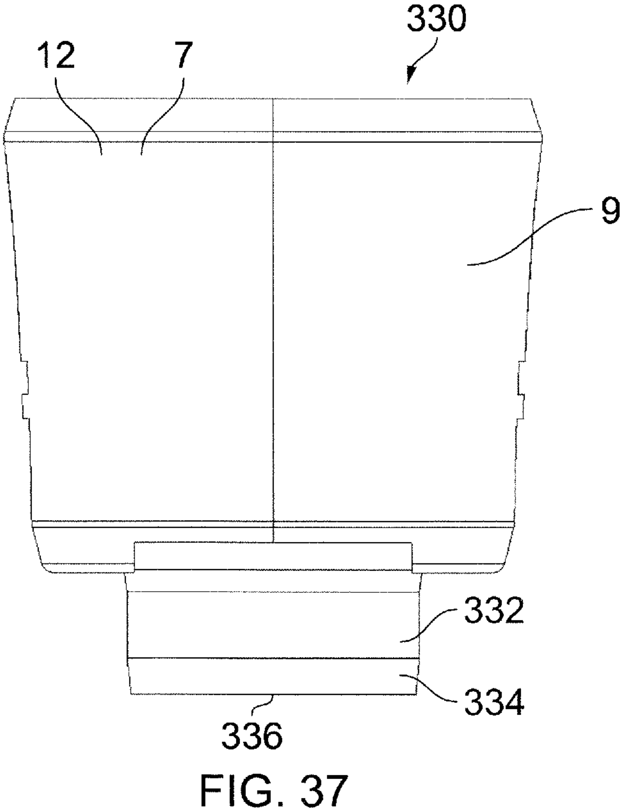
Figures 38, 39:
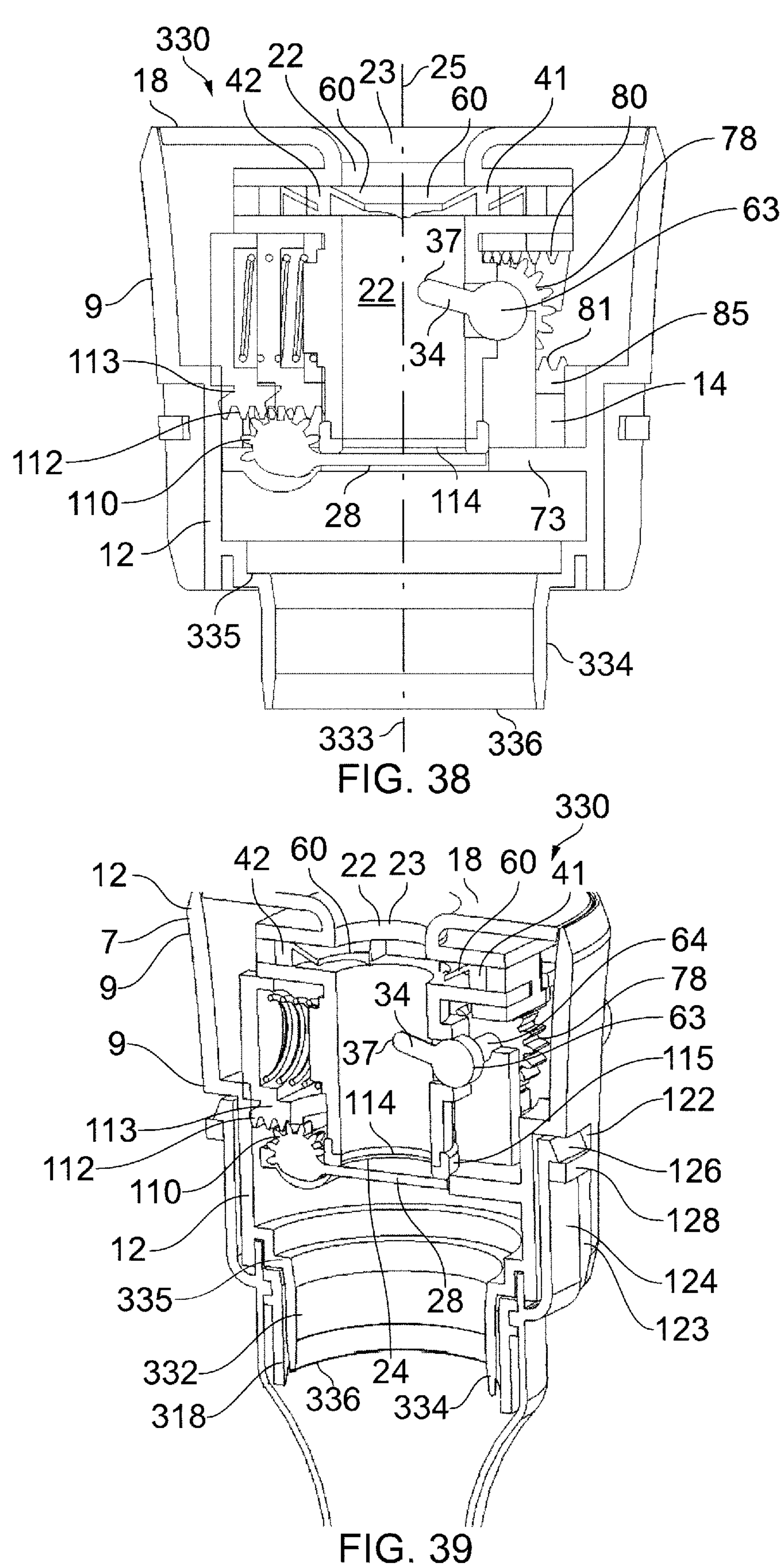
Figures 40, 41:
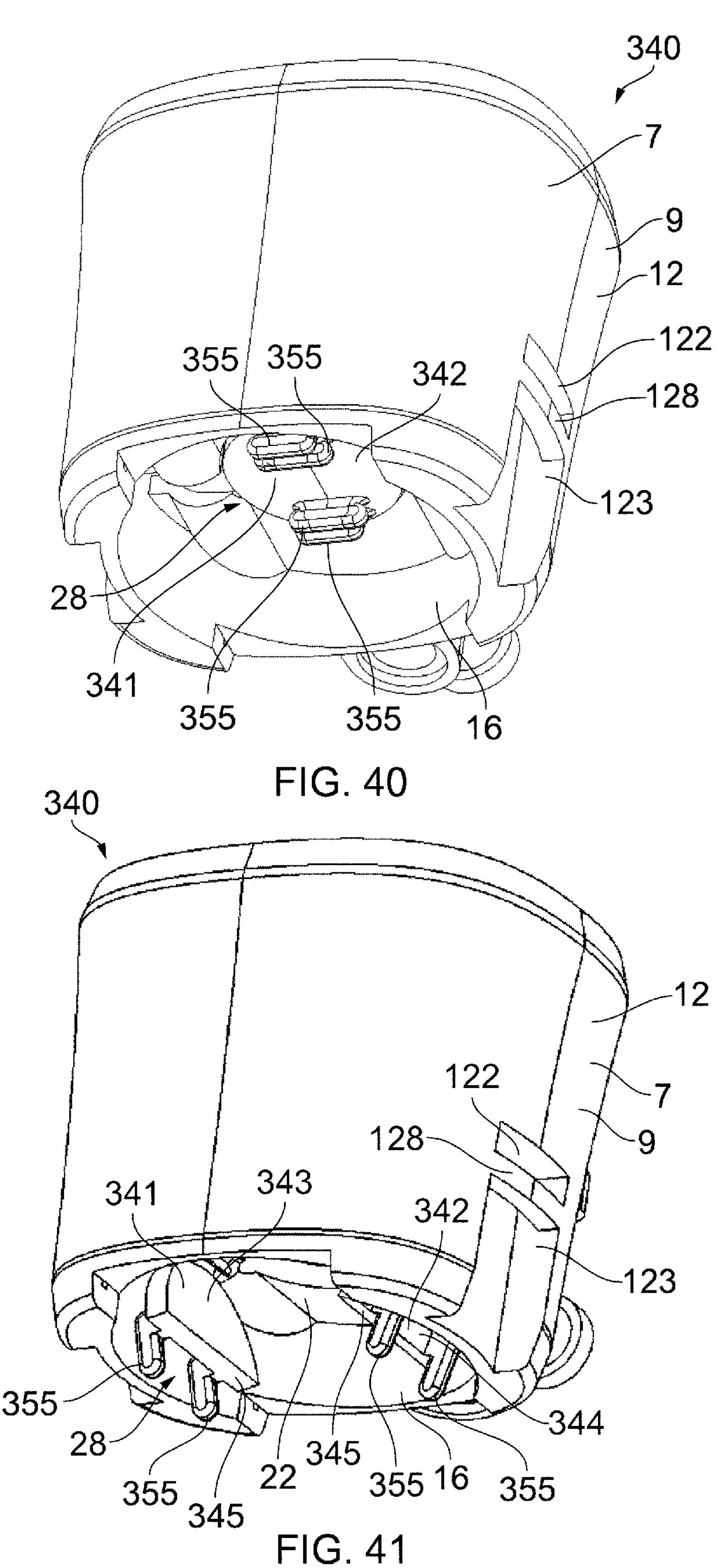
Figures 42, 43:
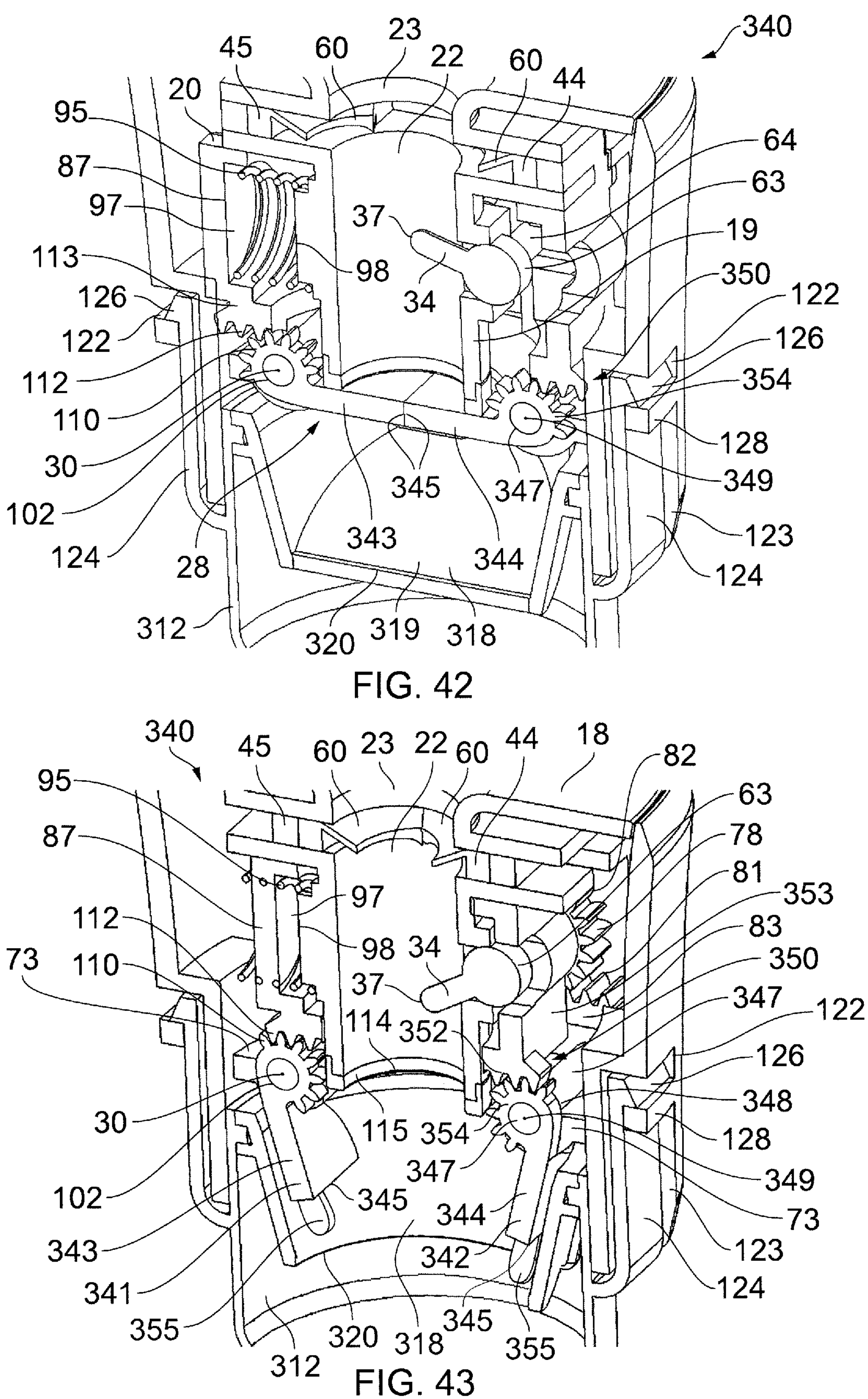
Figures 44, 45:
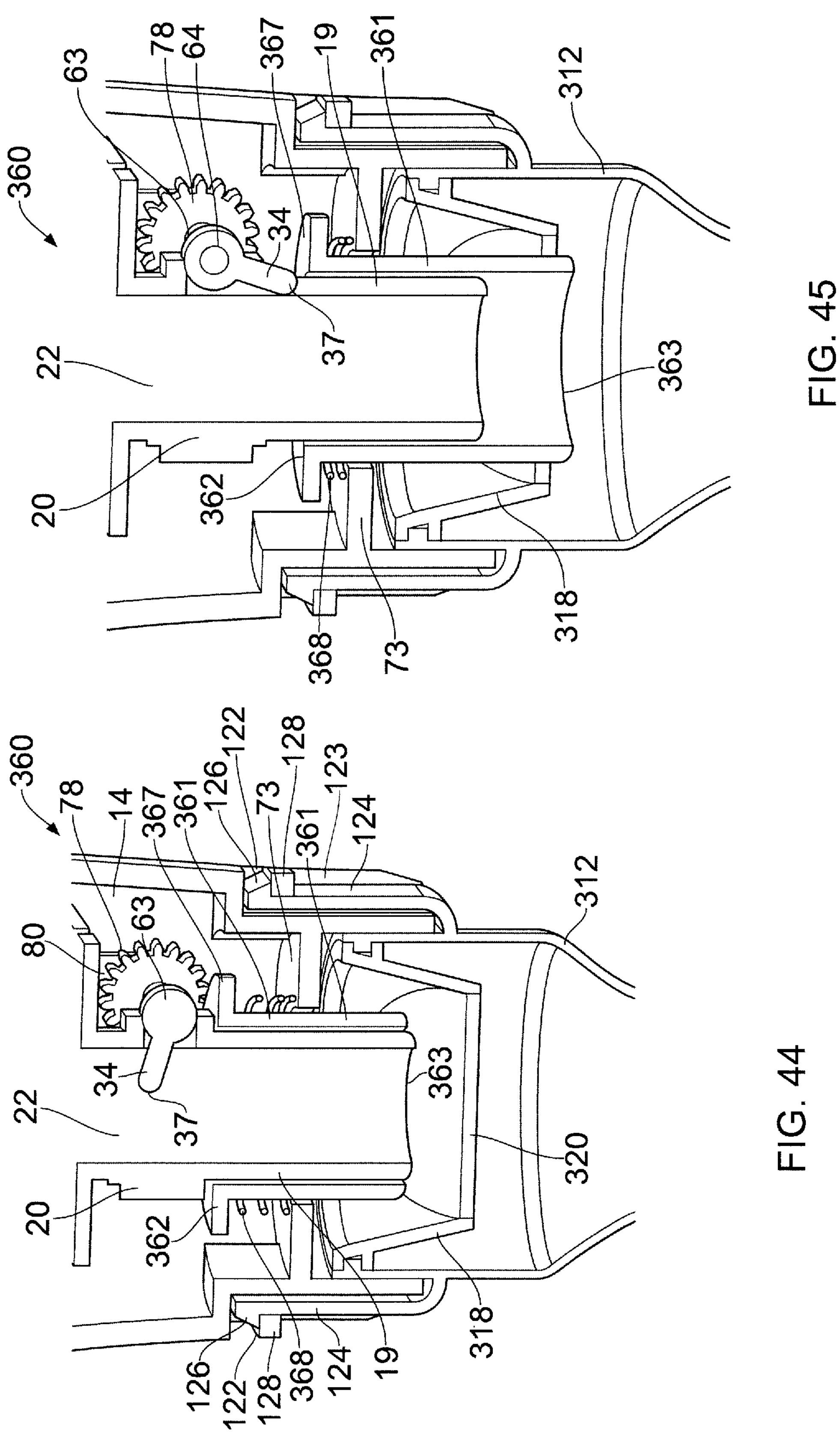
Figures 46, 47:
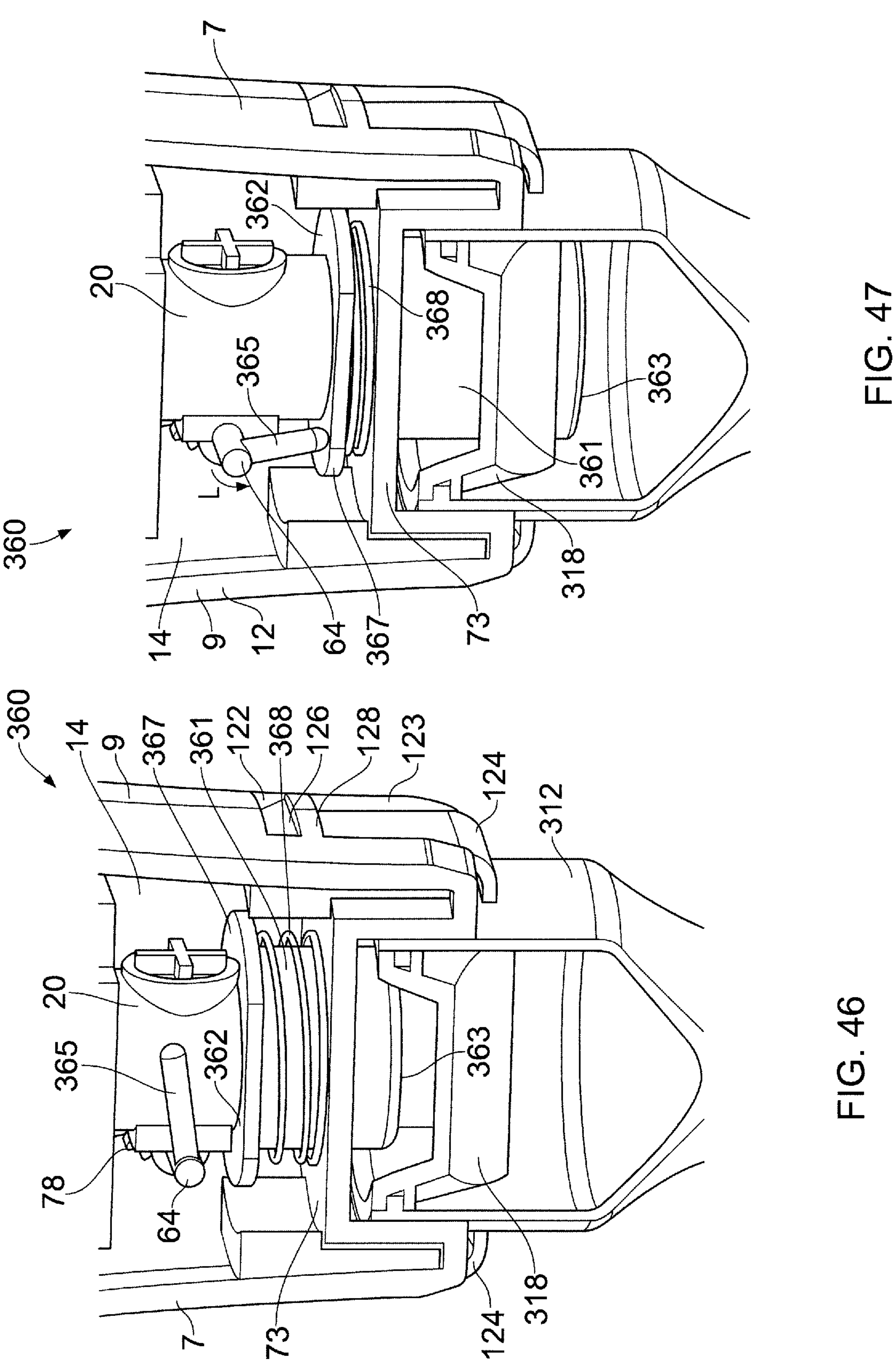
Figures 48, 49:
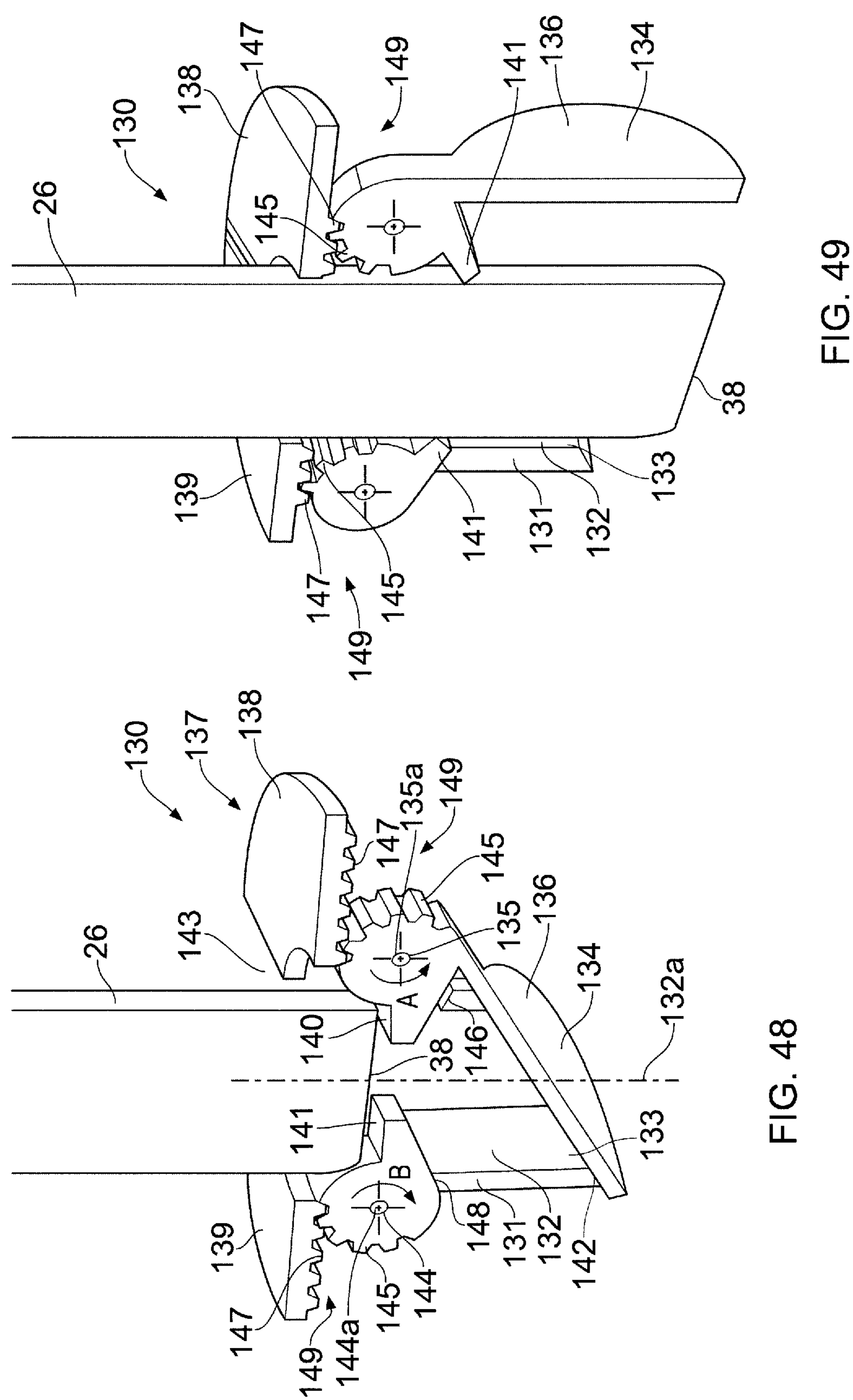
Figures 50, 51:
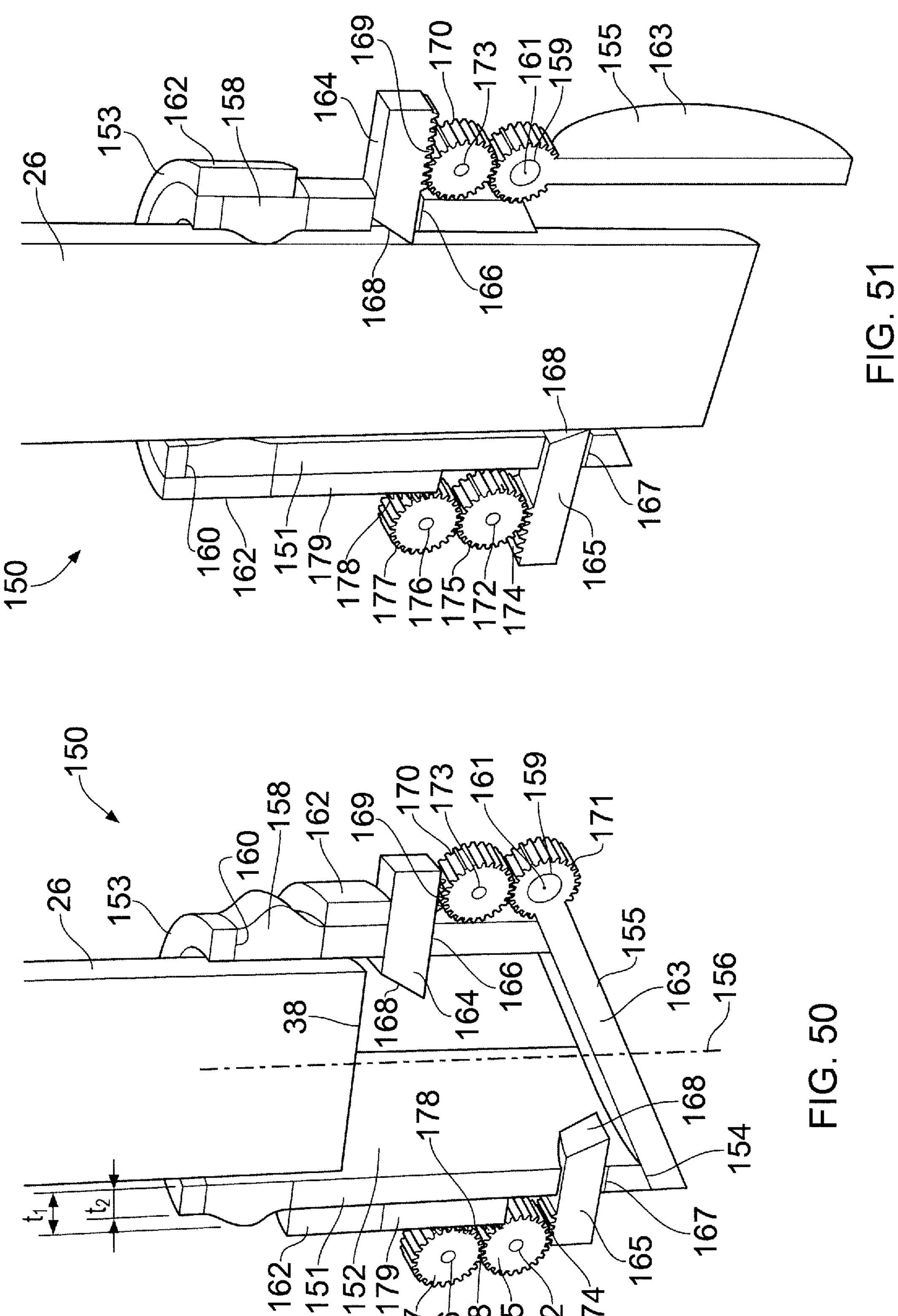
Figure 53:
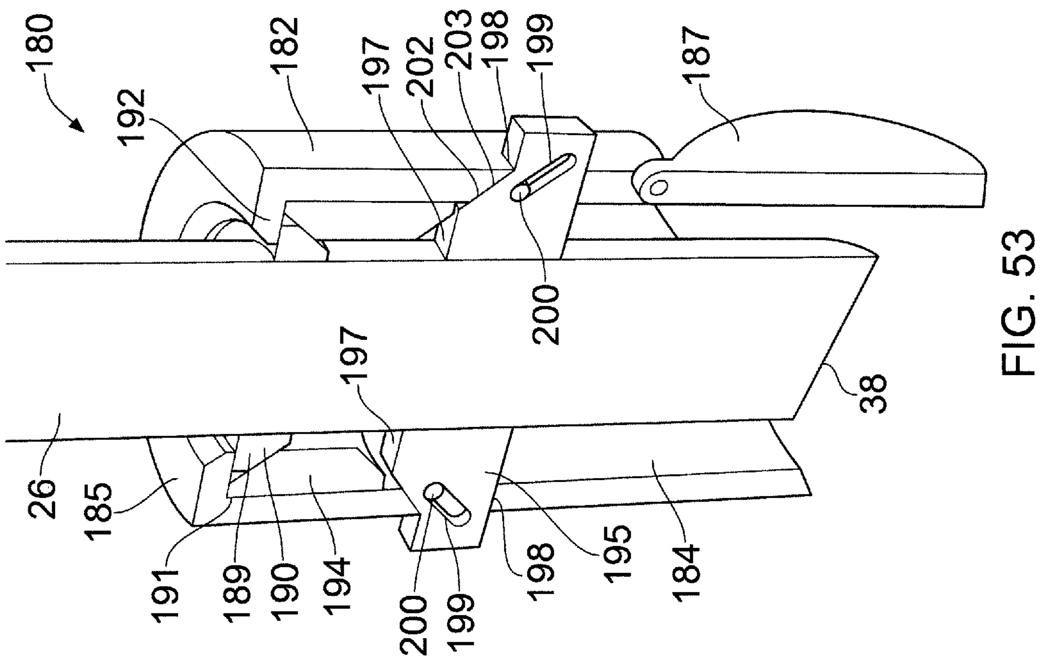
Figure 52:
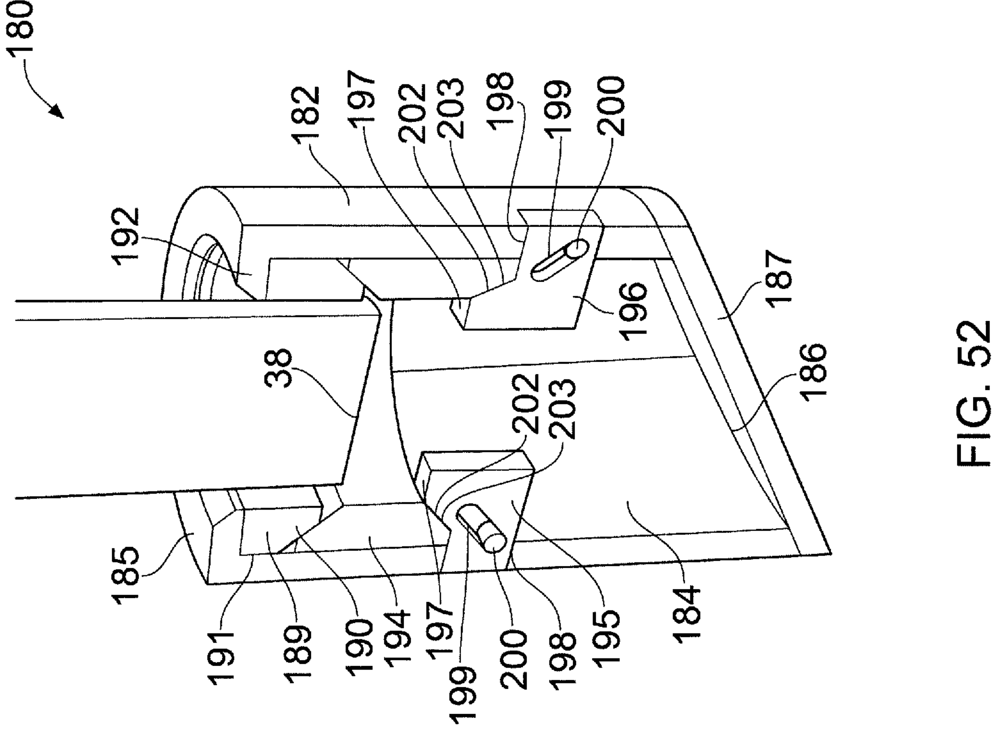
Figures 54, 55, 56:
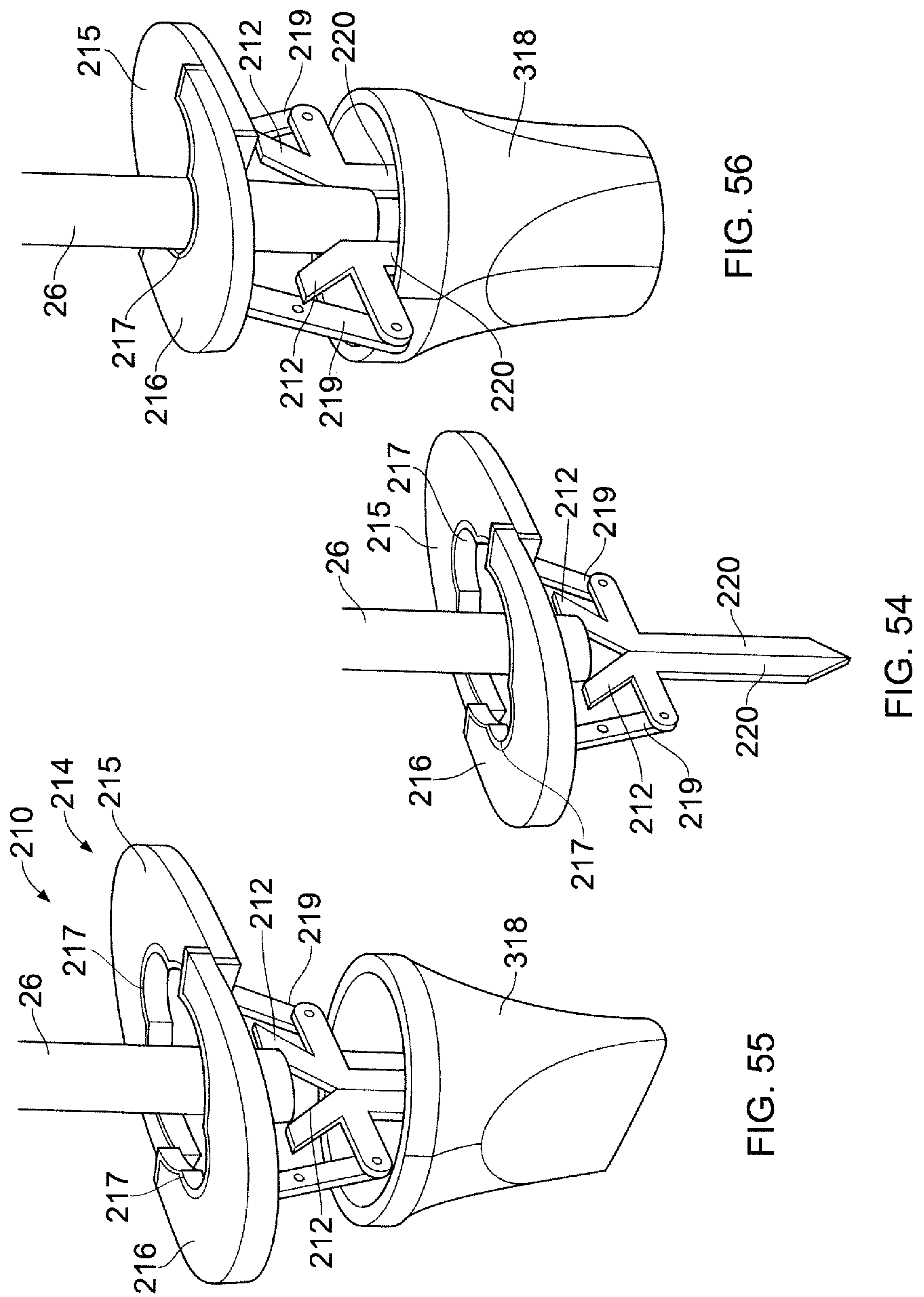
Figures 57, 58:
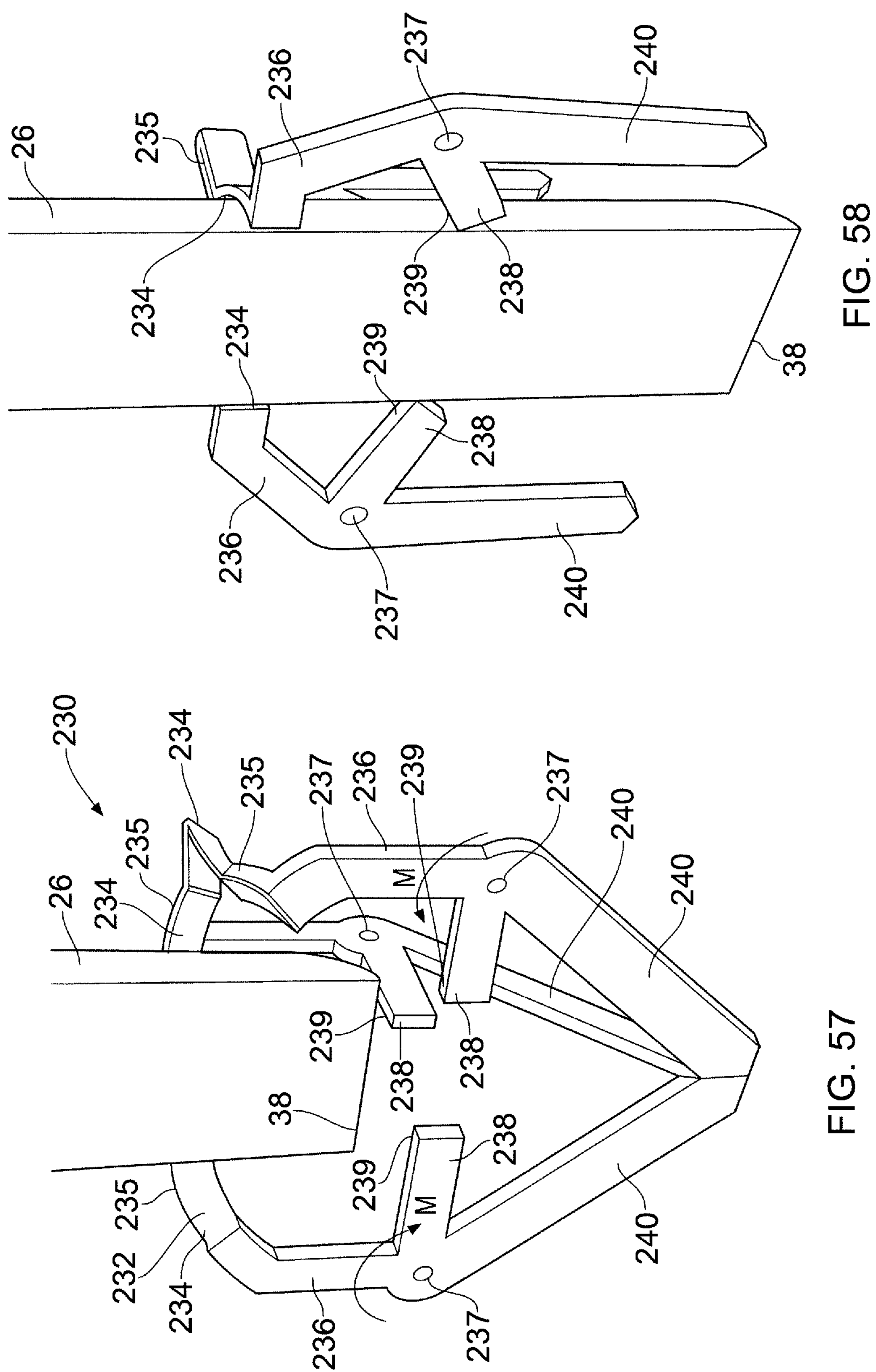
Figures 59, 60:
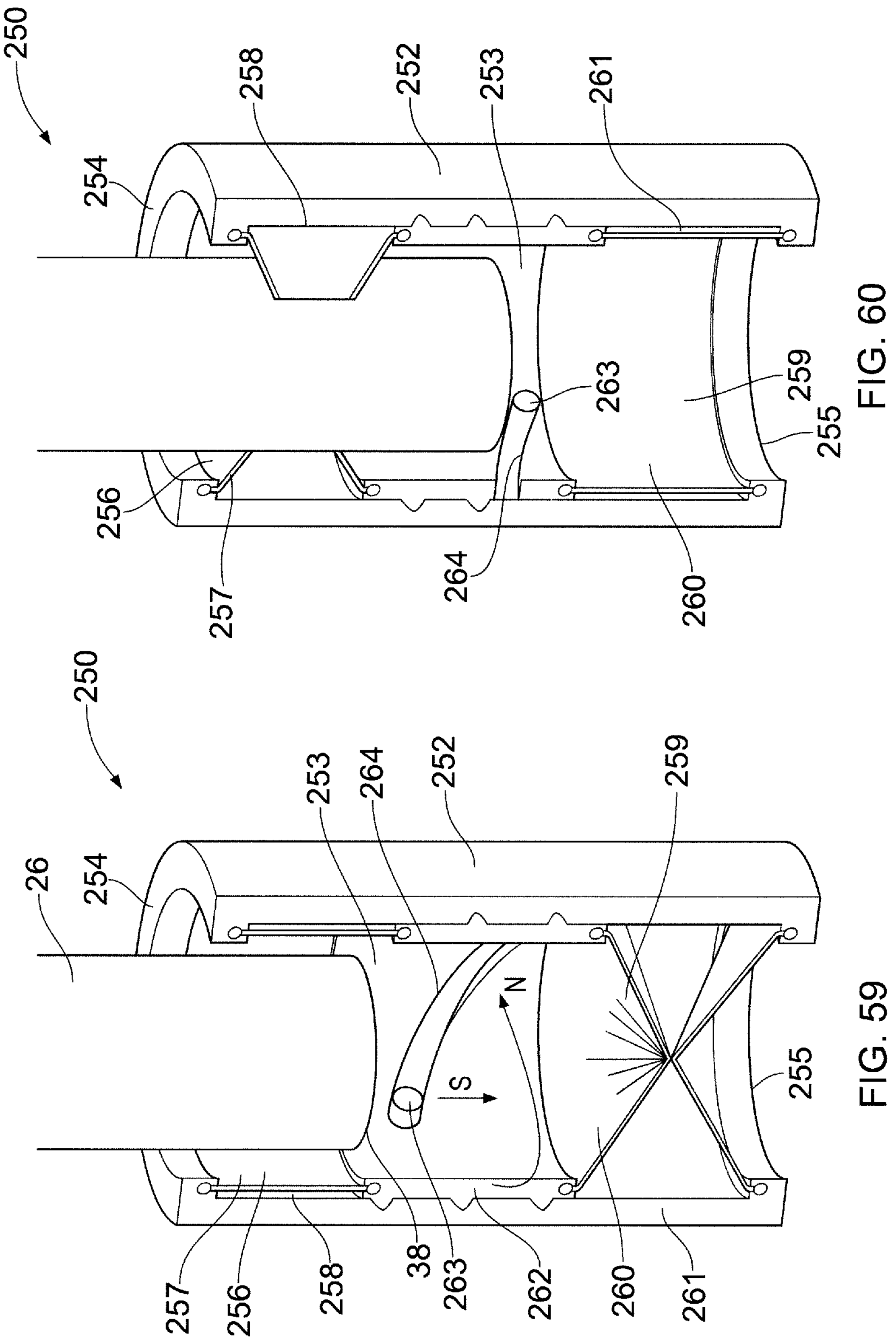

The invention will be more clearly understood from the following description of some preferred non-limiting embodiments thereof which are given by way of example only with reference to the accompanying drawings, in which:

FIG. 1 is a perspective view of an assembly according to the invention comprising a trocar cannula and a valve mechanism also according to the invention attached to the trocar cannula adjacent the proximal end thereof, FIG. 2 is another perspective view of the valve mechanism of FIG. 1, FIG. 3 is a front elevational view of the valve mechanism of FIG. 1, FIG. 4 is a side elevational view of the valve mechanism of FIG. 1, FIG. 5 is an underneath plan view of the valve mechanism of FIG. 1, FIG. 6 is a cross-sectional partly perspective view of the valve assembly of FIG. 1, FIG. 7 is a perspective view of a portion of the valve mechanism of FIG. 1, FIG. 8 is another perspective view of the portion of FIG. 7 of the valve mechanism of FIG. 1, FIG. 9 is a side elevational view of the portion of FIG. 7 of the valve mechanism of FIG. 1, FIG. 10 is a perspective view of a portion of the valve mechanism of FIG. 1, FIG. 11 is a view similar to FIG. 10 of the portion of FIG. 10 illustrating the portion of FIG. 10 in a different state to that of FIG. 10, FIG. 12 is a cross-sectional side elevational view of a portion of the valve mechanism and a portion of the trocar cannula of FIG. 1, FIG. 13 is a partly perspective cross-sectional side elevational view of the portion of FIG. 9 of the valve mechanism of FIG. 1, FIG. 14 is a view similar to FIG. 13 of the portion of FIG. 13 illustrating portions of the valve mechanism of FIG. 1 in a different state to that of FIG. 13, FIG. 15 is a cross-sectional perspective view of the half of the portion of FIG. 7 of the valve mechanism of FIG. 1, FIG. 16 is a cross-sectional perspective view of the other half of the portion of FIG. 7 to that of FIG. 15 of the valve mechanism of FIG. 1, FIG. 17 is a perspective view of a detail of the valve mechanism of FIG. 1, FIG. 18 is a perspective view of the detail of FIG. 17 illustrating part of the detail in a different state to that of FIG. 17, FIG. 19 is a perspective view of a part of the valve mechanism of FIG. 1, FIG. 20 is another perspective view of the part of FIG. 19 of the valve mechanism of FIG. 1, FIGS. 21 and 22 illustrate an exploded view of a part of the valve mechanism of FIG. 1, FIG. 23 is a cross-sectional partly perspective view of the valve mechanism of FIG. 1 in use, FIG. 24 is a cross-sectional side elevational view of a portion of the valve mechanism of FIG. 1 also illustrated in use, FIG. 25 is a view similar to that of FIG. 24 illustrating the portion of FIG. 24 of the valve mechanism of FIG. 1 also in use, FIG. 26 is a side elevational view of portion of a valve assembly according to another embodiment of the invention comprising a valve mechanism also according to the invention, and a portion of a trocar cannula to which the valve mechanism is attached, FIG. 27 is a top perspective view of a portion of the valve mechanism of FIG. 26, FIG. 28 is a cross-sectional perspective view of a detail of the valve mechanism of FIG. 26, FIG. 29 is a perspective view of a valve mechanism according to another embodiment of the invention, FIG. 30 is a side elevational view of the valve mechanism of FIG. 29, FIG. 31 is a perspective view of a portion of a trocar cannula, FIG. 32 is a cross-sectional perspective view of the trocar cannula of FIG. 31, FIG. 33 is a perspective view of a detail of the valve mechanism of FIG. 29, FIG. 34 is a cross-sectional side elevational view of a portion of the valve assembly according to another embodiment of the invention comprising the valve mechanism of FIG. 29, and the trocar cannula of FIG. 31, FIG. 35 is a perspective view of a detail of the valve assembly of FIG. 29, FIG. 36 is a perspective view of a valve mechanism according to another embodiment of the invention, FIG. 37 is a side elevational view of the valve mechanism of FIG. 36, FIG. 38 is a cross-sectional side elevational view of the valve mechanism of FIG. 36, FIG. 39 is a cross-sectional perspective view of a valve assembly comprising the valve mechanism of FIG. 37 and a portion of the trocar of FIG. 31, FIG. 40 is a perspective view of a valve mechanism according to another embodiment of the invention, FIG. 41 is another perspective view of the valve mechanism of FIG. 40 illustrating a portion of the valve mechanism in a different state to that of FIG. 40, FIG. 42 is a cross-sectional perspective view of a valve assembly also according to the invention comprising a portion of the valve mechanism of FIG. 40 and the trocar cannula of FIG. 31, FIG. 43 is a cross-sectional perspective view of the valve assembly of FIG. 42 with portions of the valve mechanism of FIG. 40 in a different state to that of FIGS. 40 and 42, FIG. 44 is a cross-sectional perspective view of a portion of a valve assembly according to another embodiment of the invention comprising a portion of a valve mechanism according to another embodiment of the invention and a portion of the trocar cannula of FIG. 31, FIG. 45 is a view substantially similar to FIG. 44 of the portion of the valve assembly of FIG. 44 illustrating portions of the valve assembly in different states to those of FIG. 44, FIG. 46 is another cross-sectional perspective view of the portion of the valve assembly of FIG. 44 illustrating portions of the valve assembly in the states of FIG. 44, FIG. 47 is a view substantially similar to FIG. 46 of the portion of the valve assembly of FIG. 46 illustrating portions of the valve assembly in the states of FIG. 45, FIG. 48 is a cross-sectional perspective view of a detail of a valve mechanism according to another embodiment of the invention, FIG. 49 is a cross-sectional perspective view of the portion of the valve mechanism of FIG. 48 illustrated in a different state to that of FIG. 48, FIG. 50 is a cross-sectional perspective view of a portion of a valve mechanism according to another embodiment of the invention, FIG. 51 is a cross-sectional perspective view of the valve mechanism of FIG. 50 illustrating portions of the valve mechanism in a different state to that of FIG. 50, FIG. 52 is a cross-sectional perspective view of a portion of a valve mechanism according to another embodiment of the invention, FIG. 53 is a cross-sectional perspective view of a portion of the valve mechanism of FIG. 52 illustrating portions of the valve mechanism in a different state to that of FIG. 52, FIG. 54 is a perspective view of a portion of a valve mechanism according to another embodiment of the invention, FIG. 55 is a perspective view of the portion of the valve mechanism of FIG. 54 illustrated partly in use, FIG. 56 is a perspective view of the valve mechanism of FIG. 54 illustrated also in use, FIG. 57 is a cross-sectional perspective view of a portion of a valve mechanism according to another embodiment of the invention, FIG. 58 is a view similar to FIG. 57 of the valve mechanism of FIG. 57 illustrating portions of the valve mechanism in a different state to that of FIG. 57, FIG. 59 is a cross-sectional perspective view of a portion of a valve mechanism according to another embodiment of the invention, and FIG. 60 is a cross-sectional perspective view of the portion of FIG. 59 of the valve mechanism of FIG. 59 illustrating portions of the valve mechanism in a different state to that of FIG. 59.

Referring to the drawings and initially to FIGS. 1 to 25 thereof, there is illustrated an assembly according to the invention indicated generally by the reference numeral 1, comprising a trocar cannula 2 and a valve mechanism also according to the invention and indicated generally by the reference numeral 3 mounted on the trocar cannula 2 adjacent a proximal end 4 thereof. The valve mechanism 3 is configured for minimising leakage of gases, typically, insufflating gases and other gases from an insufflated cavity or vessel of a human or animal subject into which the trocar cannula 2 extends during insufflation of the cavity or vessel of the human or animal subject.

The trocar cannula 2 extends from the proximal end 4 to a distal end 5, which in use is inserted into the vessel or cavity of the subject being insufflated. Such trocar cannulae as the trocar cannula 2 will generally be well known to those skilled in the art, and further description of the trocar cannula 2 should not be required.

Although the valve mechanism 3 is described for mounting on a trocar cannula, the valve mechanism 3 could also be provided for mounting on a trocar, in which case the valve mechanism would be mounted on the proximal trocar housing, adjacent the proximal end of the proximal trocar housing.

Referring now to the valve mechanism 3, the valve mechanism 3 comprises a housing 7 having a main housing 9 extending from a proximal end 10 to a distal end 11. The main housing 9 comprises an outer peripheral wall 12 extending around the valve mechanism 3 and defining a hollow interior region 14. The outer peripheral wall 12 adjacent the proximal end 10 thereof defines a proximal open mouth 15 to the hollow interior region 14. The outer peripheral wall 12 adjacent the distal end 11 thereof defines a distal open mouth 16 which is configured as will be described below for sealably engaging the trocar cannula 2 adjacent the proximal end 4 thereof.

A proximal closure plate 18 is sealably secured to the outer peripheral wall 12 and sealably closes the proximal open mouth 15.

A sub-housing 20 extends distally from the proximal closure plate 18 into the hollow interior region 14 defined by the main housing 9 and terminates at a distal end 21 within the hollow interior region 14. A tubular portion 19 of the sub-housing 20 defines an instrument bore 22, which extends through the sub-housing 20 and also through the proximal closure plate 18 between a proximal end 23 and a distal end 24. The instrument bore 22 accommodates medical and surgical instruments 26, for example, a laparoscope or the like therethrough. The instrument bore 22 defines a longitudinally extending main central axis 25. When the valve mechanism 3 is secured to the trocar cannula 2 adjacent the proximal end 4 thereof, the instrument bore 22 is aligned with an instrument bore 27 extending through the trocar cannula 2 as will be described below, with the main central axis 25 defined by the instrument bore 22 aligned with and coinciding with a central axis 31, see FIG. 6.

A distal valve 28 comprising a distal valve member 29 pivotal about a distal valve pivot axis 30, as will be described below, is pivotal about the distal valve pivot axis 30 in a generally distal direction, namely, in the direction of the arrow A from a closed state illustrated in FIGS. 6, 13 and 14 cooperating with the distal end 21 of the tubular portion of the sub-housing 20 sealably closing the instrument bore 22, to an open state illustrated in FIGS. 14 and 25 for accommodating the instrument 26 through the instrument bore 22, and in turn into the instrument bore 27 of the trocar cannula 2. The distal valve 28 and its operation will be described in more detail below.

A detecting means comprising a detecting probe 34 is pivotally mounted in the sub-housing 20 spaced apart proximally from the distal valve 28, and is pivotal about a primary pivot axis 35 as will be described below. The detecting probe 34 extends radially relative to the primary pivot axis 35 into the instrument bore 22, see for example, FIGS. 6, 13 and 14. The detecting probe 34 terminates in a distal, instrument engagement element, namely, a distal, instrument engagement tip 37 for engaging a distal end 38 of the instrument 26 being urged distally through the instrument bore 22, see FIGS. 23, 24 and 25. The detecting probe 34 is pivotal about the primary pivot axis 35, as will be described below, distally, namely, in the direction of the arrow B, from a first state illustrated in FIG. 13 to a second state illustrated in FIG. 14 in response to engagement of the distal tip 37 of the detecting probe 34 by the distal end 38 of the distally moving instrument 26 in the instrument bore 22.

The distal valve 28 is urgeable from the closed state to the open state, as will be described below, in response to the detecting probe 34 being urged distally from the first state to the second state, so that the distal valve 28 is urged into the open state prior to the distal end 38 of the instrument 26 reaching the distal end 24 of the instrument bore 22. Thus, contact between the instrument 26 and the distal valve 28 is avoided.

A proximal valve 40 located adjacent the proximal end 23 of the instrument bore 22, spaced apart proximally from the detecting probe 34, is configured to sealably engage the instrument 26, while the instrument 26 is in the instrument bore 22, and as the instrument 26 is being urged through the instrument bore 22, for minimising leakage of insufflating gas and other gases from the cavity of the subject being insufflated. The proximal valve 40, as will be described in more detail below, comprises a pair of proximal valve members, namely, a first valve member 41 and a second valve member 42. The first and second valve members 41 and 42 are located in the sub-housing 20, and are slideable therein in the directions of the arrows C from a withdrawn state illustrated in FIGS. 6, 10 and 11, withdrawn into the sub-housing 20, to an engagement state illustrated in FIGS.

11 and 14 extending into the instrument bore 22 for sealably engaging the instrument 26 in the instrument bore 22, in order to minimise the escape of insufflating and other gases through the instrument bore 22. The first and second proximal valve members 41 and 42 as will also be described in more detail below are urgeable in the directions of the arrows C from the withdrawn state into the engagement state in response to the detecting probe 34 being urged distally by the instrument 26 from the first state to the second state.

Turning now in more detail to the proximal valve 40, the first and second proximal valve members 41 and 42 comprises respective first and second valve plate members 44 and 45, respectively. Guide means, in this embodiment of the invention comprising a first guide slot 47 and a second guide slot 48 in the sub-housing 20 guide the first and second valve plate members 44 and 45, respectively, between the withdrawn state and the engagement state, see for example, FIGS. 13, 14, 19 and 20.

The first guide slot 47, within which the first valve plate member 44 is slideable, is defined between a pair of side flanges, namely, a first proximal side flange 49 and a first distal side flange 50, which extend sidewardly outwardly from the sub-housing 20, and define therebetween the first guide slot 47. The first guide slot 47 extends into the instrument bore 22 for slideably accommodating the first valve plate member 44 from the withdrawn state within the first guide slot 47 into the engagement state extending into the instrument bore 22.

The second guide slot 48, within which the second valve plate member 45 is slideable, is defined between a pair of spaced apart side flanges, namely, a second proximal side flange 53 and a second distal side flange 54 extending sidewardly outwardly from the sub-housing 20 on the opposite side thereof to that from which the first proximal and distal side flanges 49 and 50 extend. The second guide slot 48 extends into the instrument bore 22 for slideably accommodating the second valve plate member 45 from the withdrawn state within the second guide slot 48 into the engagement state extending into the instrument bore 22.

The first valve plate member 44 defines an arcuate first central sealing portion 55, and the second valve plate member 45 defines a second arcuate central sealing portion 56. The first and second central sealing portions 55 and 56 each extend approximately 180° around the main central axis 25 of the instrument bore 22, and when the first and second valve plate members 44 and 45 are in the engagement state, together the first and second central sealing portions 55 and 56 substantially define the transverse cross-section of the instrument 26 in the instrument bore 22, see for example, FIGS. 10 and 11.

Each of the first and second valve plate members 44 and 45 define respective pairs of side sealing portions 58 which extend from the corresponding central sealing portions 55 or 56. The side sealing portions 58 of each one of the first and second valve plate members 44 and 45 cooperate with each other for forming respective seals therebetween when the first and second valve plate members 44 and 45 are in the engagement state.

A first sealing means comprising a pair of first arcuate resilient flexible sealing flanges 60 extend from the respective first and second central sealing portions 55 and 56 for sealably engaging the instrument 26 in the instrument bore 22 when the first and second valve plate members 44 and 45 are in the engagement state for minimising leakage of insufflating gas and other gases from a cavity of a subject being insufflated proximally through the instrument bore 22, see in particular FIGS. 6, 13, 14 and 23.

A pair of spaced apart side members 62 extend from the second valve plate member 45 on respective opposite sides thereof and slideably engage and embrace the first valve plate member 44, see FIGS. 10 and 11 for centering the first and second central sealing portions 55 and 56 relative to the instrument 26 when the first and second valve plate members 44 and 45 are in the engagement state.

Turning now in more detail to the detecting probe 34, the detecting probe 34 comprises an elongated member 36 extending radially from a cylindrical annular flange 63 extending around a primary pivot shaft 64 which is pivotally mounted in the sub-housing 20. The detecting probe 34 extends radially from the flange 63 through a probe accommodating opening 65 extending through the sub-housing 20 into the instrument bore 22. The cylindrical flange 63 is accommodated in a partly cylindrical bearing surface 66 formed in the probe accommodating opening 65.

The primary pivot shaft 64 is pivotally carried in a pair of spaced apart bearing bores 67 formed by corresponding spaced apart pairs of bearing support plates 68 extending sidewardly from the sub-housing 20 and bearing support plates 69 extending upwardly from an inwardly directed carrier plate 73 extending inwardly into the hollow interior region 14 from the outer peripheral wall 12, see for example, FIGS. 13, 14, 19, 20, 21 and 22. Each of the bearing support plates 68 define 180° of the corresponding bearing bore 67, while the corresponding ones of the bearing support plates 69 define the other 180° of the corresponding bearing bores 67. The bearing support plates 68 and 69 are configured such that the bearing bores 67 pivotally engage and carry the primary pivot shaft 64 about the primary pivot axis 35.

A first transmission means, in this case a first drive transmission 74 is provided for deriving drive from the motion of the detecting probe 34 as the detecting probe 34 is urged distally from the first state to the second state, and for transmitting the derived drive to the proximal valve 40, for in turn urging the first and second valve plate members 44 and 45 from the withdrawn state to the engagement state. The first drive transmission 74 comprises a first transmission element 75, namely, a pair of first gear wheels 78 mounted fast on the primary pivot shaft 64 and spaced apart on respective opposite ends of the cylindrical annular flange 63 thereon, and second transmission elements, namely, a pair of first gear racks 80 and a pair of second gear racks 81, see in particular FIG. 24. The pairs of first and second gear racks 80 and 81 cooperate with and engage the first gear wheels 78, so that when the detecting probe 34 is urged distally from the first state to the second state resulting in the first gear wheels 78 rotating in the direction of the arrows D, the first gear racks 80 are urged in the direction of the arrows E, and the second gear racks 81 are urged in the direction of the arrows F, see FIG. 11.

The first gear racks 80 are located on respective opposite side portions 82 of a carrier plate 83, which is connected to the first valve plate member 44 by a pair of connecting members 84 extending between the carrier plate 83 and the first valve plate member 44. The second gear racks 81 are located on corresponding pairs of carrier arms 85 which extend on respective opposite sides of the sub-housing 20 from a carrier plate 87, which extends distally from the second valve plate member 45, and which connects the carrier arms 85 to the second valve plate member 45. The second gear racks 81 are located on the opposite side of the primary pivot axis 35, and in turn, on the opposite sides of the first gear wheels 78 to that on which the first gear racks 80 are located. In other words in this embodiment of the invention, the first gear racks 80 are located above the respective first gear wheels 78, and the second gear racks 81 are located below the respective first gear wheels 78. Thereby, as the first gear wheels 78 rotate in the direction of the arrows D in response to the detecting probe 34 being urged distally from the first state to the second state, the first gear racks 80 are urged in the direction of the arrows E and the second gear racks 81 are urged in the direction of the arrows F for in turn urging the first and second valve plate members 44 and 45 towards each other in the directions of the respective arrows C from the withdrawn state to the engagement state.

The carrier plate 87 is connected to the second valve plate member 45 by a pair of side connecting members 89, and the side connecting members 89 define with the carrier plate 87 and the second valve plate member 45 a first stabilising guide slot 90, see FIG. 8. The first stabilising guide slot 90 slideably engages a projecting portion 91 extending from the second distal side flange 54 for further guiding and stabilising the second valve plate member 45, see FIGS. 8 and 19.

The connecting members 84 which connect the carrier plate 83 to the first valve plate member 44 define a second stabilising guide slot 93 which slideably engages a projecting portion 94 projecting from the first distal side flange 50 for further guiding and stabilising the first valve plate member 44, see FIGS. 17 and 18.

An urging means comprising a resilient urging means provided by a compression spring 95 acting between the carrier plate 87 extending from the second valve plate member 45, and the sub-housing 20 is configured to resiliently urge the second valve plate member 45 into the withdrawn state, and in turn to urge the first valve plate member 44 into the withdrawn state, through the second gear racks 81, the first gear wheels 78 and the first gear racks 80. Accordingly, for so long as the detecting probe 34 is retained in the second state by the presence of the instrument 26 in the instrument bore 22, the first and second valve plate members 44 and 45 are retained in the engagement state. On withdrawal of the instrument 26 proximally through the instrument bore 22, as the distal end 38 of the instrument 26 moves proximally past the detecting probe 34, the urging action of the compression spring 95 urges the first and second valve plate members 44 and 45 from the engagement state into the withdrawn state. This in turn results in the first gear wheels 78 being rotated in the directions of the arrow H, see FIG. 13, thereby resulting in the detecting probe 34 being urged proximally from the second state to the first state, with the distal tip 37 of the detecting probe 34 following the distal end 38 of the instrument 26 as the instrument 26 is being withdrawn from the instrument bore 22. Therefore, prior to the distal end 38 of the instrument 26 reaching the proximal valve 40, the proximal valve 40 will be in the withdrawn state, thereby avoiding contact between the distal end 38 of the instrument 26 and the proximal valve 40.

One end of the compression spring 95 engages and is retained in a recess 97 formed in the carrier plate 87, and the other end of the compression spring 95 engages a cruciform shaped projection 98 extending from the sub-housing 20 so that the compression spring 95 is located and anchored between the carrier plate 87 and the sub-housing 20.

Turning now to the operation of the distal valve 28 from the closed state to the open state in response to the detecting probe 34 being urged distally from the first state to the second state, the distal valve member 29 comprises a circular disc valve plate member 100. The valve plate member 100 is carried on and extends substantially radially from a distal valve carrier shaft 102. The distal valve carrier shaft 102 defines the distal valve pivot axis 30, about which the valve plate member 100 is pivotal, and the distal valve carrier shaft 102 is pivotally carried in a pair of bearing bores 104 about the distal valve pivot axis 30. The bearing bores 104 are defined between respective pairs of bearing supports 105 and 106. The bearing supports 105 extend from the bearing support plates 68 which extend from the sub-housing 20. The bearing supports 106 are formed in the carrier plate 73 extending inwardly from the outer peripheral wall 12 of the main housing 9, see FIGS. 21 and 22. Each pair of bearing supports 105 and 106 define 180° of the corresponding bearing bore 104.

A second drive transmission 108 is provided for transmitting drive from the first drive transmission 74 to the distal valve carrier shaft 102, for in turn urging the distal valve member 29 from the closed state to the open state as the detecting probe 34 is urged from the first state to the second state. The second drive transmission 108 comprises a third transmission element, namely, a third gear rack 112 carried substantially centrally on a support member 113 secured to the carrier plate 87 and extending between the carrier arms 85. The third gear rack 112 faces distally from the support member 113, and moves in unison with the second gear racks 81. The third gear rack 112 cooperates with a fourth transmission element 111 carried on the distal valve carrier shaft 102 for transmitting drive from the first drive transmission 74 to the distal valve 28. The fourth transmission element 111 comprises a segment of a second gear wheel 110 mounted on the distal valve carrier shaft 102. The central axis of the second gear wheel segment 110 coincides with the distal valve pivot axis 30.

Accordingly, as the second gear racks 81 are being urged in the direction of the arrow F resulting from rotation of the first gear wheels 78 in the direction of the arrow D, the third gear rack 112 is urged also in the direction of the arrow F for in turn urging the second gear wheel segment 110 in the direction of the arrow K, for in turn urging the distal valve member 29 from the closed state to the open state, see FIG. 6. Therefore, as the detecting probe 34 is urged distally from the first state to the second state by the instrument 26 being urged distally through the instrument bore 22, the distal valve 28 is urged from the closed state to the open state, so that prior to the distal end 38 of the instrument 26 reaching the distal valve 28, the distal valve 28 has been urged into the open state, thereby avoiding contact between the instrument 26 and the distal valve 28, see FIG. 25.

Since the third gear rack 112 is carried on the support member 113, which is secured to the carrier plate 87, and since the compression spring 95 acts between the sub-housing 20 and the carrier plate 87 for urging the first and second valve plate members 44 and 45 from the engagement state to the withdrawn state, the distal valve member 29 is urged from the open state to the closed state by the action of the compression spring 95 through the third gear rack 112 and the second gear wheel segment 110, as the detecting probe 34 is being urged proximally under the action of the compression spring 95 from the second state to the first state.

A second sealing means comprising an annular seal 115 is located on the sub-housing 20 adjacent the distal end 21 thereof extending around the instrument bore 22, and defines a valve seat 114 of the distal valve 28. The annular seal 115 cooperates with the valve plate member 100 of the distal valve 28 for forming an airtight seal between the valve seat 114 and the valve plate member 100 when the distal valve 28 is in the closed state. Thereby, leakage of insufflating and other gases from the cavity of a subject being insufflated through the instrument bore 22 is prevented by the distal valve 28, when no instruments are extending through the instrument bore 22.

The distal open mouth 16 defined by the outer peripheral wall 12 of the main housing 9 sealably engages the proximal end 4 of the trocar 2.

A securing means for releasably securing the valve mechanism 3 to the proximal end 4 of the trocar cannula 2 comprises a pair of engagement slots 122 formed in the outer peripheral wall 12 of the main housing 9 on respective opposite sides thereof for releasably engaging a corresponding pair of resilient securing members 124, which extend proximally from the trocar cannula 2 on respective opposite sides thereof adjacent the proximal end 4 thereof. The securing members 124 are of a resilient material, and terminate in engagement lugs 126 for releasably engaging the engagement slots 122, for in turn securing the valve mechanism 3 to the trocar cannula 2. A pair of guide grooves 123 in the outer peripheral side wall 12 extending proximally from the distal end 11 thereof guide the securing members 124 and in turn the engagement lugs 126 into the engagement slots 122. A gap 127 between a portion 128 of the outer peripheral wall 12 forming each engagement slot 122 and an inner surface 129 of the corresponding guide groove 123 is of sufficient width to accommodate the engagement lug 126 of the corresponding securing member 124 through the guide groove 123 and into the engagement slot 122.

A third sealing means to form a seal between the housing of the valve mechanism 1 and the proximal end 4 of the trocar cannula 2, in this embodiment of the invention, is formed by virtue of the outer peripheral wall 12 adjacent the distal open mouth 16 thereof being a tight sliding fit on the proximal end 4 of the trocar cannula 2. However, it will be readily apparent to those skilled in the art that any other suitable third sealing means, for example, an O-ring extending around and between the peripheral wall 12 of the valve mechanism 3 and the wall of the trocar cannula 2 adjacent the proximal end 4 thereof could also be provided, or any other suitable third sealing means.

In use, the valve mechanism 3 is secured to the trocar cannula 2 by engaging the proximal end 4 of the trocar cannula 2 in the distal open mouth 16 of the valve mechanism 3, and aligning the guide grooves 123 formed in the outer peripheral wall 12 of the main housing 9 with the securing members 124. The main housing 9 is urged distally onto the proximal end 4 of the trocar cannula 2 with the securing members 124 and the engagement lugs 126 being guided through the guide grooves 123 until the engagement lugs 126 engage in the engagement slots 122, thereby securing the valve mechanism 3 to the proximal end 4 of the trocar cannula 2. With the valve mechanism 3 securing to the trocar cannula 2, the assembly 1 of the trocar cannula 2 and the valve mechanism 3 is ready for use.

While the instrument bore 22 is free of instruments, the detecting probe 34 is urged by the compression spring 95 through the second gear racks 81 and the first gear wheels 78 into the first state. Thus, in the first state of the detecting probe 34, the instrument bore 22 is closed by the distal valve 28, and the first and second proximal valve members 41 and 42 are in the withdrawn state. On insertion of an instrument, for example, the instrument 26 into the instrument bore 22 of the valve mechanism 3, on the distal end 38 of the instrument 26 engaging the detecting probe 34, further urging of the instrument 26 distally through the instrument bore 22 results in the detecting probe 34 being urged distally from the first state to the second state. This in turn results in the distal valve 28 being operated from the closed state to the open state to accommodate the instrument 26 unimpeded from the instrument bore 22 into the instrument bore 27 of the trocar cannula 2. Additionally, the urging of the detecting probe 34 distally from the first state to the second state, results in the first and second proximal valve members 41 and 42 of the proximal valve 40 being urged from the withdrawn state to the engagement state into sealing engagement with the instrument 26, to thereby minimise leaking of insufflating and other gases from a cavity of a subject being insufflated and into which the trocar 2 extends.

For so long as the instrument 26 remains in the instrument bore 22, the instrument 26 retains the detecting probe 34 in the second state against the action of the compression spring 95, and in turn, the distal valve 28 is retained in the open state, and the first and second proximal valve members 41 and 42 of the proximal valve 40 are retained in the engagement state sealably engaging the instrument 26.

On withdrawal of the instrument 26 through the instrument bore 22, as the distal end 38 of the instrument 26 passing proximally reaching the detecting probe 34, further proximal movement of the instrument 26 through the instrument bore 22 results in the detecting probe 34 following the distal end 38 of the instrument 26 in the proximal direction from the second state to the first state under the action of the compression spring 95. The action of the compression spring 95 urging the detecting probe 34, results in the distal valve 28 being urged into the closed state, thereby preventing leaking of insufflating gases through the instrument bore 22, and also results in the first and second proximal valve members 41 and 42 of the proximal valve 40 being urged from the engagement state to the withdrawn state. Once the detecting probe 34, following the distal end 38 of the instrument 26, has reached the first state, the distal valve 28 is in the closed state, and the proximal valve 40 is in the withdrawn state. Therefore, the proximal valve 40 is in the withdrawn state prior to the distal end 38 of the instrument 26 reaching the proximal valve 40, and the distal end 38 of the instrument 26 passes through the proximal valve 40 unimpeded and without contacting the proximal valve 40.

Accordingly, the valve mechanism 3 according to the invention provides a particularly important advantage, in that the leakage of insufflating gas and other gases from a cavity of a subject being insufflated, which would otherwise leak proximally through a trocar is eliminated, and if not fully eliminated is eliminated to the extent that such leakage is negligible. This advantage is achieved by virtue of the fact that the instrument bore 22 through the valve mechanism 3 is closed by the distal valve 28 until an instrument is inserted through the valve mechanism 3. The distal valve 28 remains in the closed state until it has been opened by the action of the distal end 38 of the instrument 26 on the detecting probe 34 urging the detecting probe 34 from the first state to the second state. Once the detecting probe 34 has reached the second state, the distal valve 28 has been urged into the open state, thereby allowing the instrument to be urged through the instrument bore 22 and into the instrument bore 27 of the trocar cannula 2 unimpeded past the distal valve 28. As the detecting probe 34 is being urged distally from the first state to the second state, the first and second proximal valve members 41 and 42 of the proximal valve 40 are being urged from the withdrawn state to the engagement state to seal against the instrument in the instrument bore 22 of the valve mechanism 3, simultaneously as the distal valve 28 is being urged into the open state. The sealing action of the first and second proximal valve members 41 and 42 of the proximal valve 40 by sealing against the instrument 26 prevent leakage of insufflating and other gases proximally through the instrument bore 22. Thus, when the distal valve 28 is open, the proximal valve 40 is closed sealably engaging the instrument 26 and closing the instrument bore 22, and vice versa, so that at virtually all times the instrument bore 22 through the valve mechanism 3 is closed by either the distal valve 28 or by the proximal valve 40 sealably engaging the instrument 26.

A further important advantage of the invention is achieved when the instrument being inserted through the valve mechanism 3 is a laparoscope. By virtue of the fact that the distal valve 28 is operated into the open state before the distal end of the instrument 26, such as a laparoscope, reaches the distal valve 28, the laparoscope can pass through the distal valve 28 unimpeded and without contact with the distal valve 28. This thereby, avoids any danger of tissue, blood or other material, which may have been previously deposited on the distal valve member 29 during withdrawal of such material previously from the cavity of the subject, contaminating the lens at the distal end of the laparoscope, which would otherwise occlude the lens, and prevent image capturing by an image capturing device through the lens of the laparoscope.

Additionally, by virtue of the fact that the first and second proximal valve members 41 and 42 of the proximal valve 40 are urged into the withdrawn state and are retained therein by the action of the spring 95 until the distal end of an instrument being urged into the instrument bore 22 of the valve mechanism 3 has passed the proximal valve 40, there is no danger of any tissue or other material which may have been deposited on the first and second proximal valve members 41 and 42 contaminating the lens of a laparoscope as it is being urged into the instrument bore 22 of the valve mechanism 1. Furthermore, by virtue of the fact that the first and second valve members 41 and 42 of the proximal valve 40 are urged into the withdrawn state prior to the distal end of an instrument reaching the proximal valve 40 as the instrument is being withdrawn through the instrument bore 22, there is little or no danger of any tissue or other material at the distal end of an instrument being withdrawn through the valve mechanism being deposited on the first and second proximal valve members 41 and 42.

Referring now to FIGS. 26 to 28, there is illustrated a valve mechanism according to another embodiment of the invention indicated generally by the reference numeral 300. The valve mechanism 300 is substantially similar to the valve mechanism 3 described with reference to FIGS. 1 to 25, and similar components are identified by the same reference numerals. The valve mechanism 300 comprises all the components of the valve mechanism 3, and in addition, the valve mechanism 300 comprises a plurality of collection ports 302 located in the sub-housing 20 proximally of the proximal valve 40 and communicating with the instrument bore 22 adjacent the proximal end 23 thereof. The collection ports 302 are equi-spaced apart circumferentially around the instrument bore 22, and are configured for applying a vacuum thereto for drawing any insufflating gases and other gases which may escape past the proximal valve 40, in order to avoid any such insufflating and other gases passing from the proximal end 23 of the instrument bore 22 into the environment. An annular gallery 304 extends in the sub-housing 20 around the instrument bore 22 with which the collection ports 302 communicate. The annular gallery 304 communicates with the hollow interior region 14 defined by the main housing 9, which is completely sealed. A connection port 305 extending through and from the outer peripheral wall 12 of the main housing 9 communicates with the hollow interior region 14. The connection port 305 is configured for connecting to a vacuum system (not shown) for applying a vacuum to the hollow interior region 14, which in turn is applied to the gallery 304, and in turn to the collection ports 302 through the gallery 304 for drawing any escaping insufflating and other gases from the instrument bore 22 adjacent the proximal end 23 thereof. Any suitable vacuum system may be used.

Use of the valve mechanism 300 is similar to that of the valve mechanism 3. The valve mechanism 300 is releasably secured to the proximal end of a trocar cannula, similar to the trocar cannula 2 described with reference to FIGS. 1 to 25. The connection port 305 is then connected to a suitable vacuum system for applying a vacuum to the collection ports 302 for drawing any escaping insufflating and other gases from the instrument bore 22. The vacuum system typically would be configured to draw the insufflating and other gases from the collection ports 302 and filter the insufflating and other gases downstream of the connection port 305 in order to filter out any pathogens, viruses, infections, and other contaminating particles and elements from the gases prior to dispersing the filtered gases into the environment.

Referring now to FIGS. 29 to 35, there is illustrated a valve mechanism according to another embodiment of the invention indicated generally by the reference numeral 310 for connecting to a trocar cannula 312 for preventing or at least minimising leakage of insufflating and other gases into the environment from the trocar cannula 312. The valve mechanism 310 is substantially similar to the valve mechanism 3 described with reference to FIGS. 1 to 25, and similar components are identified by the same reference numerals.

The valve mechanism 310 comprises all the components of the valve mechanism 3. The main difference between the valve mechanism 310 and the valve mechanism 3 is that the valve mechanism 310 as well as being configured for use with a trocar cannula of the type of the trocar cannula 2 described with reference to FIGS. 1 to 25, the valve mechanism 310 is also configured for use with the trocar cannula 312 illustrated in FIGS. 31 and 32.

Before describing the valve mechanism 310, the trocar 312 will first be described.

The trocar cannula 312 is of the type which is similar to the trocar cannula 2 described with reference to FIGS. 1 to 25, with the exception that an access valve 314 is located in an instrument bore 316 of the trocar cannula 312 adjacent a proximal end 315 thereof. Many types of access valves may be provided in the proximal end of the instrument bore 316 of a trocar cannula 312, one example of which is a duckbill valve 318, illustrated in FIGS. 31 and 32. Such duckbill valves as the duckbill valve 318 and other such access valves of trocar cannulae will be well known to those skilled in the art.

Briefly, the duckbill valve 318 illustrated in FIGS. 31 and 32 comprises a flexible resilient material which under its own inherent resilience is urged into a normally closed state with a pair of opposite valving portions 319 sealably abutting each other along respective abutment sealing edges 320. The valving portions 319 are configured to yield into an open state under the pressure of an instrument being urged against them so that the valving portions 319 part along the abutment edges 320 for accommodating an instrument therethrough. The abutting edges 320 sealably engage the instrument partly around its circumferential surface in order to minimise the leakage of insufflating and other gases in a proximal direction from the instrument bore 316 of the trocar 312. An annular rim 323 of the duckbill valve 318 is provided with a circumferentially extending recess 321 which extends around the rim 323. The recess 321 is configured typically, to releasably engage an annular ridge 322 extending circumferentially around the trocar cannula 312 and into the instrument bore 316 adjacent the proximal end 315 thereof for releasably securing the duckbill valve 318 in the trocar cannula 312. As discussed above such duckbill valves 318 and other variations thereof, as well as other such access valves, will be well known to those skilled in the art, and further description should not be required.

Turning now to the valve mechanism 310, the valve mechanism 310 as mentioned above is similar to the valve mechanism 3 described with reference to FIGS. 1 to 25 and comprises all the components of the valve mechanism 3. In addition, the valve mechanism 310 comprises an operating means for operating the duckbill valve 318 from the closed state to the open state. The operating means comprises a passive operating means provided by a passive operating member 325, and an active operating means provided by the valve plate member 100 of the distal valve 28. The passive operating member 325 extends distally from the carrier plate 73 of the main housing 9 for engaging and extending through the duckbill valve 318 as the valve mechanism 310 is being engaged on the proximal end 315 of the trocar cannula 312, for in turn urging one half of the duckbill valve 318 from the closed state into the open state. In this embodiment of the invention the passive operating member 325 comprises an elongated operating member of semi-circular transverse cross-section extending from a proximal end 324 to a distal end 327. The proximal end 324 of the passive operating member 325 is secured to the carrier plate 73, and the distal end 327 of the passive operating member 325 is engageable with and extends through the duckbill valve 318 when the valve mechanism 310 is secured to the proximal end 315 of the trocar cannula 312. The passive operating member 325 extends from the carrier plate 73, so that a centre of radius of an inner surface 326 of the passive operating member 325 coincides with the main central axis 25 defined by the instrument bore 22.

The radius of the inner surface 326 of the passive operating member 325 is greater than the radius of the instrument bore 22, and is also greater than the radius of the outer periphery of the valve plate member 100 of the distal valve 28, so that the passive operating member 325 is clear of the valve plate member 100 of the distal valve 28, in order not to impede the operation of the distal valve plate member 100 pivoting between the open and closed states thereof.

Corners 328 adjacent the distal end 327 of the passive operating member 325 are radiused so that the passive operating member 325 progressively engages and opens one half of the duckbill valve 318 as the valve mechanism 310 is being engaged on the proximal end 315 of the trocar 312.

The valve plate member 100 of the distal valve 28 is located in the housing 7 to extend into and engage the duckbill valve 318 as the valve plate member 100 is being pivoted from the closed state to the open state, and to therefore act as the active operating means for urging one half of the duckbill valve 318 from the closed state to the open state as the valve plate member 100 is being pivoted from the closed state to the open state.

The passive operating member 325 is located on the opposite side of the instrument bore 22 to that on which the distal valve carrier shaft 102 of the distal valve 28, is located, so that the valve plate member 100 of the distal valve 28 actively cooperates with the passive operating member 325 to fully open the duckbill valve 318 as the distal valve plate member 100 is being urged from the closed state to the open state, in response to the detecting probe 34 being urged distally from the first state to the second state by the distal end 38 of an instrument 26 being urged distally through the instrument bore 22. The diameter of the valve plate member 100 of the distal valve 28 is such, and its location in the housing 7 of the valve mechanism 310 is such, that when the distal valve 28 is in the open state as illustrated in FIG. 34, the valve plate member 100 extends into the duckbill valve 318 to cooperate with the passive operating member 325 to fully open the duckbill valve 318.

In use, the valve mechanism 310 is secured to the proximal end 315 of the trocar cannula 312 in a similar manner as the valve mechanism 3 is secured to the proximal end 4 of the trocar cannula 2. As the valve mechanism 310 is being urged onto the proximal end 315 of the trocar cannula 312, the passive operating member 325 engages and extends through the duckbill valve 318 thereby partly opening the duckbill valve 318. For so long as the valve mechanism 310 is secured to the trocar cannula 312 the passive operating member 325 remains extending through the duckbill valve 318 thereby retaining the duckbill valve 318 partly opened.

When an instrument such as the instrument 26 is entered into the instrument bore 22 of the valve mechanism 310 and is being urged distally therethrough, as the distal end 38 of the instrument 26 engages the detecting probe 34 in the first state, further movement of the instrument 26 distally through the instrument bore 22 urges the detecting probe 34 from the first state to the second state. The action of the detecting probe from the first state to the second state results in the proximal valve 40 being urged from the withdrawn state into the engagement state for sealably engaging the instrument, and also results in the distal valve 28 being urged from the closed state into the open state with the valve plate member 100 extending distally into the duckbill valve 318. The cooperating action of the distal valve 28 being urged into the open state with the passive operating member 325 fully opens the duckbill valve 318, and retains the duckbill valve 318 in the open state for so long as the detecting probe 34 is retained in the second state by the presence of the instrument 26 in the instrument bore 22. Accordingly, prior to the distal end 38 of the instrument 26 reaching the duckbill valve 318, the duckbill valve 318 is fully opened, and thereby, the instrument 26 can pass unimpeded through the duckbill valve 318 without making any contact therewith.

Thus, the advantage of the cooperating action of the valve plate member 100 of the distal valve 28 acting as the active operating member with the passive operating member 325 is that by virtue of the fact that the duckbill valve 318 is retained open by the cooperating action of the valve plate member 100 and the passive operating member 325, there is no danger of any biological or other matter which may have collected on the abutting sealing edges 320 of the duckbill valve 318 coming into contact and contaminating the instrument 26. This is a particularly important advantage when the instrument comprises a laparoscope, since any contamination of a lens on the distal end of a laparoscope by tissue, blood and other deposits of material from the cavity of a subject which may collect on the abutting sealing edges 320 of the duckbill valve 318, if that material were transferred by contact therewith to the lens of a laparoscope, would result in the lens thereof being occluded. Any occlusion or partial occlusion of a lens of a laparoscope would prevent or hinder vision therethrough, thereby preventing image capture by an image capturing device through the lens of the laparoscope.

Otherwise, the valve mechanism 310 and its use is similar to the valve mechanism 3 described with reference to FIGS. 1 to 25.

Referring now to FIGS. 36 to 39, there is illustrated a valve mechanism according to another embodiment of the invention indicated generally by the reference numeral 330 for minimising leakage of insufflating and other gases from the cavity of a subject proximally through a trocar. The valve mechanism 330 is substantially similar to the valve mechanism 3 described with reference to FIGS. 1 to 25, and similar components are identified by the same reference numerals. The valve mechanism 330 comprises all the components of the valve mechanism 3. In fact, the valve mechanism 330 is substantially similar to the valve mechanism 310.

The valve mechanism 330 comprises an operating means, which in this embodiment of the invention comprises a passive operating means for operating a duckbill valve of a trocar cannula, such as the duckbill valve 318 of the trocar cannula 312 from the closed state to the open state. The passive operating means in this embodiment of the invention comprises a passive operating member 332, which extends distally from the main housing 9, for engaging and opening the duckbill valve 318 in a trocar cannula 312 as the valve mechanism 330 is engaged on the proximal end 315 of the trocar cannula 312. The passive operating member 332 comprises a tubular operating member 334 of circular transverse cross-section, which extends distally from an inwardly directed stepped flange 335. The stepped flange 335 extends inwardly from and around the outer peripheral wall 12 of the main housing 9 and into the hollow interior region 14. The tubular operating member 334 defines a longitudinally extending central axis 333 which coincides with the main central axis 25 defined by the instrument bore 22.

The inner diameter of the stepped flange 335 and the inner diameter of the tubular operating member 334 and their spacing from the distal valve 28 is such that neither the stepped flange 335 nor the tubular operating member 334 impede the operation of the valve plate member 100 of the distal valve 28 as it pivots between the open and closed states. The valve plate member 100 is pivotal into the open state without coming into contact with either the stepped flange 335 or the tubular member 334.

The length of the tubular operating member 334 from the stepped flange 335 to the distal end 336, is such that when the valve mechanism 330 is fully engaged with, for example, the proximal end 315 of the trocar cannula 312, the tubular operating member 334 extends through the duckbill valve 318 thereby retaining the duckbill valve 318 in the fully open state and also shielding the instrument 26 from the duckbill valve 318.

Otherwise, the valve mechanism 330 is similar to the valve mechanism 3 described with reference to FIGS. 1 to 25, and its use is likewise similar, with the exception that as the valve mechanism 330 is being urged into engagement with the proximal end of a trocar cannula the operating member 332 engages and opens the duckbill valve or other such valve therein.

Referring now to FIGS. 40 to 43, there is illustrated a valve mechanism according to a further embodiment of the invention indicated generally by the reference numeral 340 for minimising escape of insufflating and other gases from a trocar. The valve mechanism 340 is substantially similar to the valve mechanism 3, and similar components are identified by the same reference numerals. The main difference between the valve mechanism 340 and the valve mechanism 3 lies in the distal valve 28. The distal valve 28, which as well as sealably closing the instrument bore 22, also acts as an active operating means, as will be described below, for operating an access valve located in the proximal end of a trocar cannula, for example, a duckbill valve 318, from a closed state to an open state, as the distal valve 28 is being operated from the closed state to the open state. In this embodiment of the invention the distal valve 28 comprises a pair of valve plate members, namely, a first valve plate member 341 and a second valve plate member 342. The first and second valve plate members 341 and 342 are pivotal from a closed state illustrated in FIGS. 40 and 42 closing the instrument bore 22 to an open state illustrated in FIGS. 41 and 43, allowing passage of an instrument unimpeded therethrough. In the open state, as well as the first and second valve plate members 341 and 342 allowing passage of an instrument unimpeded therethrough, the first and second valve plate members 341 and 342 are also configured to act as the active operating means for operating the duckbill valve 318 into the open state, and for retaining the duckbill valve 318 in the open state for so long as the valve plate members 341 and 342 are in the open state.

The first and second valve plate members 341 and 342 comprise respective semi-circular first and second disc members 343 and 344 which in the closed state sealably engage the second seal 115 of the valve seat 114, and sealably abut each other along respective distal transverse edges 345 of the disc members 343 and 344 for sealably closing the instrument bore 22. The first disc member 343 extends from the distal valve carrier shaft 102, and is operated between the open state and the closed state by the distal valve carrier shaft 102, which in turn is operated by the cooperating action between the third gear rack 112 and the second gear wheel segment 110, in a similar manner as the valve plate member 100 of the distal valve 28 of the valve mechanism 3 is operated between the open and closed states.

Turning now to the second disc member 344, the second disc member 344 is carried on a supplementary valve carrier shaft 347 which is pivotally carried in a pair of semi-circular bearing bores 348, one of which is formed in the carrier plate 73 of the main housing 9, and the other of which is formed in a carrier member (not shown) extending from the sub-housing 20. The arrangement of the bearing bores 348 in the carrier plate 73 and in the carrier member (not shown) extending from the sub-housing 20 is substantially similar to the bearing bores 104 in the carrier plate 73 and the bearing support plates 105 described with reference to the valve mechanism 3 of FIGS. 1 to 25. The supplementary valve carrier shaft 347 is carried in the bearing bores 348, and defines a supplementary distal valve pivot axis 349 about which the second disc member 344 is pivotal. The supplementary distal valve pivot axis 349 extends parallel to the distal valve pivot axis 30 defined by the distal valve carrier shaft 102. Additionally, the supplementary distal valve pivot axis 349 of the supplementary carrier shaft 347 is located on the opposite side of the instrument bore 22 to that on which the distal valve pivot axis 30 is located.

A third drive transmission means comprising a third drive transmission 350 is provided for transmitting drive from the detecting probe 34 to the supplementary carrier shaft 347 as the detecting probe 34 is urged distally from the first state to the second state, for in turn urging the second disc member 344 from the closed state to the open state, simultaneously as the first disc member 343 is being urged from the closed state to the open state. The third drive transmission 350 comprises a fifth transmission element, namely, a fourth gear rack 352 which is carried on a gear rack carrier 353 extending distally from the carrier plate 83 on which the first gear racks 80 are carried. The fourth gear rack 352 extends parallel with the first gear racks 80, and is co-operable with a sixth transmission element, namely, a segment of a third gear wheel 354, which is carried fast on the supplementary carrier shaft 347. Accordingly, as the detecting probe 34 is urged distally from the first state to the second state, the first and second distal valve numbers 341 and 342 are urged from the closed state to the open state by the cooperating action of the third gear rack 112 with the second gear wheel segment 110 and the cooperating action of the fourth gear rack 352 with the third gear wheel segment 354. Additionally, as the detecting probe 34 is being urged from the first state to the second state, the first and second proximal valve members 41 and 42 are urged from the withdrawn state to the engagement state.

Pairs of spaced apart operating members 355 extend from the respective first and second disc members 343 and 344 adjacent the distal transverse edges 345 thereof in a generally radial direction relative to the corresponding distal valve axis 30 and the supplementary distal valve axis 349, see FIGS. 40 and 41. The pairs of the operating members 355 are provided for engaging the duckbill valve 318 in the trocar 312 for urging the duckbill valve 318 from the closed state into the open state as the first and second disc members 343 and 344 are urged from the closed state to the open state. The pairs of operating members 353 extending from the respective first and second disc members 343 and 344 are provided at appropriate spacing, so that the pair of the operating members 355 on the first disc member 343 do not interfere with the pair of operating members 355 on the second disc member 344, when the first and second disc members 343 and 344 are in the closed state. Additionally, the operating members 355 extend from the first and second disc members 343 and 344 a sufficient distance to open the duckbill valve 318 when the first and second disc members 343 and 344 are in the open state.

In use, the valve mechanism 340 is secured to the proximal end 315 of the trocar cannula 312 in a similar manner as the valve mechanism 3 is secured to the trocar cannula 2 of the assembly 1 of FIGS. 1 to 25. As an instrument 26 is being urged through the instrument bore 22 of the valve mechanism 340, on the distal end 38 of the instrument 26 engaging the detecting probe 34, further movement of the instrument 26 distally in the instrument bore 22 urges the detecting probe 34 distally from the first state to the second state. As the detecting probe 34 is urged from the first state to the second state, the proximal valve 40 is operated from the withdrawn state to the engagement state sealably engaging the instrument, and the first and second valve plate members 341 and 342 of the distal valve 28 are urged from the closed state to the open state. As the first and second valve plate members 341 and 342 are being urged from the closed state to the open state, the action of the first and second disc members 343 and 344 and the operating members 355 on the duckbill valve 318, urges the duckbill valve 318 from the closed state to the open state.

Accordingly, prior to the distal end 38 of the instrument 26 reaching the distal end 24 of the instrument bore 22, the first and second distal valve members 341 and 342 of the distal valve 28 are in the open state, and additionally, the duckbill valve 318 is held in the open state by the disc members 343 and 344 and the operating members 355. Therefore, the instrument 26 can pass from the instrument bore 22 in the valve mechanism 340 into the instrument bore 316 of the trocar cannula 312 unimpeded without making contact with either the first and second distal valve members 341 and 342 or the duckbill valve 318. Thus, there is no danger of the lens adjacent the distal end of an instrument, for example, a laparoscope being contaminated with any deposits which may have been deposited on the duckbill valve 318.

Otherwise, the valve mechanism 340 and its operation is similar to that of the valve mechanism 3 described with reference to FIGS. 1 to 25.

It will be appreciated that the valve mechanisms 310, 330 and 340 as well as being suitable for use with a trocar cannula of the type of the trocar cannula 312 are also suitable for use with a trocar cannula of the type of the trocar cannula 2.

Referring now to FIGS. 44 to 47 there is illustrated a valve mechanism according to a further embodiment of the invention indicated generally by the reference numeral 360 for securing to a proximal end 315 of a trocar cannula 312 for preventing escape of insufflating and other gases passing proximally through the instrument bore 316 of the trocar cannula 312 and into the environment. The valve mechanism 360 is substantially similar to the valve mechanism 3 described with reference to FIGS. 1 to 25, and similar components are identified by the same reference numerals. The valve mechanism 360 includes all the components of the valve mechanism 3 described with reference to FIGS. 1 to 25, with the exception that in this embodiment of the invention the distal valve 28 is omitted. Since the distal valve 28 is omitted in the valve mechanism 360, the distal valve drive shaft, as well as the third gear rack and the second gear wheel segment are also omitted. However, the valve mechanism 360 comprises the proximal valve, which although not shown in FIGS. 44 to 47, is similar to the proximal valve 40 of the valve mechanism 3, described with reference to FIGS. 1 to 25. The proximal valve 40 of the valve mechanism 360 comprises the first and second proximal valve members 41 and 42, which in turn are driven by the first gear wheels 78 on the primary pivot shaft 64 for operating the first and second valve members 41 and 42 from the withdrawn state to the engagement state as the detecting probe 34 is urged distally from the first state to the second state.

An operating means, in this case an active operating means for operating the duckbill valve 318 of the trocar cannula 312 is provided and comprises an active operating member 361. The operating member 361 is operable between a disengaged state illustrated in FIGS. 44 and 46, disengaged from the duckbill valve 318, and an engagement state illustrated in FIGS. 45 and 47 extending into and through the duckbill valve 318 for opening and retaining the duckbill valve 318 in the open state. In the engagement state, the operating member 361 retains the duckbill valve 318 in the open state and also shields an instrument, passing from the instrument bore 22 into the instrument bore 316 of the trocar cannula 312, from the duckbill valve 318, so that the instrument passes unimpeded through the duckbill valve 318. The operating member 361 extends from a proximal end 362 to a distal end 363, and is slideably mounted externally on the sub-housing 20 between the disengaged state and the engagement state. The operating member 361 is urged from the disengaged state to the engagement state in response to the detecting probe 34 being urged distally from the first state to the second state. A third drive means for urging the operating member 361 from the disengaged state to the engagement state, in response to the detecting probe 34 being urged distally from the first state to the second state, comprises a pair of spaced apart drive members 365, which extend radially from the primary pivot shaft 64 on respective opposite sides of the sub-housing 20. The drive members 365 are engageable with an engagement flange 367 extending radially outwardly from and circumferentially around the operating member 361 adjacent a proximal end 362 thereof. The drive members 365 are configured to engage the engagement flange 367 with the operating member 361 in the disengaged state when the detecting probe 34 is in the first state, so that when the detecting probe 34 has been urged from the first state to the second state, the operating member 361 is urged from the disengaged state to the engagement state engaging and extending through the duckbill valve 318 with the duckbill valve 318 in the open state.

In this embodiment of the invention the urging means for urging the first and second proximal valve members 41 and 42 of the proximal valve 40 from the engagement state to the withdrawn state instead of being provided by a compression spring 95 is provided by a compression spring 368. The compression spring 368 acts between the carrier plate 73 of the main housing 9 and the engagement flange 367 of the operating member 361. The compression spring 368 is configured to urge the operating member 361 from the engagement state to the disengaged state, and in turn to urge the detecting probe 34 from the second state to the first state through the action of the operating member 361 on the drive members 365, which rotate the primary pivot shaft 64 in the direction of the arrow L. The rotation of the primary pivot shaft 64 in the direction of the arrow L, results in the first and second proximal valve members 41 and 42 of the proximal valve 40, which are not illustrated in FIGS. 44 to 47, being urged from the engagement state to the withdrawn state. Accordingly, on the instrument being withdrawn through the instrument bore 22, as the distal end of the instrument is passing the detecting probe 34 in a proximal direction, the urging action of the compression spring 368 on the operating member 361 results in the detecting probe 34 being urged from the second state to the first state, as the detecting probe 34 follows the distal end of the instrument as it passes the detecting probe 34. This in turn results in the operating member 361 being urged from the engagement state to the disengaged state, and the first and second proximal valve members 41 and 42 of the proximal valve 40 being urged from the engagement state to the withdrawn state.

In use, the valve mechanism 360 is engaged on the proximal end 315 of the trocar cannula 312 in a manner similar to that in which the valve mechanism 3 is secured to the proximal end 4 of the trocar cannula 2 of the assembly 1 described with reference to FIGS. 1 to 25. As an instrument, such as, the instrument 26 is being urged into and distally through the instrument bore 22, on the distal end 38 of the instrument 26 engaging the detecting probe 34, further urging of the instrument 26 distally in the instrument bore 22 results in the detecting probe 34 being urged distally from the first state to the second state. This in turn results in the first and second proximal valve members 41 and 42 of the proximal valve 40 being urged from the withdrawn state to the engagement state engaging the instrument 26 in the instrument bore 22. Additionally, as the detecting probe 34 is being urged from the first state to the second state, the drive members 365 engaging the engagement flange 367 of the operating member 361 urge the operating member 361 from the disengaged state to the engagement state, thereby urging the operating member 361 into and through the duckbill valve 318 for in turn operating the duckbill valve 318 into the open state and retaining it in the open state. Accordingly, prior to the distal end 38 of the instrument 26 reaching the distal end 24 of the instrument bore 22, the duckbill valve 318 has been fully opened by the operating member 361, which also shields the instrument 26 from the duckbill valve 318. Accordingly, the instrument 26 may be urged from the instrument bore 22 of the valve mechanism 360 into the instrument bore 316 of the trocar cannula 312 unimpeded by the duckbill valve 318, and shielded therefrom by the operating member 361.

Since the instrument 26 in the instrument bore 22 retains the detecting probe 34 in the second state, the operating member 361 is retained in the engagement state, and the proximal valve 40 is retained in the engagement state, for so long as the instrument 26 remains in the instrument bore 22.

On withdrawal of the instrument 26 through the instrument bore 22, once the distal end 38 of the instrument 26 passes the detecting probe 34 in the second state, moving proximally, the detecting probe 34, under the action of the compression spring 368 acting on the operating member 361, and in turn on the drive members 365, follows the distal end 38 of the instrument 26 as the distal end 38 of the instrument 26 is being urged proximally past the detecting probe 34. The urging action of the compression spring 368 urging the operating member 361 from the engagement state to the disengaged state also urges the first and second proximal valve members 41 and 42 of the proximal valve 40 from the engagement state to the withdrawn state through the drive members 365, the first gear wheel 78 and the first gear rack 80.

The omission of the distal valve 28 from the valve mechanism 360 does not result in any disadvantages of the valve mechanism 360. By virtue of the fact that the duckbill valve 318 of the trocar cannula 312 remains in the closed state until it is operated into the open state by the operating member 361 as the detecting probe 34 is urged distally from the first state to the second state, the duckbill valve 318 essentially takes the place of the distal valve 28.

Otherwise, the valve mechanism 360 and its use is similar to the valve mechanism 3 described with reference to FIGS. 1 to 25.

While the valve mechanism 3 and the valve mechanisms 310, 330, 340 and 360 have been described without collecting ports 302 similar to the collecting ports 302 of the valve mechanism 300 for collecting insufflating and other gases which may leak proximally past the proximal valve 40 by a vacuum applied to the collecting ports 302, it will be readily understood by those skilled in the art that each of the valve mechanisms 3, 310, 330, 340 and 360 may be provided with such collecting ports adjacent but proximal of the proximal valve 40.

Referring now to FIGS. 48 and 49 there is illustrated a portion of a valve mechanism according to another embodiment of the invention indicated generally by the reference numeral 130. The valve mechanism 130 is illustrated in diagrammatic form only, and only parts of the valve mechanism 130 are illustrated. The valve mechanism 130 is provided with a housing (not shown) within which the components illustrated in FIGS. 48 and 49 are located. The housing (not shown) of the valve mechanism 130 is configured for sealably securing to a trocar cannula, similar to the trocar cannula 2 adjacent the distal end 4 thereof. A sub-housing 131 secured to a main housing (not shown) of the valve mechanism 130 and extending though the main housing (not shown) defines an instrument bore 132 for accommodating an instrument 26, for example, a laparoscope therethrough to an instrument bore 27 of the trocar cannula 2. The instrument bore 132 defines a longitudinally extending main central axis **132*a***.

A distal valve 134 which is located adjacent a distal end 133 of the instrument bore 132, is substantially similar to the distal valve 28 of the valve mechanism 3, and is carried on a distal valve carrier shaft 135. The distal valve carrier shaft 135 is pivotally carried in the sub-housing 131 about a distal valve pivot axis **135*a*, in a manner not shown, but substantially similar to the manner in which the distal valve carrier shaft 102 is pivotally carried in the sub-housing 20 of the valve mechanism 3. The carrier shaft pivot axis 135***a* extends transversely relative to the main central axis 132*a*. The distal valve 134 comprises a circular disc type distal valve plate member 136, which extends substantially radially from the distal valve carrier shaft 135, and is operable between a closed state illustrated in FIG. 48 sealably engaging a valve seat 142 formed by the sub-housing adjacent the distal end 133 of the instrument bore 132, and an open state illustrated in FIG. 49 with the distal end 133 of the instrument bore 132 open for accommodating the instrument 26 therethrough.

A proximal valve 137 is located at the proximal end 143 of the instrument bore 132 and comprises first and second proximal valve members 138 and 139 which are substantially similar to the first and second proximal valve members 41 and 42 of the proximal valve 40 of the valve mechanism 3. The first and second proximal valve members 138 and 139 are slideably mounted in the sub-housing 131 in a manner not shown, but substantially similar to the manner in which the first and second proximal valve members 41 and 42 are slideably mounted in the sub-housing 20, and the first and second proximal valve members 138 and 139 are slideable in the sub-housing 131 between a withdrawn state illustrated in FIG. 48 withdrawn from the instrument bore 132 into the sub-housing 131, and an engagement state illustrated in FIG. 49 with the first and second proximal valve members 138 and 139 sealably engaging the instrument 26 extending through the instrument bore 132.

A detecting means in this embodiment of the invention comprises a pair of detecting probes, namely, a first detecting probe 140 and a second detecting probe 141 extending into the instrument bore 132 for engaging a distal end 38 of the instrument 26 being urged through the instrument bore 132. The detecting probes 140 and 141 are located on opposite sides of the instrument bore 22. The first detecting probe 140 extends substantially radially from the distal valve carrier shaft 135 into the instrument bore 132 through a corresponding opening 146 in the sub-housing 131. The second detecting probe 141 extends substantially radially from a carrier shaft 144 into the instrument bore 132 through a corresponding opening 148 in the sub-housing 131. The carrier shaft 144 is pivotally carried in the sub-housing 131 about a carrier shaft pivot axis 144*a* in a manner substantially similar to the manner in which the primary pivot shaft 64 is pivotally carried in the sub-housing 20 of the valve mechanism 3. The pivot axis 144*a* of the carrier shaft 144 extends transversely relative to the main central axis 132*a* defined by the instrument bore 132. The pivot axes 135*a* of the distal valve carrier shaft 135 and the pivot axis 144*a* of the carrier shaft 144 extend parallel to each other and on respective opposite sides of the main central axis 132*a*.

The first and second detecting probes 140 and 141 are configured to engage the distal end 38 of an instrument 26 being urged distally through the instrument bore 132, and are urgeable by the distal end 38 of the instrument 26 distally from a first state illustrated in FIG. 48 to a second state illustrated in FIG. 49 as the distal end 38 of the instrument 26 is urged distally past the instrument bore 132. As the first and second detecting probes 140 and 141 are urged distally from the first state to the second state, the distal valve carrier shaft 135 and the carrier shaft 144 are pivoted around their respective pivot axes 135*a* and 144*a* in the directions of the arrows A and B, respectively. Pivoting of the distal valve carrier shaft 135 in the direction of the arrow A urges the distal valve member 136 from the closed state illustrated in FIG. 48 to the open state illustrated in FIG. 49.

A drive transmission means, in this embodiment of the invention, comprising a pair of drive transmissions 149 is provided for urging the first and second proximal valve members 138 and 139 from the withdrawn state to the engagement state in response to the first and second detecting probes 140 and 141 being urged from the first state to the second state. Each drive transmission 149 comprises a segment of a gear wheel 145 mounted on the corresponding one of the distal valve carrier shaft 135 and the carrier shafts 144 which are engageable and co-operable with corresponding first gear racks 147 located on the distal side of the first and second proximal valve members 138 and 139, respectively, for urging the first and second proximal valve members 138 and 139 from the withdrawn state to the engagement state as the first and second detecting probes 140 and 141 are urged from the first state to the second state.

Accordingly, as the first and second probes 140 and 141 are urged distally from the first state to the second state by the distal end 38 of an instrument 26 being urged distally through the instrument bore 132, the distal valve 134 is operated from the closed state to the open state, and the first and second proximal valve members 138 and 139 of the proximal valve 137 are urged from the withdrawn state to the engagement state to sealably engage the instrument 26 in the instrument bore 132. Accordingly, prior to the distal end 38 of the instrument 26 reaching the distal end 133 of the instrument bore 132, the distal valve 134 is in the open state, thereby allowing the instrument to pass through the distal end 133 of the instrument bore 132 unimpeded by the distal valve member 136, and without contact with the distal valve 136. Simultaneously, as the distal valve member 136 is being pivoted from the closed state to the open state, the first and second proximal valve members 138 and 139 are being urged from the withdrawn state to the engagement state for sealably engaging the instrument 26 in the instrument bore 132 in order to avoid the escape of any insufflating and other gases leaking proximally from the trocar.

The first and second detecting probes 140 and 141 are configured so that for so long as the instrument 26 is located in the instrument bore 132, the action of the instrument 26 on the first and second detecting probes 140 and 141 retains the detecting probes 140 and 141 in the second state with the distal valve 134 in the open state and the proximal valve 137 in the engagement state.

An urging means, for example, one or a pair of torsion springs (not shown) located on the distal valve carrier shaft 135 and on the carrier shaft 144 acting between the sub-housing 132 and the first gear segments 145 are configured for urging the first and second detecting probes 140 and 141 from the second state to the first state as the distal end 38 of the instrument 26 passes the detecting probes 140 and 141 as the instrument 26 is being withdrawn proximally from the instrument bore 132. This, thus, results in the first and second detecting probes 140 and 141 following the distal end 38 of the instrument 26 as the instrument 26 is being withdrawn proximally from the instrument bore 132. This in turn results in the distal valve 134 being urged from the open state to the closed state, and the first and second proximal valve members 138 and 139 being urged from the engagement state to the withdrawn state.

Otherwise, the valve mechanism 130 according to this embodiment of the invention and its use and operation is substantially similar to that of the valve mechanism 3 described with reference to FIGS. 1 to 25.

Referring now to FIGS. 50 and 51 there is illustrated a portion of a valve mechanism in diagrammatic form also according to the invention and indicated generally by the reference numeral 150. The valve mechanism 150 is provided in a housing within which the components illustrated in FIGS. 48 and 49 are housed in a similar manner as the components of the valve mechanism 3 are housed in the housing 7 of the valve mechanism 3. The valve mechanism 150 is also configured for securing to a trocar cannula similar to the trocar cannula 2 to the proximal end 4 thereof. The valve mechanism 150 comprises a sub-housing 151 which defines an instrument bore 152 extending therethrough from a proximal end 153 to a distal end 154. The instrument bore 152 defines a longitudinally extending main central axis 156.

A distal valve 155 substantially similar to the distal valve 28 of the valve mechanism 3 is located adjacent the distal end 154 of the sub-housing 151 for closing the instrument bore 152. The distal valve 155 comprises a valve plate member 163 which is operable between a closed state illustrated in FIG. 50 sealably closing the instrument bore 152 and an open state illustrated in FIG. 51 for accommodating an instrument 26 unimpeded therethrough. The valve plate member 163 is pivotally carried on a distal valve pivot shaft 159 which is pivotally mounted in the sub-housing 152 about a distal valve pivot axis 161. The distal valve pivot shaft 159 is pivotally mounted in the sub-housing 151 in a manner substantially similar to that in which the distal valve carrier shaft of the valve mechanism 3 is pivotally carried in the sub-housing 20 thereof. The valve plate member 163 is pivotal about the distal valve pivot axis 161 between the closed state and the open state. The distal valve pivot axis 161 extends substantially transversely relative to the main central axis 156 of the instrument bore 152.

A proximal valve, which in this embodiment of the invention, comprises a resiliently deformable proximal ring seal 158 is located in the sub-housing 151 adjacent the proximal end 153 of the instrument bore 152. The ring seal 158 is located in an annular slot 160 extending circumferentially around and through the sub-housing 151. The ring seal 158 is of thickness $t_1$, which is greater than the thickness $t_2$ of the sub-housing 151 which defines the instrument bore 152, and is resiliently biased outwardly from the instrument bore 152. A collar 162 extending around the outer periphery of the sub-housing 151 is slideable in a proximal direction from a first state illustrated in FIG. 50 located distally from the ring seal 158 but adjacent thereto, to a second state illustrated in FIG. 51 with the collar 162 extending around and embracing the resilient ring seal 158. In the first state of the collar 162, the ring seal is in its normal non-deformed withdrawn state withdrawn from the instrument bore 152. In the second state of the collar 162, the ring seal 158 is deformed by the collar 162 into a deformed engagement state extending into the instrument bore 152 for sealably engaging the instrument 26 in the instrument bore 152.

A detecting means, in this embodiment of the invention a pair of detecting probes, namely, a first detecting probe 164 and a second detecting probe 165 are slideably mounted in corresponding openings 166 and 167, on opposite sides of the instrument bore, and extend inwardly through the openings 166 and 167 into the instrument bore 152. The first and second detecting probes 164 and 165 terminate in distal instrument engagement tips 168 for engaging the distal end 38 of the instrument 26. The first detecting probe 164 is spaced apart proximately from the second detecting probe 165 along the instrument bore 152. The first detecting probe 164 is urgeable by the distal end 38 of the instrument 26 from a first state extending into the instrument bore 152 illustrated in FIG. 50, radially outwardly from the instrument bore 152, to a second state illustrated in FIG. 51 clear of the instrument bore 152, as the distal end 38 of the instrument 26 passes the first detecting probe 164 as the instrument is being urged distally into the instrument bore 152. The first detecting probe 164 carries a first gear rack 169 which is engageable with a first intermediate gear wheel 170 which is rotatably mounted in the sub-housing 151 on a first intermediate shaft 173. The first intermediate gear wheel 170 cooperates with a segment of a first gear wheel 171 located on the distal valve carrier shaft 159 which carries the valve plate member 163 thereon for transmitting drive from the first gear rack 169 to the first gear wheel segment 171. Thus, as the first detecting probe 164 is urged radially outwardly from the instrument bore 152 from the first state to the second state, the distal valve 155 is urged from the closed state to the open state by drive transmitted through the intermediate gear 170 from the first gear rack 169 to the gear wheel segment 171.

The second detecting probe 165 is slideable radially outwardly through the opening 167 by engagement of the distal end 38 of the instrument 26 from a first state illustrated in FIG. 50 to a second state illustrated in FIG. 51 as the distal end 38 of instrument 26 passes the second detecting probe 165 moving distally. The second detecting probe 165 carries a second gear rack 174, which is engageable with a second intermediate gear wheel 175 which is rotatably mounted in the sub-housing 151 on a second intermediate shaft 172. The second intermediate gear wheel 175 drives a third intermediate gear wheel 177, which is rotatably mounted in the sub-housing 151 on a third intermediate shaft 176. The third intermediate gear wheel 177 cooperates with a third gear rack 178 carried on an actuator member 179 which is connected to the collar 162. Accordingly, as the second detecting probe 165 is urged radially outwardly from the first state to the second state, drive is transmitted from the second gear rack 174 to the third gear rack 178 through the second and third intermediate gears 175 and 177, for urging the actuator member 179, proximally from a first state illustrated in FIG. 50 to a second state illustrated in FIG. 51, for in turn urging the collar 162 proximally from the first state to the second state. As the collar 162 is urged from the first state to the second state the ring seal is deformed from the withdrawn state to the engagement state into the instrument bore 152 to sealably engage the instrument 26 in the instrument bore 152.

A suitable urging means (not shown), for example, spring urging or resilient urging is provided for urging the first and second detecting probes 164 and 165 from the second state to the first state, so that as the distal end 38 of the probe 26 passes the first and second detecting probes 164 and 165 with the instrument 26 moving proximally through the instrument bore 152, the first and second detecting probes 164 and 165 are urged from the second state to the first state. The urging means may act directly on the first and second detecting probes 164 and 165, or may act on any of the intermediate gears or the gear wheel segment 171 or on the collar or the actuator member or on the valve plate member 163 in a manner which would urge the collar 162 from the first state to the second state or would urge the valve plate member 163 from the closed state to the open state. Such an urging means if it were acting on the intermediate gears could be provided by a torsion spring or if it were acting on the gear wheel segment 171 could likewise be a torsion spring. If the urging means were provided to act on the collar

162 or the actuator member 179, the urging means could be provided as a tension or a compression spring and more likely a compression spring.

In use, the valve mechanism 150 is secured to the proximal end 4 of the trocar cannula 2 in a similar manner as the valve mechanism 3 is secured to the trocar cannula 2. As an instrument 26 is being urged distally into the instrument bore 152, the distal end 38 of the instrument 26 initially engages the first detecting probe 164 which in turn is urged radially outwardly from the instrument bore 152 from the first state thereof to the second state thereof as the distal end 38 of the instrument 26 passes the first detecting probe 164. The urging of the first detecting probe 164 from the first state to the second state results in the distal valve 155 being urged from the closed state to the open state, so that prior to the distal end 38 of the instrument 26 reaching the distal end 154 of the instrument bore 152 the distal valve 155 is in the open state to permit passage of the instrument 26 therethrough unimpeded and without contact between the instrument 26 and the valve plate member 163 of the distal valve 155.

Further urging of the instrument 26 distally in the instrument bore 152 results in the second detecting probe 165 being urged radially outwardly from the instrument bore 152 from the first state to the second state as the distal end 38 of the instrument 26 passes the second detecting probe 165. This in turn results in the collar 162 being urged by the actuator member 179 from the first state to the second state. As the collar 162 is being urged from the first state to the second state the ring seal 158 is deformed and urged from the withdrawn state to the engagement state sealably engaging the instrument 26.

For so long as the instrument 26 remains in the instrument bore 152 the first and second detecting probes 164 and 165 are retained by the instrument 26 in the second states thereof, thereby resulting in the distal valve 155 being retained in the open state and the ring seal 158 being retained by the collar 162 in the engagement state sealably engaging the instrument in the instrument bore 152. As the instrument 26 is being withdrawn proximally through the instrument bore 152, as the distal end 38 of the instrument 26 passes the second and first detecting probes 165 and 164, respectively, the second and first detecting probes 165 and 164, under the action of the spring urging thereof, are sequentially urged from the second state to the first state. This in turn results in the collar 162 being urged from the second state to the first state, which in turn results in the ring seal 158 returning under its own inherent resilience from the engagement state to the withdrawn state withdrawn from the instrument bore 152, and the distal valve 152 being urged from the open state to the closed state.

Otherwise, the valve mechanism and its use and operation is substantially similar to that of the valve mechanism 3 described with reference to FIGS. 1 to 25.

It is envisaged that in some versions of the embodiment of the invention of FIGS. 50 and 51, the positions of the detecting probes 164 and 165 may be reversed, so that the second detecting probe 165 would be located extending into the instrument bore 152 proximally of the first detecting probe 164. This would result in the sealing ring 158 being operated from the withdrawn state to the engagement state prior to the distal valve 155 being operated from the closed state to the open state, on the instrument 26 being urged distally through the instrument bore 152, and vice versa as the instrument 26 is being withdrawn through the instrument bore 152. Alternatively, the first and second detecting probes may be aligned with each other, so that the first and second detecting probes 164 and 165 would be operated simultaneously from the first states thereof to the second states thereof, and vice versa.

Referring now to FIGS. 52 and 53 there is illustrated a valve mechanism according to the invention and indicated generally by the reference numeral 180. The valve mechanism 180 is only partially illustrated, and comprises a main housing (not shown) within which the components illustrated in FIGS. 52 and 53 are housed. The valve mechanism 180 is configured for securing to a trocar cannula, similar to the trocar cannula 2, and is secured to the proximal end 4 of the trocar cannula 2. In this embodiment of the invention the valve mechanism 180 comprises a sub-housing 182 which defines an elongated instrument bore 184 extending therethrough from a proximal end 185 to a distal end 186.

A distal valve 187 is pivotally connected to the sub-housing 182 adjacent the distal end 186 of the sub-housing 182. In this embodiment of the invention a mechanism for operating the distal valve 187 between the closed and the open state is not illustrated, however, such a mechanism for operating the distal valve 187 between the closed and the open state will be provided, and may be similar to any of those mechanisms described already with reference to the already described valve mechanisms.

The valve mechanism 180 also comprises a proximal valve, in this case provided by a ring seal 189 located adjacent the proximal end 185 of the instrument bore 184. The ring seal 189 in this embodiment of the invention comprises a deformable resilient annular member 190 located in the instrument bore 184 adjacent the proximal end thereof in an annular recess 191. The annular member 190 is deformable from a withdrawn state illustrated in FIG. 52 withdrawn into the annular recess 191, to an engagement state illustrated in FIG. 53 with the annular member 190 sealably engaging an instrument 26 extending through the instrument bore 184.

In this embodiment of the invention the annular recess 191 is located between an inwardly extending annular flange 192 extending inwardly into the instrument bore 184 from the sub-housing 182, and an operating collar 194 located in the instrument bore 184 distally from the deformable resilient annular member 190. The operating collar 194 is slideable longitudinally in the instrument bore 184, and is slideable proximally from a first state illustrated in FIG. 52 with the annular member 190 in the withdrawn state to a second state illustrated in FIG. 53 bearing on the annular member 190 for urging the annular member 190 from the withdrawn state to the engagement state illustrated in FIG. 53 with the annular member 190 sealably engaging the instrument 26.

A pair of detecting probes, namely, a first detecting probe 195 and a second detecting probe 196 extend into the instrument bore 184, and are engageable by the distal end 38 of the instrument 26 as the instrument 26 is urged distally through the instrument bore 184. Each of the first and second detecting probes 195 and 196 terminate in a distal instrument engagement tip 197 engageable with the distal end 38 of the instrument 26 as the instrument 26 is being urged distally through the instrument bore 184. The first and second detecting probes 195 and 196 extend into the instrument bore 184 through corresponding openings 198 in the sub-housing 182. Each first and second detecting probe 195 and 196 is provided with a guide slot 199, which in turn is engageable with a corresponding guide pin 200 secured in the sub-housing 182. The guide pins 200 and the guide slots 199 of the first and second detecting probes 195 and 196 cooperate, so that as the instrument 26 is being urged distally through the instrument bore 184, the distal end 38 of the instrument 26 urges the first and second detecting probes 195 and 196 in a distal and radially outwardly direction from a first state illustrated in FIG. 52 extending into the instrument bore 184, to a second state illustrated in FIG. 53 clear of the instrument bore 184.

The first and second detecting probes 195 and 196 are also provided with respective camming surfaces 202 which cooperate with corresponding camming surfaces 203 of the operating collar 194, so that as the first and second detecting probes 195 and 196 are urged from the first state to the second state by the instrument 26, the cooperating action of the camming surfaces 202 and 203 urge the operating collar 194 proximally in the instrument bore 184, for in turn deforming the annular member 190 from the withdrawn state to the engagement state sealably engaging the instrument 26. The inherent resilience of the annular member 190 is configured to act to return the annular member 190 from the engagement state to the withdrawn state on the operating collar 194 being urged from the second to the first state.

A suitable urging means, for example, a spring (not shown) is provided for urging the operating collar 194 from the second state to the first state as the distal end 38 of the instrument 26 passes the first and second detecting probes 195 and 196 as the instrument 26 is being withdrawn through the instrument bore 184. The urging means may act on the operating collar or on the first and second detecting probes 195 and 196 for urging the operating collar 194 and/or the first and second detecting probes 195 and 196 from the second states thereof to the first states thereof.

Otherwise, the valve mechanism 180 and its operation is substantially similar to that of the valve mechanism 3.

Referring now to FIGS. 54 and 56 there is illustrated a valve mechanism according to another embodiment of the invention indicated generally by the reference numeral 210. The valve mechanism 210 is illustrated diagrammatically only in FIGS. 54 to 56, and comprises a housing (not shown) in which the components illustrated in FIGS. 54 to 56 are housed in a similar manner as that of the valve mechanism 3. In this embodiment of the invention the housing (not shown) is configured for releasably securing to a proximal end of a trocar cannula, for example, to the proximal end 315 of the trocar cannula 312, described with reference to FIGS. 31 and 32. The valve mechanism 210 is also configured to operate the duckbill valve 318 of the trocar cannula 312 from the closed state to the open state in response to an instrument being urged distally through an instrument bore (not shown) of the valve mechanism 210. The valve mechanism 210 comprises a sub-housing (also not shown) which defines an instrument bore for accommodating an instrument such as the instrument 26 therethrough.

A proximal valve 215 comprises a pair of first and second proximal valve members 215 and 216, which are slideably mounted in the sub-housing (not shown) in a manner substantially similar to that in which the first and second proximal valve members 41 and 42 are slideable in the sub-housing 20 of the valve mechanism 3. The first and second proximal valve members 215 and 216 are slideable between a withdrawn state illustrated in FIGS. 54 and 55 within the sub-housing (not shown) and an engagement state illustrated in FIG. 56 with the first and second proximal valve members 215 and 216 sealably engaging the instrument 26 in the instrument bore (not shown). In this embodiment of the invention the proximal valve members 215 and 216 are provided with arcuate central sealing portions 217 which are similar to the central sealing portions 55 and 56 of the first and second proximal valve members 41 and 42 of the valve mechanism 3. The central sealing portions 217 of the proximal valve members 215 and 216 similarly sealably engage the instrument 26 when the proximal valve members 215 and 216 are in the engagement state.

A pair of detecting probes 212 are provided for detecting the distal end 38 of the instrument 26. The detecting probes 212 are pivotally mounted in the sub-housing, and are operable between a first state illustrated in FIGS. 54 and 55 extending into the instrument bore, and a second state illustrated in FIG. 56 withdrawn from the instrument bore, and clear of the instrument bore. The detecting probes 212 in the first state thereof are engageable by the distal end 38 of the instrument 26 as the instrument 26 is urged distally through the instrument bore, and are urgeable from the first state to the second state by the distal end 38 of the instrument 26, as the distal end 38 passes the detecting probes 212 distally.

A transmission means, in this embodiment of the invention respective linkage mechanisms 219 couple the first and second proximal valve members 215 and 216 to the detecting probes 212, for transmitting drive from the detecting probes 212, as they are urged from the first state to the second state, to the first and second proximal valve members 215 and 216, for in turn urging the first and second proximal valve members 215 and 216 from the withdrawn state to the engagement state. An active operating means comprising a pair of active operating members 220 extend downwardly from the detecting probes 212 for operating the duckbill valve 318 of the trocar cannula 312 from the closed state to the open state as the detecting probes 212 are urged from the first state to the second state.

Otherwise, the valve mechanism 210 and its operation is substantially similar to the valve mechanism 3 described with reference to FIGS. 1 to 25.

Referring now to FIGS. 57 and 58 there is illustrated a portion of valve mechanism according to another embodiment of the invention indicated generally by the reference numeral 230. The valve mechanism 230 comprises a housing (not shown) within which the components illustrated in FIGS. 57 and 58 are housed. In this case, the housing is configured for securing to the proximal end 315 of the trocar cannula 312. In this embodiment of the invention the valve mechanism 230 comprises a sub-housing (not shown) which defines an instrument bore (also not shown) extending through the sub-housing from a proximal end to a distal end. A proximal valve is provided adjacent the proximal end of the instrument bore, and in this embodiment of the invention comprises an annular seal 232. The annular seal 232 comprises three sealing segments 234, each of which extends through an angle of 120°. The sealing segments 234 of the annular seal 232 are carried on respective corresponding carrier segments 235, each of which extends through a corresponding angle of 120°. The carrier segments 235 are carried on carrier members 236 which are pivotally carried in the sub-housing on pivot pins 237, so that the carrier segments 235 and in turn the sealing segments 234 of the annular seal 232 are urgeable from a withdrawn state illustrated in FIG. 57 within the sub-housing (not shown) to an engagement state illustrated in FIG. 58 extending into the instrument bore (not shown) for sealably engaging the instrument 26 in the instrument bore (not shown).

Three detecting probes 238 extend radially inwardly from the respective carrier members 236, and are configured to extend through corresponding openings in the sub-housing (not shown) and in turn into the instrument bore (also not shown). The detecting probes 238 each terminate in a distal instrument engagement tip 239 for engaging the distal end

38 of the instrument 26 as the instrument 26 is being urged distally through the instrument bore (not shown). The detecting probes 238 are configured to be pivotal on the corresponding pivot pin 237 and are pivotal distally in the instrument bore from a first state illustrated in FIG. 57 to a second state illustrated in FIG. 58 as the distal end 38 of the instrument 26 passes the detecting probes 238 in a distal direction. Thus, as the detecting probes 238 are urged from the first state distally to the second state, the carrier members 236 are pivoted about the pivot pins 237 in the direction of the arrow M for in turn urging the sealing segments 234 of the annular seal 232 from the withdrawn state to the engagement state sealably engaging the instrument 26.

An active operating means comprising three operating members 240 extend distally from the detecting probes 238 for operating the duckbill valve 318 of the trocar cannula 312 from the closed state to the open state. The operating members 240 pivot with the detecting probes 238 and with the carrier members 236, so that as the detecting probes 238 pivot about the pivot pins 237 from the first state to the second state, the operating members 240 are urged from a disengaged state illustrated in FIG. 57 to an engagement state illustrated in FIG. 58 for urging the duckbill valve 318 of the trocar cannula 312 from the closed state to the open state.

Otherwise, the valve mechanism 230 and its operation is substantially similar to the valve mechanism 3 described with reference to FIGS. 1 to 25.

Referring now to FIGS. 59 and 60 there is illustrated a valve mechanism according to another embodiment of the invention indicated generally by the reference numeral 250. The valve mechanism 250 comprises a sub-housing 252 which is located within a housing similar to the housing 7 of the valve mechanism 3 of FIGS. 1 to 25. The valve mechanism 250 is similarly configured for releasably securing to a distal end 4 of a trocar 2. The sub-housing 252 defines a longitudinally extending instrument bore 253 which extends from a proximal end 254 to a distal end 255.

A proximal valve 256 is located adjacent the proximal end 254 of the sub-housing 252, which in this embodiment of the invention comprises a proximal iris valve 257, located in a proximal recess formed in the sub-housing 252 within the instrument bore 253 adjacent the proximal end thereof. The proximal iris valve 257 is operable from a withdrawn state illustrated in FIG. 59 with the proximal iris valve 257 in an open state and withdrawn into a proximal recess 258, to an engagement state illustrated in FIG. 60 with the proximal iris valve 257 in a partly closed state extending into the instrument bore 253, and sealably engaging an instrument 26 extending through the instrument bore 253.

A distal valve 259 comprising a distal iris valve 260 is located adjacent the distal end 255 of the instrument bore 253 in a distal recess 261 formed in the sub-housing 252 within the instrument bore 253. The distal iris valve 260 is urgeable from a closed state illustrated in FIG. 59 closing the instrument bore 253, to an open state illustrated in FIG. 60 withdrawn into the distal recess 261 for accommodating unimpeded access of the instrument 26 through and from the instrument bore 253.

A collar 262 which is rotatable and longitudinally slideable in the instrument bore 253 couples the proximal iris valve 257 with the distal iris valve 260, so that as the collar 262 is urged proximally in the instrument bore 253 from a first state illustrated in FIG. 59 to a second state illustrated in FIG. 60, the distal iris valve 260 is operated from the closed state to the open state and the proximal iris valve 257 is operated from the withdrawn state to the engagement state.

A detecting probe 263 extends radially inwardly from the sub-housing 252 into the instrument bore 253, and engages a camming slot 264 formed in the collar 262. The detecting probe 263 is slideable longitudinally in the sub-housing from a first state illustrated in FIG. 59 in a distal direction, namely, the direction of the arrow S, to a second state illustrated in FIG. 60, so that as the detecting probe 263 is urged distally from the first state to the second state, the action of the detecting probe 263 on the camming slot 264 in the collar 262, rotates the collar 262 in the direction of the arrow N, and thereby urges the collar 262 proximally in the instrument bore 253 from the first state to the second state for operating the proximal iris valve 257 from the withdrawn state to the engagement state, and for operating the distal iris valve 260 from the closed state to the open state. Therefore, as the detecting probe 263 is urged distally from the first state to the second state by the distal end 38 of an instrument 26 being urged distally through the instrument bore 253, the proximal iris valve 257 is urged from the withdrawn state to the engagement state for sealably engaging the instrument 26, and the distal iris valve 260 is operated from the closed state to the open state for accommodating the instrument 26 therethrough, and in turn into a trocar cannula unimpeded by the distal iris valve 260.

While the valve mechanisms have been described as comprising a housing of a particular shape and construction, the valve mechanisms may be provided with housings of any other shape or construction. Indeed, in some embodiments of the invention the housings may be provided without the peripheral wall and the top wall. It is also envisaged that with or without the peripheral wall, the valve mechanism may be fitted into the proximal trocar housing of a trocar, and the housing forming the proximal trocar housing of the trocar could form the outer housing of the valve mechanism.

It will also be appreciated that any other suitable urging means for urging the detecting probe from the second state to the first state, and also for urging the proximal valve from the engagement state to the withdrawn state, and for urging the distal valve from the open state to the closed state, may be provided besides a compression spring, for example, a tension spring, a torsion spring, a pneumatic spring, or any other resilient or spring like element. Needless to say, such urging means may be located in any suitable location, and may act between the housing of the valve mechanism and any one or more of the detecting probe, the proximal valve and the distal valve. It will also be appreciated that any other suitable urging means for urging the operating means from the engagement state to the disengagement state may be provided besides a compression spring, for example, a tension spring, a torsion spring, a pneumatic spring, or any other resilient or spring like element, and such urging means may be located to act between the housing and the operating means, or between the housing and the proximal valve, the detecting probe or the distal valve, and the operating means could be operably coupled to any one of the detecting probe, the proximal valve or the distal valve, such that the urging means when urging the one of the detecting probe, the proximal valve and the distal valve, would simultaneously urge the operating means from the engagement state to the disengaged state.

In some embodiments of the invention it is envisaged that a separate urging means may be provided for urging the detecting probe or probes from the second state to the first state which would be separate and independent of the urging means for urging the proximal valve from the engagement state to the withdrawn state, and furthermore, a separate urging means may be provided for urging the distal valve from the open state to the closed state, and also for urging the operating means from the engagement state to the disengaged state. Needless to say, while some valve mechanisms have been described as comprising a single detecting probe, more than one detecting probe may be provided.

While specific types of distal valves have been described in the valve mechanisms according to the invention, it will be appreciated that other types of distal valves may be used without departing from the scope of the invention, for example, a gate valve. Indeed, it is envisaged that in some embodiments of the invention the distal valve may be omitted from the valve mechanism.

Additionally, while specific proximal valves have been described, any other suitable proximal valves may be provided. While the proximal valves have been described as comprising slidably mounted proximal valve members, which slide towards and away from each other with rectilinear motion, it is envisaged that in some embodiments of the invention the proximal valve members may be pivotally mounted and would pivot between the withdrawn state and the engagement state. For example, each proximal valve member would be pivotal about a corresponding pivot axis, and the pivot axes of the respective proximal valve members would extend parallel to each other. The proximal valve members would then pivot between the withdrawn state and the engagement state through planes extending perpendicularly to the respective pivot axes, and the planes through which the proximal valve members would pivot between the withdrawn state and the engagement state would be parallel to each other, or the proximal valve members would pivot about the respective pivot axes through a common plane between the withdrawn states and the engagement states. It is also envisaged that while the proximal valve has been described as comprising two proximal valve members which together define a bore of cross-section substantially corresponding to the cross-section of the instrument with which the proximal valve members are to form a seal, it is envisaged that in some embodiments of the invention more than two proximal valve members may be provided which would cooperate with each other to define a bore of transverse cross-section substantially corresponding to the transverse cross-section of the instrument. Each of the proximal valve members would be urgeable between the withdrawn state and the engagement state.

It will be appreciated that in some embodiments of the invention the collecting ports may be omitted, and it will also be appreciated that all the valve mechanisms according to the invention may be provided with collecting ports for collecting insufflating and other gases adjacent the proximal end of the instrument bore. Indeed, in some embodiments of the invention a single collecting port may be provided, and in other embodiments of the invention the collecting port or ports may communicate with the instrument bore of the valve mechanism distally of the proximal valve, rather than proximally of the proximal valve.

While some of the valve mechanisms have been described for operating a particular type of a duckbill valve in a trocar cannula, it will be appreciated that the valve mechanisms, which are provided with an active or a passive operating means for operating a duckbill valve in a trocar cannula or in a trocar from a closed state to an open state may be provided with an active or a passive operating means or both an active and a passive operating means for operating any type of access valve in a trocar cannula or a trocar, or any type of duckbill valve in a trocar cannula.

While the valve mechanisms have been described for accommodating a laparoscope therethrough, it will be readily apparent to those skilled in the art that the instrument bore of the valve mechanisms may be configured to accommodate any other instrument, for example, an endoscope or any other surgical or medical instrument. In general, it is envisaged that the proximal valve seal will be sized to suit the instrument to which the instrument bore of the valve mechanism is configured to accommodate. Needless to say, it will be appreciated that the valve mechanisms may be configured to accommodate a number of different instruments of different transverse cross-sectional shape and/or size, and in which case, the proximal valve would be selected to sealably engage all such instruments.

It is also envisaged that in some embodiments of the invention the proximal valve of the valve mechanism may be adapted to operate with instruments of different transverse cross-sectional dimensions. In which case, it is envisaged that the proximal valve members would be provided with a resilient flexible seal for engaging the outer periphery of the instrument, and the resilient flexible seals would be of such resilience and flexibility as to be capable of effecting a seal with instruments of different transverse cross-sectional dimensions, for example, different transverse cross-sectional diameters within a specific range of cross-sectional dimensions or diameters.

Further, it is envisaged that the proximal valve members of the proximal valve may be located to be readily replaceable and interchangeable in order to accommodate instruments of different transverse cross-sectional sizes and shapes.

While specific types of detecting probes have been described, it will be readily apparent to those skilled in the art that detecting probes of different size, shape and construction may be provided. It will also be appreciated that other suitable means for mounting the detecting probes, rather than mounting the detecting probes to be pivotal between the first state and the second state may be provided. For example, in some embodiments of the invention it is envisaged that the detecting probe or probes may be slideably mounted to slide between the first and second states.

While in the embodiments of the invention described, the detecting means has been described as comprising an active detecting means, whereby the detecting means is moveable between a first state and a second state, it is envisaged that in some embodiments of the invention that the detecting means may be provided in the form of a passive detecting means, for example, a sensor, such as, for example, a proximity sensor, which may comprise an ultrasonic sensor or a hall effect sensor. In which case, on a distal end of an instrument being detected moving distally through the instrument bore, the sensor would produce a signal indicative of the distal end of the instrument moving distally through the instrument bore, which in turn would activate one or more suitable mechanisms for operating the proximal and distal valves and the operating means appropriately. On detecting the distal end of an instrument moving proximally through the instrument bore of the valve mechanism, the sensor would produce a corresponding signal to operate the one or more operating mechanisms in the reverse to appropriately operate the proximal and distal valves and the operating means. Such operating mechanisms may, for example, be spring operated, and/or may be power driven.

While the valve mechanisms according to the invention have been described for securing to the proximal end of a trocar cannula, it is envisaged that the valve mechanisms according to the invention may also be secured to a trocar, whereby the valve mechanisms would be secured to the proximal end of the proximal trocar housing, and in which case, a suitable securing means would be provided for securing the valve mechanisms to the proximal trocar housing of the trocar. The operating means if provided, if desired may then be configured to operate an access valve in the proximal trocar housing from the closed state to the open state.

It will also be appreciated that other securing means for securing the valve mechanisms to a trocar cannula or a proximal trocar housing of a trocar besides the securing means described, may be provided, and it will be appreciated that the securing means in general will be adapted to the type of trocar cannula or the proximal trocar housing of the trocar or trocars to which the valve mechanism or valve mechanisms are to be secured.

The invention claimed is:

1. A valve mechanism for a trocar or a trocar cannula, the valve mechanism comprising:

a housing having an instrument bore extending therethrough from a proximal end to a distal end and defining a longitudinally extending main central axis, a detecting means located in the housing configured to detect an instrument in or passing through the instrument bore, a proximal valve located in the housing proximally of the detecting means and being operable from a withdrawn state to an engagement state engaging the instrument in the instrument bore to form a seal with the instrument for minimising leakage of gas past the proximal valve in response to the detecting means detecting an instrument passing distally in the instrument bore, and a distal valve located distally of the detecting means operable from a closed state closing the instrument bore to an open state permitting passage of an instrument through the instrument bore in response to the detecting means detecting an instrument passing distally in the instrument bore, so that as the distal valve is operating from the closed state to the open state, the proximal valve is simultaneously operating from the withdrawn state to the engagement state.

2. A valve mechanism as claimed in claim 1 in which the detecting means is configured to extend into the instrument bore for engaging an instrument in the instrument bore.

3. A valve mechanism as claimed in claim 2 in which the detecting means is moveably mounted in the housing, and is moveable in the instrument bore from a first state to a second state in response to movement of an instrument distally in the instrument bore.

4. A valve mechanism as claimed in claim 3 in which the proximal valve is urgeable from the withdrawn state to the engagement state and the distal valve is urgeable from the closed state to the open state in response to movement of the detecting means from the first state to the second state.

5. A valve mechanism as claimed in claim 3 in which the detecting means is configured to be urgeable from the first state to the second state by movement of an instrument distally in the instrument bore.

6. A valve mechanism as claimed in claim 3 in which a first transmission means is provided for transmitting movement of the detecting means from the first state to the second state to movement of the proximal valve from the withdrawn state to the engagement state, and a second drive transmission means is provided for transmitting movement of the detecting means from the first state to the second state to movement of the distal valve from the closed state to the open state.

7. A valve mechanism as claimed in claim 6 in which the first transmission means comprises a first drive transmission means.

8. A valve mechanism as claimed in claim 2 in which the detecting means is configured to engage a distal end of an instrument in the instrument bore.

9. A valve mechanism as claimed in claim 1 in which the proximal valve comprises a pair of proximal valve elements urgeable from the withdrawn state to the engagement state for engaging an instrument in the instrument bore.

10. A valve mechanism as claimed in claim 9 in which the proximal valve elements of the pair thereof are moveable between the withdrawn state and the engagement state transversely relative to the main central axis.

11. A valve mechanism as claimed in claim 9 in which the proximal valve elements of the pair thereof are located on respective opposite sides of the main central axis, and are moveable towards each other from the withdrawn state to the engagement state.

12. A valve mechanism as claimed in claim 1 in which an urging means is provided for urging the proximal valve into the withdrawn state and for urging the distal valve into the closed state.

13. A valve mechanism as claimed in claim 12 in which the urging means comprises a resilient urging means.

14. A valve mechanism as claimed in claim 12 in which the urging means is responsive to a distal end of an instrument in the instrument bore passing proximally past the detecting means for urging the proximal valve from the engagement state to the withdrawn state and for urging the distal valve from the open state to the closed state.

15. A valve mechanism as claimed in claim 1 in which the distal valve is located adjacent the distal end of the instrument bore.

16. A valve mechanism as claimed in claim 1 in which the valve mechanism is configured for mounting on a proximal end of a trocar or a trocar cannula with the instrument bore defined by the housing of the valve mechanism aligned with an instrument bore of the trocar or the trocar cannula.

17. An assembly comprising a trocar or a trocar cannula and the valve mechanism as claimed in claim 1 mounted on the trocar or the trocar cannula adjacent the proximal end thereof.

18. A valve mechanism as claimed in claim 1 in which the detecting means is pivotally mounted in the housing about a primary pivot axis, the primary pivot axis extending transversely relative to the main central axis defined by the instrument bore.

19. A valve mechanism as claimed in claim 18 in which the distal valve is pivotal about a distal valve pivot axis, and the distal valve pivot axis extends transversely of the main central axis defined by the instrument bore and parallel to the primary pivot axis.

20. A valve mechanism as claimed in claim 1 in which the housing terminates in a valve seat adjacent the distal end of the instrument bore and the distal valve is sealably engageable with the valve seat in the closed state.

* * * * *